(12) United States Patent
Griffey et al.

(10) Patent No.: US 9,550,990 B2
(45) Date of Patent: Jan. 24, 2017

(54) REGULATION OF EPIGENETIC CONTROL OF GENE EXPRESSION

(75) Inventors: Richard H. Griffey, Vista, CA (US); Timothy Vickers, Oceanside, CA (US); Ranjan Perera, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 2817 days.

(21) Appl. No.: 11/721,326

(22) PCT Filed: Dec. 12, 2005

(86) PCT No.: PCT/US2005/045063
§ 371 (c)(1),
(2), (4) Date: Jul. 29, 2009

(87) PCT Pub. No.: WO2006/063356
PCT Pub. Date: Jun. 15, 2006

(65) Prior Publication Data
US 2009/0298910 A1    Dec. 3, 2009

Related U.S. Application Data

(60) Provisional application No. 60/634,840, filed on Dec. 10, 2004.

(51) Int. Cl.
*C12N 15/11* (2006.01)
*C12N 15/113* (2010.01)

(52) U.S. Cl.
CPC .............. *C12N 15/113* (2013.01); *C12N 15/11* (2013.01); *C12N 15/111* (2013.01); *C12N 2310/11* (2013.01); *C12N 2310/14* (2013.01); *C12N 2310/315* (2013.01); *C12N 2310/321* (2013.01); *C12N 2310/3341* (2013.01); *C12N 2310/341* (2013.01); *C12N 2310/346* (2013.01); *C12N 2320/11* (2013.01); *C12N 2320/12* (2013.01); *C12N 2330/10* (2013.01); *Y10T 436/143333* (2015.01)

(58) Field of Classification Search
CPC ....................... C12N 15/111; Y10T 436/14333
See application file for complete search history.

(56) References Cited

U.S. PATENT DOCUMENTS

| 6,033,910 A | 3/2000 | Monia et al. |
| 2003/0143732 A1 | 7/2003 | Fosnaugh et al. |
| 2004/0180351 A1 | 9/2004 | Giese et al. |
| 2005/0112763 A1* | 5/2005 | Grewal et al. ............... 435/372 |

OTHER PUBLICATIONS

Leydier, C. et al., "4'-Thio-RNA: Synthesis of Mixed Base 4'-Thio-Oligoribonucleotides, Nuclease Resistance, and Base Pairing Properties with Complementary Single and Double Strand," Antisense Research and Development, 1995, 5, 167-174.
Esau et al., "MicroRNA-143 regulates adipocyte differentiation" Journal of Biological Chemistry (2004) 279(50):52361-52365.
Hall et al., "Establishment and maintenance of a heterochromatin domain" Science (2002) 297(5590):2232-2237.
Hutvagner et al., "Sequence-specific inhibition of small RNA function" PLOS Biology (2004) 2(4):1545-7885.
Krutzfeldt et al., "Silencing of microRNAs in vivo with 'antagomirs'" Nature (2005) 438(7068):685-689.
Meister et al., "Sequence-specific inhibition of microRNA- and siRNA-induced RNA silencing" RNA (2004) 10(3):544-550.
Poy et al., "A pancreatic islet-specific miroRNA regulates insulin secretion" Nature (2004) 432(7014):226-230.
Seitz et al., "Imprinted microRNA genes transcribed antisense to a reciprocally imprinted retrotransponson-like gene" Nature Genetics (2003) 34(3):261-262.
Weiler et al., "Anti-miRNA oligonucleotides (AMOs): ammunition to target miRNAs implicated in human disease?" Gene Therapy (2006) 13(6):496-502.
International Search Report for application PCT/US2005/045063 dated Apr. 27, 2006.

* cited by examiner

*Primary Examiner* — J. E. Angell
(74) *Attorney, Agent, or Firm* — Baker & Hostetler LLP

(57) ABSTRACT

Methods are provided for the identification of compounds that selectively modulate epigenetic changes in gene expression. Compounds, compositions, kits or assays devices, and methods are provided for modulating the expression, endogenous levels or the function of small non-coding RNAs cognate to or transcribed by heterochromatic regions subject to epigenetic regulation (i.e., promoters, enhancers, centromeres, telomeres, origins of DNA replication, imprinted loci, or loci marked by dosage-compensation), and for modulating the formation or function of heterochromatin in cells, tissues or animals.

4 Claims, No Drawings

SEQUENCE LISTING

```
<160> NUMBER OF SEQ ID NOS: 219

<210> SEQ ID NO 1
<211> LENGTH: 19
<212> TYPE: RNA
<213> ORGANISM: Artificial Sequence
<220> FEATURE:
<223> OTHER INFORMATION: synthetic oligomeric compound

<400> SEQUENCE: 1
cgagaggcgg acgggaccg                                                  19

<210> SEQ ID NO 2
<211> LENGTH: 19
<212> TYPE: RNA
<213> ORGANISM: Artificial Sequence
<220> FEATURE:
<223> OTHER INFORMATION: synthetic oligomeric compound

<400> SEQUENCE: 2
gcucuccgcc ugcccuggc                                                  19

<210> SEQ ID NO 3
<211> LENGTH: 21
<212> TYPE: DNA
<213> ORGANISM: Artificial Sequence
<220> FEATURE:
<223> OTHER INFORMATION: synthetic oligomeric compound
<220> FEATURE:
<221> NAME/KEY: misc_feature
<222> LOCATION: 1-19
<223> OTHER INFORMATION: bases at these positions are RNA

<400> SEQUENCE: 3
cgagaggcgg acgggaccgt t                                               21

<210> SEQ ID NO 4
<211> LENGTH: 21
<212> TYPE: DNA
<213> ORGANISM: Artificial Sequence
<220> FEATURE:
<223> OTHER INFORMATION: synthetic oligomeric compound
<220> FEATURE:
<221> NAME/KEY: misc_feature
<222> LOCATION: 3-21
<223> OTHER INFORMATION: bases at these positions are RNA
```

-continued

```
<400> SEQUENCE: 4
ttgcucuccg ccugcccugg c                                              21

<210> SEQ ID NO 5
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 5
tccgtcatcg ctcctcaggg                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 6
gtgcgcgcga gcccgaaatc                                                20

<210> SEQ ID NO 7
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 7
atgcattctg cccccaagga                                                20

<210> SEQ ID NO 8
<211> LENGTH: 67
<212> TYPE: DNA
<213> ORGANISM: H. Sapiens

<400> SEQUENCE: 8
ggatcgatga tgagaataat tgtctgagga tgctgaggga ctcattccag atgtcaatct    60
gaggtcc                                                              67

<210> SEQ ID NO 9
<211> LENGTH: 67
<212> TYPE: DNA
<213> ORGANISM: H. Sapiens

<400> SEQUENCE: 9
ttcctatgat gaggaccttt tcacagacct gtactgagct ccgtgaggat aaataactct    60
gaggaga                                                              67

<210> SEQ ID NO 10
<211> LENGTH: 76
<212> TYPE: DNA
<213> ORGANISM: H. Sapiens

<400> SEQUENCE: 10
gccaaatgat gtttatttga aacaggagca cctcagtgca aggacgactc ttatctatca    60
cccatgactg atggct                                                    76

<210> SEQ ID NO 11
<211> LENGTH: 71
```

```
<212> TYPE: DNA
<213> ORGANISM: H. Sapiens

<400> SEQUENCE: 11
gcttaatgat gagaatcatt atttcttgaa ttggatgaca ctttccattc ctgcaaaggg     60
agcgtgaggg c                                                         71

<210> SEQ ID NO 12
<211> LENGTH: 75
<212> TYPE: DNA
<213> ORGANISM: H. Sapiens

<400> SEQUENCE: 12
ggttcatgat gacacaggac cttgtctgaa cataatgatt tcaaaatttg agcttaaaaa     60
tgacactctg aaatc                                                     75

<210> SEQ ID NO 13
<211> LENGTH: 86
<212> TYPE: DNA
<213> ORGANISM: H. Sapiens

<400> SEQUENCE: 13
gatcacggtg atggctgacc agggctccct gacctataca ggcctctgct atggggtga     60 tggccagtcc tggtgtctga gtgatt                                         86

<210> SEQ ID NO 14
<211> LENGTH: 78
<212> TYPE: DNA
<213> ORGANISM: H. Sapiens

<400> SEQUENCE: 14
gccatatgat gttttctttt cgaaaggtga gcgctttgcg cagtgatgac cctcatctat     60 caccccttgac tgatggct                                                 78

<210> SEQ ID NO 15
<211> LENGTH: 109
<212> TYPE: DNA
<213> ORGANISM: H. Sapiens

<400> SEQUENCE: 15
tcccaatgat gagttgccat gctaatactg agccaccagg tagggcagtg ttgcctggtt    60
tgggtgccag tgagtttaac aaaacttctc acatgaagat ctgaggggt               109

<210> SEQ ID NO 16
<211> LENGTH: 69
<212> TYPE: DNA
<213> ORGANISM: H. Sapiens

<400> SEQUENCE: 16
gggcaatgat gaaaggtttt tactactgat ctttgtaact atgatggttt ctacacttga    60
cctgagctc                                                            69

<210> SEQ ID NO 17
<211> LENGTH: 125
<212> TYPE: DNA
<213> ORGANISM: H. Sapiens

<400> SEQUENCE: 17
tcccaatgaa gaaactttca catgtcttac tctctgtcct agtcccagag cctgtaaagg    60
```
tgaaccactg ggactggctg ggggagaaga ggaagatttg ttccagaagg aactgtctga    120
gggat                                                               125

<210> SEQ ID NO 18
<211> LENGTH: 1000
<212> TYPE: DNA
<213> ORGANISM: H. Sapiens

<400> SEQUENCE: 18
caggtggcac ccaggcctct ctgtgcctcg gctccagctg tctcttgtgg ctccccaccc     60
caaatcctgg caggtccctt ccccacagcc acccacccct ctcctccatc gggaacagaa    120
ctatgctgcc acctctggtg acctcagcac gctgcatcac tgtcccgtc cacgtgctac    180 cctgtgggcc caggagagcc ctggggtccc tgggtagcag agcgcctggc catgcctctg    240
aggcccctag tgccgcagag ttgagctgag gtctcgcgc tcgccctctg actgacccag    300
cccttgcagg tgagtggatt gctgtgctct ggtggcctga gggaggccac gcgccttctg    360
tgtgttccag aaagggtgcc tcccactgca tgcttgctta tctgagttag aagaatgctg    420
tggtggagtt tagtgtaaat ttttaaaata ttttttgagc cttatgatta tatagttttt    480
gtgtttctga gtaggaatt aaagtgggca ttaacaaaat atttaacttt ggacttaagt    540
tataattcag gttctgaaga ataaaagtaa ggttagtttg ttttgatgcc taaaaagtcc    600
tcttagggaa tattattttg aagcccttta ctatgctgtt aatagtgctt ggcttttaac    660
ttggtaccag ggaattggaa ggttctgtc attttgtgac gatatttta aatttctttg    720 caggtagaag aagaaaggtg ccactccggc atgaagacag actcgcttag tcgccagtca    780
cttaagctga gtgcattgtg atttccaata attgaggcag tggttctaaa agctgtctac    840
attaatgaaa agagcaatgt ggccagcttg actaagccgc cagcgcacag cgcggcagga    900
cgcgcccggg tctcagcgga cttgtgcatg ttagctgtgt agatttatgt gagggcttgt    960
aaaactctgg tcttgtaaac tagtcttaag cgcttttaat                        1000

<210> SEQ ID NO 19
<211> LENGTH: 1000
<212> TYPE: DNA
<213> ORGANISM: H. Sapiens

<400> SEQUENCE: 19
gtggcccgtt cctgagatgg ggccgaatct aaggttggcg accaggtaga gaagctggcc     60
cagccacacc cggctgccca aggagggaag gagcctgcct gtgcctagga gaagcctcgt    120
tcctgaatct gctgctttcc ccaagttggt ttttagggca gcaggtgccc ccgcaagtca    180
gaaatcctgc ctggattata tttcgtcttt ctctctgagg catagactta aagataggaa    240
acttaacagc tagggataaa acaaaaaaac atagcatatt gctgggcgct gtggttcacg    300
cctgtaatcc tgacactttg ggaggccag gcggtggatc acctgaggtg aggagtttga    360
gaccagcctg gccaacgtgg tgaaaccccg tctctactaa aaatacaaaa attagctggg    420
tgtggcggtg cacacctgta atcctagctc cttgggaggc tgagggatga gaatcacttg    480
aacccaggag gcggaggttg cagtgactcg agatcctgcc actgcactcc agcctgggcg    540
acagagtgag actctgtctc aacaaaacaa aacaaaccac cattctgtgg ttccaatgac    600
ctgtgccttg tcagggggt cacacagcct tgaaaggtaa cagttctagg ctcctgtgtg    660
cactggaaat acgtaactcg caggttctgg gaaagggatt tctcggaact taaaccggga    720
agtgatttga aaacttccag tatcactccc tttatcctct cagaaaagta ttttttttaag    780

```
ccactgaatg aatcaccctt gagttgcaca agaaggaaac attgcataga atgaaaaatg      840
acagcaaact gctgaggtca cttccccagg cccactgaat gagaatatca gttcctgtgc      900
tggagagaaa ggcagtcaga ggagaaaatg aggtccagct cgtccctggc tctctctctc      960
tctcaggtcc tgatgtcttt tccaagtctg gagagcagcg                           1000
```

<210> SEQ ID NO 20
<211> LENGTH: 1000
<212> TYPE: DNA
<213> ORGANISM: H. Sapiens

<400> SEQUENCE: 20

```
gcatgttatt tcctgaggag ttgtatttct tcacccctttt ttcctttgat ctcatattct      60
ctgactccag agcttccctg actctgtctt gcaaaatgct ttacctaaag ccttctttaa      120
gcctttattg agcccaagt cagcattaat ctcttcccct ccattaaaaa aaaactggaa       180
tggccattgt atgtatagta tgttccagcg taggttagtt ggctgttctt gtgtctgtct      240
cctactcttc tctaagcact aatggtttgc tttccaatag acggtgagct ccttgaggat      300
agcccctcta tttgtattat gtggcttaca ggttttaagc tataattttt taaggtttca      360
ttttattttg attctctatc gataagtaac agacattgaa ctctttgtga taaagtgtcc      420
tggaaagata ggagagaaat gataataaaa aagatattaa aatatacttc aggaaacatt      480
agccaagtca atttaataca agtatattc agatgcccag gaatacagaa cagtcatgag       540
cagaaatgac cagtgttaat caaggaagtt tcaaacattt ttgtaggtta atgaacaagt      600
atggcctgaa aataagcact gggccatgtg gtgattggaa aacacaaaat ggaaatccag      660
aaggatgagt gagggaagag tgataaaacca tctctgtaat cttatgtttt atggtatgtg     720
cagtgcaagt tttatagcca tagaaactct ttggaaacta ttcaaagaca gcccagtcca      780
atttcaaact tttgaacttc tcttagtggc tactactttt tacacttttt ctggaatttt      840
tgtataacat ctttatttt tctcagtttt atatataatc attatgtact tacaggaagg       900
taaaggacaa attttacata ttttttttcca ctaaaagtat attgcattct tttttttgtaa   960 cagattcatg cccaagcaca aaacaaccca tttaaagaag                           1000
```

<210> SEQ ID NO 21
<211> LENGTH: 1000
<212> TYPE: DNA
<213> ORGANISM: H. Sapiens

<400> SEQUENCE: 21

```
gagaaggaag gaaagaagg aaggaaggaa agaaagaaag aaagagagag agagagaaag       60
aaagaaagaa agaagaaag aaagaaagaa agaagaatt gaagttagct gagtgtggtg        120
gtgcatctgt aattccagct acttgagagg ccgaggtggg aggatcgctt gagcccggga      180
gttccagtct gcagtgagct atgtatgatc acatcactgc actctagcct gggtgacaga      240
gtgagacccc atctcaaaaa aataaaaata agaagtggg gctgggcgcg gtggctcacg       300
cctgtaatcc cagcactttg ggaggctgag gcatgcagat cacctgaggt caggagtttg      360
agaccagcct gtctaacatg ctgaaatccc atctctacta aaaatacaaa aattagccag      420
gcatggtggt ggacacctgt aatcccagct actcaggagg ctgaggcagg agagttgttt      480
gaacctggga ggcggaggtt gcagtgagcc gagatggtac ctttgcactc cagccttggc      540
aacagaacga gaccccatct caaaaaaaaa aaaaaaaaaa aaaagaagtg ggttctgggg      600
```

| | |
|---|---|
| gcacaatcgg gtcccgtctc tcatccctaa ccagactcca aaagacaccc ccgctcccac | 660 |
| agaacccacc taccctctac cctctatcct tgcccttgca ggtcttgccc cagaagctgc | 720 |
| gggcacatcc acgcctgaaa tgcggcgctc agtcctggtc aggaacccag gccacaaagg | 780 |
| cctgagaccc gtttatgaag agctcgactc tgactccgag gacctagacc ccaatcctga | 840 |
| agatctggac ccggtttctg aagacccaga gcctgatcct gaagacctca cactgtccc | 900 |
| ggaagacgtg gacccagct atgaagatct ggagcccgtc tcggaggatc tggacccga | 960 |
| cgccgaagct ccgggctcgg aaccccaaga tcccgacccc | 1000 |

<210> SEQ ID NO 22
<211> LENGTH: 1000
<212> TYPE: DNA
<213> ORGANISM: H. Sapiens

<400> SEQUENCE: 22

| | |
|---|---|
| ggaacatttc ccaaggaggg aagggagggt tctagggcag gggccgcggg gcactcctgg | 60 |
| ggcaggtgtg gaggagactg gggtcttcgt gggtggtatt tgtcatgggt gggggggggg | 120 |
| actccctcta ctgggttagg tccctaaact ggagctggac caagctccgg agtaccccac | 180 |
| ccccaggcta tccaaggctc cttccactgg agttgccttt gcagccaggt tgggctagcc | 240 |
| aggagccagg ctaggagccc agggtctgag cgggtgttga cagcctggag tgggtgggcg | 300 |
| gactgtgtgg gaggtgggtg ctggaggatg gcagggggga acaggagggg gaagaaggag | 360 |
| gggtaggggg ctggagcagg aaatgggggg caaacaggag ggggtgcggg aggggcgca | 420 |
| gaaggaggag gggcccagca ggaggggtg cagaaagggc aggggttcca gcaggagggg | 480 |
| gttcataggg gcaggggggc ccagcaggag ggggtgcagg aagggtgggg gggtgcagga | 540 |
| ggggtgaggg gttccagcag aagggcgtgc aggagggca ggggctgga gcaggagtgg | 600 |
| ggggtcgggg aaggggacaa gaggggaggc ggggaggggg ccgggagggg cggggagggc | 660 |
| ggggagttcc agcaggaggg gcaggggct ggagcaggag ggggtgcagg agactgagcg | 720 |
| gggattcgcg ggctctgcga tggtcgggag cgcaggcagc gaaagccccg cgtcccgggt | 780 |
| cgcggcggtc agacagacgc agcctgggtt gggtccctg caggaagtcg ccgcgggcca | 840 |
| acttttcgtg gggccgcggg gcaagcaggt gaagtcacgt ggcccgggcg gggcggggcg | 900 |
| gctcggtcgg accccgcccc tgcctccaag tcccgtggcg tcggcggag cggcgcagcg | 960 |
| cgggccgggc cgggacgggg actgtcggct gcaggcggcc | 1000 |

<210> SEQ ID NO 23
<211> LENGTH: 1000
<212> TYPE: DNA
<213> ORGANISM: H. Sapiens

<400> SEQUENCE: 23

| | |
|---|---|
| cccgtctcta ctaaacatac aaaattagtc gggtgtgctg gagggtgcct gtaatcccaa | 60 |
| ctactctgga ggctgaggcg ggagaattgc ttgaacctgg aaggcggagg ttgtggtgag | 120 |
| ccgagatcgt gccattgcac tccagcctgg gcgacaagag tgaaaactcc gtctcaaaaa | 180 |
| aaaaaaaga atgtggctg gtatctcggt gtctgtctat aggtgtgggt ctggatgtgg | 240 |
| gtctggatgt gggtctgtgc ccttggatgg ggcgtgtctg aaggcatttg ctatatgctc | 300 |
| agctgtggac ctataagtgt gttggacatc agagttgtga ctgtctccgg gtgtgtgtgt | 360 |
| gtgtgtgtgt gctgtaagtg tacaacagaa agcatttgag tatctgtgta tattcaagtg | 420 |
| tcaagtgcct ggatgtgtgt gggtgtccct ggaaggtgtg tctcagggtg tttgtacatc | 480 |

```
tgtgagtgta aagtggatgt gtgtttctgt ctctgggtgt gtccatggag gggatgggtc      540
ctgatgggga cagcccacct aggttctggc tgaggcccat gggctctgat gccccttta      600 taccccccca cccccagcac cacctgacat cccatgcagc ctgccagtgc tgcagtgagc      660
acacacgcac acacacgggt gcacacacag agctccgcag cctcctcctg ggacccttgc      720 cctgccccc tcccatgggc acggacccc caccgcctcc acccactgcc gcgggggggc       780 ccgttgggc ccagggctgg cgggccatgt aaccagggct gctgctggga gcgcggaggg       840
gaagggagcc cccagccctg ctgggccggc ccaggcccct ccgcggctcc cccttccact      900
acccacctgc ccggcacccc ctccccagtg gttgttaacc ccgggactcc ccaagcccag      960
cctctgtgtg cagcagcccc aggcgggcta agtctccaag                           1000
```

<210> SEQ ID NO 24
<211> LENGTH: 1000
<212> TYPE: DNA
<213> ORGANISM: H. Sapiens

<400> SEQUENCE: 24

```
ggcagtcaag gggtggaagg acccctgcat acaaatttgt aggtgttact gaagagtcgg       60
tacacaggct cagtgcttct aaattatgtt tctctgtttt ggtttgggtg atgagttgtt      120
gatatgataa agtgatttgt tgcactgact ctggagccag agtgcctgtg gttgaaatcc      180
cacctccacc acttaatacc tgcttgatct tagttaagtt acgtaatctc tctgtgcttc      240
atcctcctta tctgtaaaag ggactagggg atagagaagg ctgtcacata gtgatatgga      300
agtggttttc tttccttcct tccttctctc tctctctctt tctttctttc tgtcttttta      360 aaattttat agagacaagg tctgcctatg ttgctcaggc tggtctcgaa cgcctggcct       420
caagcaatcc tcccacctca gcctcccaaa gtgctaagat tataggcgtg agccaccgcg      480
cccagccatg tttactattt ccactagatt gtcatctcca tgaggttgag gttttctatt      540
ttgtttaggg ctgtctactc agagcctggc acaaagcatg tgctcaacga aaatttcctg      600
aatgagtaaa ttggggtgaa attcttggga gaggggctca ggggctgga atccctattc       660 ctgcgtggga ctccgggcca ctgggcgcg tcctggggtc tggggaaggg cctcccctg        720 cgccgagagc gtgcccgggc gggcgcggtc caggcgctga gccctgggg cgctcccgtg       780 gctcctcccc cggcgggcgt gtagtgtcgg cccagcgact gcgggaggca tcccggagcc      840
ggccgggcgg ggcggagtcg acgctcggcc cggcctctgc tcacctcatc cacgggagac      900
ggaagtcttg gcctgctcc gctccccga gaatcgggcc tcgccctgct gggcggctgg        960
acctgggcaa agcctgggcg cgctcccgcg cagcggcgcc                           1000
```

<210> SEQ ID NO 25
<211> LENGTH: 1000
<212> TYPE: DNA
<213> ORGANISM: H. Sapiens

<400> SEQUENCE: 25

```
tagtagagat ggggttttac catgttgacc aggctggtct tgatctcctg gcctcatgat       60
ccacccacct cggcctccca agtgttggg attacaggcg tgagccacca tgcctggcct       120
atatgttctt ttaatgcctt taccattatt ctgtggagtc ttgggaagga gaggaaataa      180
atgcatgttt ttatttgcca tctttaattg gactgcttaa tgtaaaactg ttcgtgttat      240
aaattccccc tcatatattt ggttttgtga ctgcagtagt gtaaattctc tgcctagaat      300
```

-continued

```
tttaaagaaa gtgattctgt atgtgattag ggagtaaggt tcagataacc ttgagtggtt    360
taaagtttcc tactgagtaa tctgaacaag gcggatttaa gatactgcag acagagtgtg    420
agaataactc tctcttcaca acttaagaag cctggttcct tatttacaac tgggataaga    480
taaatggttg aatacctaga gaagttccac aaaaagttac acaaaaagtt tagttaaatt    540
taagttaaaa gttagttaaa atgaaaagtt aagttttat tctgctacta aaccatgctc    600
ctctgcgtgt ctgaaccttc aggttcctct agatttctag cacctgaaag aaaacaaaac    660
tgcagcatca gccaggtagg cctctcctaa tcttactcat tcacagagaa tttcccctttt   720 gagtcaccat ggcattggct ggttactcat accacagatc cctcaggatt ggctgggact    780
gcaaataaaa tactgtttgc ccataatcaa gttgataagc tacaacataa acacatctag    840
gttcttgttc ttagaataca gcatgaagaa tttgctttct tctttcttcc taacatttttc   900 atgtgagatc cagaaaggac acattgtctc tggccattcg aagaaagaaa gaaagaaaaa    960 aaaaaaggt atttagagac agagagagaa aaaggctgaa                           1000
```

<210> SEQ ID NO 26
<211> LENGTH: 21
<212> TYPE: RNA
<213> ORGANISM: H. Sapiens
<400> SEQUENCE: 26
ugugauuucc aauaauugag g                                              21

<210> SEQ ID NO 27
<211> LENGTH: 18
<212> TYPE: RNA
<213> ORGANISM: H. Sapiens
<400> SEQUENCE: 27
uggagagaaa ggcaguuc                                                  18

<210> SEQ ID NO 28
<211> LENGTH: 22
<212> TYPE: RNA
<213> ORGANISM: H. Sapiens
<400> SEQUENCE: 28
aaggagcuca cagucuauug ag                                             22

<210> SEQ ID NO 29
<211> LENGTH: 21
<212> TYPE: RNA
<213> ORGANISM: H. Sapiens
<400> SEQUENCE: 29
ugcuuucccu ccuuccuucu u                                              21

<210> SEQ ID NO 30
<211> LENGTH: 22
<212> TYPE: RNA
<213> ORGANISM: H. Sapiens
<400> SEQUENCE: 30
agccaggugc cuucaccugc uu                                             22

<210> SEQ ID NO 31
<211> LENGTH: 21
<212> TYPE: RNA
<213> ORGANISM: H. Sapiens

```
<400> SEQUENCE: 31
uuaaagugga uguguguuau u                                              21

<210> SEQ ID NO 32
<211> LENGTH: 21
<212> TYPE: RNA
<213> ORGANISM: H. Sapiens

<400> SEQUENCE: 32
ucagucuuuu ucucucuccu a                                              21

<210> SEQ ID NO 33
<211> LENGTH: 16
<212> TYPE: DNA
<213> ORGANISM: H. Sapiens

<400> SEQUENCE: 33
tggagagaaa ggcagt                                                    16

<210> SEQ ID NO 34
<211> LENGTH: 20
<212> TYPE: DNA
<213> ORGANISM: H. Sapiens

<400> SEQUENCE: 34
caatagacgg tgagctcctt                                                20

<210> SEQ ID NO 35
<211> LENGTH: 18
<212> TYPE: DNA
<213> ORGANISM: H. Sapiens

<400> SEQUENCE: 35
aagaaggagg aaggaaag                                                  18

<210> SEQ ID NO 36
<211> LENGTH: 20
<212> TYPE: DNA
<213> ORGANISM: H. Sapiens

<400> SEQUENCE: 36
agcaggtgaa gtcacgtggc                                                20

<210> SEQ ID NO 37
<211> LENGTH: 17
<212> TYPE: DNA
<213> ORGANISM: H. Sapiens

<400> SEQUENCE: 37
taaagtggat gtgtgtt                                                   17

<210> SEQ ID NO 38

<400> SEQUENCE: 38

000

<210> SEQ ID NO 39

<400> SEQUENCE: 39

000
```

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<211> LENGTH: 22
<212> TYPE: RNA
<213> ORGANISM: H. Sapiens

<400> SEQUENCE: 43
uagguaguuu cauguuguug gg                                          22

<210> SEQ ID NO 44
<211> LENGTH: 22
<212> TYPE: RNA
<213> ORGANISM: H. Sapiens

<400> SEQUENCE: 44
aagcugccag uugaagaacu gu                                          22

<210> SEQ ID NO 45
<211> LENGTH: 22
<212> TYPE: RNA
<213> ORGANISM: H. Sapiens

<400> SEQUENCE: 45
uucaacgggu auuuauugag ca                                          22

<210> SEQ ID NO 46
<211> LENGTH: 21
<212> TYPE: RNA
<213> ORGANISM: H. Sapiens

<400> SEQUENCE: 46
agccaggugc cuucaccugc u                                           21

<210> SEQ ID NO 47
<211> LENGTH: 22
<212> TYPE: RNA
<213> ORGANISM: H. Sapiens

<400> SEQUENCE: 47
caacggaauc ccaaaagcag cu                                          22

<210> SEQ ID NO 48
<211> LENGTH: 23
<212> TYPE: RNA
<213> ORGANISM: H. Sapiens

<400> SEQUENCE: 48
ucuuugguua ucuagcugua uga                                    23

<210> SEQ ID NO 49
<211> LENGTH: 21
<212> TYPE: RNA
<213> ORGANISM: H. Sapiens

<400> SEQUENCE: 49
ugauugucca aacgcaauuc u                                      21

<210> SEQ ID NO 50
<211> LENGTH: 22
<212> TYPE: RNA
<213> ORGANISM: H. Sapiens

<400> SEQUENCE: 50
uguaguguuu ccuacuuuau gg                                     22

<210> SEQ ID NO 51
<211> LENGTH: 24
<212> TYPE: DNA
<213> ORGANISM: Artificial Sequence
<220> FEATURE:
<223> OTHER INFORMATION: PCR Primer

<400> SEQUENCE: 51
cggcatgaag acagactcgc ttag                                   24

<210> SEQ ID NO 52
<211> LENGTH: 24
<212> TYPE: DNA
<213> ORGANISM: Artificial Sequence
<220> FEATURE:
<223> OTHER INFORMATION: PCR Primer

<400> SEQUENCE: 52
cggtatgaag atagattcgt ttag                                   24

<210> SEQ ID NO 53
<211> LENGTH: 25
<212> TYPE: DNA
<213> ORGANISM: Artificial Sequence
<220> FEATURE:
<223> OTHER INFORMATION: PCR Primer

<400> SEQUENCE: 53
tggtatgaag atagatttgt ttagt                                  25

<210> SEQ ID NO 54
<211> LENGTH: 24
<212> TYPE: DNA
<213> ORGANISM: Artificial Sequence
<220> FEATURE:
<223> OTHER INFORMATION: PCR Primer

<400> SEQUENCE: 54
catgcacaag tccgctgaga cccg                                   24

<210> SEQ ID NO 55
<211> LENGTH: 21
<212> TYPE: DNA
<213> ORGANISM: Artificial Sequence
<220> FEATURE:
<223> OTHER INFORMATION: PCR Primer

<400> SEQUENCE: 55
acacaaatcc gctaaaaccc g                                           21

<210> SEQ ID NO 56
<211> LENGTH: 24
<212> TYPE: DNA
<213> ORGANISM: Artificial Sequence
<220> FEATURE:
<223> OTHER INFORMATION: PCR Primer

<400> SEQUENCE: 56
catacacaaa tccactaaaa ccca                                        24

<210> SEQ ID NO 57
<211> LENGTH: 22
<212> TYPE: DNA
<213> ORGANISM: Artificial Sequence
<220> FEATURE:
<223> OTHER INFORMATION: PCR Primer

<400> SEQUENCE: 57
ttgctgggcg ctgtggttca cg                                          22

<210> SEQ ID NO 58
<211> LENGTH: 20
<212> TYPE: DNA
<213> ORGANISM: Artificial Sequence
<220> FEATURE:
<223> OTHER INFORMATION: PCR Primer

<400> SEQUENCE: 58
gttgggcgtt gtggtttacg                                             20

<210> SEQ ID NO 59
<211> LENGTH: 22
<212> TYPE: DNA
<213> ORGANISM: Artificial Sequence
<220> FEATURE:
<223> OTHER INFORMATION: PCR Primer

<400> SEQUENCE: 59
ttgttgggtg ttgtggttta tg                                          22

<210> SEQ ID NO 60
<211> LENGTH: 24
<212> TYPE: DNA
<213> ORGANISM: Artificial Sequence
<220> FEATURE:
<223> OTHER INFORMATION: PCR Primer

<400> SEQUENCE: 60
tcccagaacc tgcgagttac gtat                                        24

<210> SEQ ID NO 61
<211> LENGTH: 23
<212> TYPE: DNA
<213> ORGANISM: Artificial Sequence
<220> FEATURE:
<223> OTHER INFORMATION: PCR Primer

<400> SEQUENCE: 61
tcccaaaacc tacgaattac gta                                         23

<210> SEQ ID NO 62
<211> LENGTH: 24
<212> TYPE: DNA

```
<213> ORGANISM: Artificial Sequence
<220> FEATURE:
<223> OTHER INFORMATION: PCR Primer

<400> SEQUENCE: 62
tcccaaaacc tacaaattac atat                                              24

<210> SEQ ID NO 63
<211> LENGTH: 23
<212> TYPE: DNA
<213> ORGANISM: Artificial Sequence
<220> FEATURE:
<223> OTHER INFORMATION: PCR Primer

<400> SEQUENCE: 63
acgcctgaaa tgcggcgctc agt                                               23

<210> SEQ ID NO 64
<211> LENGTH: 22
<212> TYPE: DNA
<213> ORGANISM: Artificial Sequence
<220> FEATURE:
<223> OTHER INFORMATION: PCR Primer

<400> SEQUENCE: 64
acgtttgaaa tgcggcgttt ag                                                22

<210> SEQ ID NO 65
<211> LENGTH: 24
<212> TYPE: DNA
<213> ORGANISM: Artificial Sequence
<220> FEATURE:
<223> OTHER INFORMATION: PCR Primer

<400> SEQUENCE: 65
atgtttgaaa tgtggtgttt agtt                                              24

<210> SEQ ID NO 66
<211> LENGTH: 24
<212> TYPE: DNA
<213> ORGANISM: Artificial Sequence
<220> FEATURE:
<223> OTHER INFORMATION: PCR Primer

<400> SEQUENCE: 66
tccaaatcct ccaaaacaaa ctcc                                              24

<210> SEQ ID NO 67
<211> LENGTH: 21
<212> TYPE: DNA
<213> ORGANISM: Artificial Sequence
<220> FEATURE:
<223> OTHER INFORMATION: PCR Primer

<400> SEQUENCE: 67
caaatcctcc gaaacgaact c                                                 21

<210> SEQ ID NO 68
<211> LENGTH: 22
<212> TYPE: DNA
<213> ORGANISM: Artificial Sequence
<220> FEATURE:
<223> OTHER INFORMATION: PCR Primer

<400> SEQUENCE: 68
caaatcctcc aaaacaaact cc                                                22
```

```
<210> SEQ ID NO 69
<211> LENGTH: 22
<212> TYPE: DNA
<213> ORGANISM: Artificial Sequence
<220> FEATURE:
<223> OTHER INFORMATION: PCR Primer

<400> SEQUENCE: 69
cgatggtcgg gagcgcaggc ag                                              22

<210> SEQ ID NO 70
<211> LENGTH: 18
<212> TYPE: DNA
<213> ORGANISM: Artificial Sequence
<220> FEATURE:
<223> OTHER INFORMATION: PCR Primer

<400> SEQUENCE: 70
cgatggtcgg gagcgtag                                                   18

<210> SEQ ID NO 71
<211> LENGTH: 21
<212> TYPE: DNA
<213> ORGANISM: Artificial Sequence
<220> FEATURE:
<223> OTHER INFORMATION: PCR Primer

<400> SEQUENCE: 71
tgatggttgg gagtgtaggt a                                               21

<210> SEQ ID NO 72
<211> LENGTH: 22
<212> TYPE: DNA
<213> ORGANISM: Artificial Sequence
<220> FEATURE:
<223> OTHER INFORMATION: PCR Primer

<400> SEQUENCE: 72
gcagccgaca gtccccgtcc cg                                              22

<210> SEQ ID NO 73
<211> LENGTH: 18
<212> TYPE: DNA
<213> ORGANISM: Artificial Sequence
<220> FEATURE:
<223> OTHER INFORMATION: PCR Primer

<400> SEQUENCE: 73
ccgacaatcc ccgtcccg                                                   18

<210> SEQ ID NO 74
<211> LENGTH: 22
<212> TYPE: DNA
<213> ORGANISM: Artificial Sequence
<220> FEATURE:
<223> OTHER INFORMATION: PCR Primer

<400> SEQUENCE: 74
acaaccaaca atccccatcc ca                                              22

<210> SEQ ID NO 75
<211> LENGTH: 17
<212> TYPE: DNA
<213> ORGANISM: Artificial Sequence
<220> FEATURE:
```

```
<223> OTHER INFORMATION: PCR Primer

<400> SEQUENCE: 75
cgggccactg ggcggcg                                                    17

<210> SEQ ID NO 76
<211> LENGTH: 17
<212> TYPE: DNA
<213> ORGANISM: Artificial Sequence
<220> FEATURE:
<223> OTHER INFORMATION: PCR Primer

<400> SEQUENCE: 76
cgggttattg ggcggcg                                                    17

<210> SEQ ID NO 77
<211> LENGTH: 22
<212> TYPE: DNA
<213> ORGANISM: Artificial Sequence
<220> FEATURE:
<223> OTHER INFORMATION: PCR Primer

<400> SEQUENCE: 77
gattttgggt tattgggtgg tg                                              22

<210> SEQ ID NO 78
<211> LENGTH: 17
<212> TYPE: DNA
<213> ORGANISM: Artificial Sequence
<220> FEATURE:
<223> OTHER INFORMATION: PCR Primer

<400> SEQUENCE: 78
actccgcccc gcccggc                                                    17

<210> SEQ ID NO 79
<211> LENGTH: 18
<212> TYPE: DNA
<213> ORGANISM: Artificial Sequence
<220> FEATURE:
<223> OTHER INFORMATION: PCR Primer

<400> SEQUENCE: 79
actccgcccc gcccgacc                                                   18

<210> SEQ ID NO 80
<211> LENGTH: 22
<212> TYPE: DNA
<213> ORGANISM: Artificial Sequence
<220> FEATURE:
<223> OTHER INFORMATION: PCR Primer

<400> SEQUENCE: 80
actccacccc acccaaccaa ct                                              22

<210> SEQ ID NO 81
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 81
cctcaattat tggaaatcac a                                               21
```

```
<210> SEQ ID NO 82
<211> LENGTH: 18
<212> TYPE: DNA
<213> ORGANISM: Artificial Sequence
<220> FEATURE:
<223> OTHER INFORMATION: synthetic oligomeric compound

<400> SEQUENCE: 82
gaactgcctt tctctcca                                              18

<210> SEQ ID NO 83
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 83
ctcaatagac tgtgagctcc tt                                         22

<210> SEQ ID NO 84
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 84
aagaaggaag gagggaaagc a                                          21

<210> SEQ ID NO 85
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 85
agcaggtgaa ggcacctggc t                                          21

<210> SEQ ID NO 86
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 86
aataacacac atccacttta a                                          21

<210> SEQ ID NO 87
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 87
taggagagag aaaaagactg a                                          21

<210> SEQ ID NO 88
<211> LENGTH: 20
<212> TYPE: DNA
<213> ORGANISM: Artificial Sequence
<220> FEATURE:
<223> OTHER INFORMATION: synthetic oligomeric compound
```

-continued

<400> SEQUENCE: 88
gcttttagaa ccactgcctc						20

<210> SEQ ID NO 89
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 89
cctggggagg ggaccatcag						20

<210> SEQ ID NO 90
<211> LENGTH: 20
<212> TYPE: DNA
<213> ORGANISM: Artificial Sequence
<220> FEATURE:
<223> OTHER INFORMATION: PCR Primer

<400> SEQUENCE: 90
acagcggttt ctctggatgt						20

<210> SEQ ID NO 91
<211> LENGTH: 20
<212> TYPE: DNA
<213> ORGANISM: Artificial Sequence
<220> FEATURE:
<223> OTHER INFORMATION: PCR Primer

<400> SEQUENCE: 91
cagaacgctg gactcttgct						20

<210> SEQ ID NO 92
<211> LENGTH: 22
<212> TYPE: DNA
<213> ORGANISM: Artificial Sequence
<220> FEATURE:
<223> OTHER INFORMATION: PCR Probe

<400> SEQUENCE: 92
gcgatggaaa tgtgttcctg cc					22

<210> SEQ ID NO 93
<211> LENGTH: 20
<212> TYPE: DNA
<213> ORGANISM: Artificial Sequence
<220> FEATURE:
<223> OTHER INFORMATION: PCR Primer

<400> SEQUENCE: 93
ggagccatgg gatctactga						20

<210> SEQ ID NO 94
<211> LENGTH: 20
<212> TYPE: DNA
<213> ORGANISM: Artificial Sequence
<220> FEATURE:
<223> OTHER INFORMATION: PCR Primer

<400> SEQUENCE: 94
ctgattcagc cccattctgt						20

<210> SEQ ID NO 95
<211> LENGTH: 22

```
<212> TYPE: DNA
<213> ORGANISM: Artificial Sequence
<220> FEATURE:
<223> OTHER INFORMATION: PCR Probe

<400> SEQUENCE: 95
ccactgtggt gtgctctcca gc                                              22

<210> SEQ ID NO 96
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 96
caatgcactc agcttaagtg                                                 20

<210> SEQ ID NO 97
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 97
gtcaagctgg ccacattgct                                                 20

<210> SEQ ID NO 98
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 98
gaaatcacaa tgcactcagc                                                 20

<210> SEQ ID NO 99
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 99
ctggccacat tgctcttttc                                                 20

<210> SEQ ID NO 100
<211> LENGTH: 1193
<212> TYPE: DNA
<213> ORGANISM: H. Sapiens

<400> SEQUENCE: 100
tctagaaaaa ttttttaaaa aattaggccg ctcgagcgag agtgcagtgg ctcacgcctg      60
taatccaaca cttcaggagg ctgaagaggg tggatcacct gaggtcagga gttccagacc     120
agcctggcca acatggtgaa accccgtctt gtactaaaaa tacaaaatta gccggtgtgg     180
tggcacacgc ctgtagtccc agctactcaa taggctgaga caggagagtc tcttgaaccc     240
ggcaggcgga ggttgcagtg agccgagatc gtgccactgc actccagcct gggcaagaca     300
gagcgagact ccgtctcaaa aaatacaaac aaaacaaaca aacaaaaaat taggctgcta     360
gctcagtggc tcatggctca cacctgaaat cctagcactt tgggaggcca aggcaggagg     420
```

```
atcgcttcag cccaggagtt cgagaccagg ctgggcaata cagggagaca cagcgccccc      480
actgcccctg tccgccccga cttgtctctc tacaaaaagg caaagaaaaa aaaaaattag      540
cctggcgtgg tggtgtgcac ctgtactccc agctactaga gaggctgggg ccagaggacc      600
gcttgagccc aggagttcga ggctgcagtg agctgtgatc gcaccactgc actccagctt      660
gggtgaaaga gtgagcccca tctccaaaac gaacaaacaa aaatcccaa aaacaaaag       720 aactcagcca agtgtaaaag ccctttctga tcccaggtct tagtgagcca ccggcgggc       780 tgggattcga acccagtgga atcagaaccg tgcaggtccc ataacccacc tagaccctag      840
caactccagg ctagagggtc accgcgtcta tgcgaggccg ggtgggcggg ccgtcagctc      900
cgccctgggg aggggtccgc gctgctgatt ggctgtggcc ggcaggtgaa ccctcagcca      960
atcagcggta cgggggggcgg tgctccgggg ctcacctggc tgcagccacg caccccctct    1020
cagtggcgtc ggaactgcaa agcacctgtg agcttgcgga agtcagttca gactccagcc    1080
cgctccagcc cggcccgacc cgaccgcacc cggcgcctgc cctcgctcgg cgtccccggc    1140
cagccatggg cccttggagc cgcagcctct cggcgctgct gctgctgctg cag            1193

<210> SEQ ID NO 101
<211> LENGTH: 255
<212> TYPE: DNA
<213> ORGANISM: H. Sapiens

<400> SEQUENCE: 101
agcagacggg agtttctcct cggggtcgga gcaggaggca cgcggagtgt gaggccacgc       60
atgagcggac gctaaccccc tccccagcca caaagagtct acatgtctag ggtctagaca      120
tgttcagctt tgtggacctc cggctcctgc tcctcttagc ggccaccgcc ctcctgacgc      180
acggccaaga ggaaggccaa gtcgagggcc aagacgaaga catcccacca atcacctgcg      240
tacagaacgg cctca                                                      255

<210> SEQ ID NO 102
<211> LENGTH: 255
<212> TYPE: DNA
<213> ORGANISM: H. Sapiens

<400> SEQUENCE: 102
gaattcgcgg ccgcgtcgac cgcttctgtg gccacggcag atgaaacaga aaggctaaag       60
agggctggag tcaggggact tctcttccac cagcttcacg gtgatgatat ggcatctgcc      120
agctctagcc gggcaggagt ggccctgcct tttgagaagt ctcagctcac tttgaaagtg      180
gtgtccgcaa agcccaaggt gcataatcgt caacctcgaa ttaactccta cgtggaggtg      240
gcggtggatg gactc                                                      255

<210> SEQ ID NO 103
<211> LENGTH: 255
<212> TYPE: DNA
<213> ORGANISM: H. Sapiens

<400> SEQUENCE: 103
caggcggcgg ggatggggcc gccgctcccg ctgctgctgc tgctactgct gctgctgccg       60
ccacgcgtcc tgcctgccgc cccttcgtcc gtccccgcg gccggcagct cccggggcgt      120
ctgggctgcc tgctcgagga gggcctctgc ggagcgtccg aggcctgtgt gaacgatgga      180
gtgtttggaa ggtgccagaa ggttccggca atggactttt accgctacga ggtgtcgccc      240
gtggccctgc agcgc                                                      255
```

```
<210> SEQ ID NO 104
<211> LENGTH: 255
<212> TYPE: DNA
<213> ORGANISM: H. Sapiens

<400> SEQUENCE: 104
cagcccctct ggcaggctcc cgccagcgtc gctgcggctc cggcccggga gcgagcgccc        60
ggagctcgga aagatgcggc gcccgcgcg gcctgggggt ctcggggat ccggggtct         120 ccggctgctc ctctgcctcc tgctgctgag cagccgcccg gggggctgca cgccgttag       180 tgcccacggc tgtctatttg accgcaggct ctgctctcac ctggaagtct gtattcagga     240
tggcttgttt gggca                                                      255

<210> SEQ ID NO 105
<211> LENGTH: 255
<212> TYPE: DNA
<213> ORGANISM: H. Sapiens

<400> SEQUENCE: 105
ctccagacct acccagaaag atgcccggat ggatcctgca gctccgtggc ttttctggga       60
agcagcggcc cctgctctca agagaccctg gctcctgatg gtggcccaa ggttgccagc      120 tggtgctagg gactcaggac agtttcccag aaaaggccaa gcgggcagcc cctccagggg     180
ccgggtgagg aagctggggg gtgcggaggc cacactgggt ccctgaaccc cctgcttggt    240
tacagtgcag ctcct                                                       255

<210> SEQ ID NO 106
<211> LENGTH: 255
<212> TYPE: DNA
<213> ORGANISM: H. Sapiens

<400> SEQUENCE: 106
taacgaggaa cttttcgccg gcgccgggcc gcctctgagg ccagggcagg acacgaacgc       60
gcggagcggc ggcggcgact gagagccggg gccgcggcgg cgctccctag gaagggccgt     120
acgaggcggc gggcccggcg ggcctccggg aggaggcggc tgcgccatgg acgagccacc    180
cttcagcgag gcggctttgg agcaggcgct gggcgagccg tgcgatctgg acgcggcgct   240
gctgaccgac atcga                                                      255

<210> SEQ ID NO 107
<211> LENGTH: 255
<212> TYPE: DNA
<213> ORGANISM: H. Sapiens

<400> SEQUENCE: 107
ctcctcacag aagcctggag ctgggcatcc aagaagaagc agcctcattt gttttctggt       60
gtcatcgtag gtggccacct atggcttttg ggaatgtaaa aagggcagct ctctggcatg     120
ttcctgactg aggatctcat aacatttaac ttgaggaact tcctccttt ccagctttgg     180 gagtcaagct tctcacctgg ggcgggtggg ttctgcacca ccctcccacc ctccttcctc   240
cgtgtggacg ataga                                                      255

<210> SEQ ID NO 108
<211> LENGTH: 255
<212> TYPE: DNA
<213> ORGANISM: H. Sapiens
```

<400> SEQUENCE: 108

```
acgcgtccgg ggaaacggtg caaacggcgt ggccgccatc ttgcttgtgc ccccgcttcg    60
cgcgcgctcc gtgacgcaca cttccccccT ccccTccgcc gcgcctgggc tctgcattg    120
cccgactccg taggagcgcg ggggcggctc ctgctcttcc tggactcctg agcagagttg   180
tcgagatgtc cacagaagga ggatttggtg gtactagcag cagtgatgcc cagcaaagtc   240
tacagtcgtt ctggc                                                    255
```

<210> SEQ ID NO 109
<211> LENGTH: 255
<212> TYPE: DNA
<213> ORGANISM: H. Sapiens

<400> SEQUENCE: 109

```
ccgtcggtga ggcggtgccg ggcgggggtt gtcgggtgtc atgggcggtg gcgacggcac    60
cgccccgcg tctccctgag cgggacggca gggggggctt ctgcgctgag ccgggcgatg    120
gacgacagcg gcgagctggg tggtctggag accatgagaa ccctcacgga gctgggcgac   180
gagctgaccc tgggagacat cgacgagatg ctgcaatttg tcagtaatca agtgggagag   240
ttccctgact tgttt                                                    255
```

<210> SEQ ID NO 110
<211> LENGTH: 255
<212> TYPE: DNA
<213> ORGANISM: H. Sapiens

<400> SEQUENCE: 110

```
ccgcctggag gcacaggcca tgagggctc tcaggaggtg ctgctgatgt ggcttctggt    60
gttggcagtg ggcggcacag agcacgccta ccggcccggc cgtagggtgt gtgctgtccg   120
ggctcacggg gatcctgtct ccgagtcgtt cgtgcagcgt gtgtaccagc ccttcctcac   180
cacctgcgac gggcaccggg cctgcagcac ctaccgaacc atctatagga ccgcctaccg   240
ccgcagccct gggct                                                    255
```

<210> SEQ ID NO 111
<211> LENGTH: 255
<212> TYPE: DNA
<213> ORGANISM: H. Sapiens

<400> SEQUENCE: 111

```
gacgtttcgc gccaatttcg gttggccggc cacagtccac cgcgcggaga ttctcagctt    60
ccccaggagc aagacctctg agcccgccaa gcgcggccgc acggccctcg gcagcgatgg   120
cactgaagga ctacgcgcta gagaaggaaa aggttaagaa gttcttacaa gagttctacc   180
aggatgatga actcgggaag aagcagttca agtatgggaa ccagttggtt cggctggctc   240
atcgggaaca ggtgg                                                    255
```

<210> SEQ ID NO 112
<211> LENGTH: 255
<212> TYPE: DNA
<213> ORGANISM: H. Sapiens

<400> SEQUENCE: 112

```
cagcagagct ggattggggt gttgagtcca ggctgagtag ggggcagccc actgctcttg    60
gtccctgtgc ctgctgggg tgccctgccc tgaactccag gcagcgggga cagggcgagg   120
tgccaccTTa gtctggctgg ggaggcggac gatgaggagt gatgggcag gcatgcggcc   180
```

```
actccatcct ctgcaggagc cagcagtacc cggcagcgcg accggctgag ccgcggggcc    240
agcaggtctt cctca                                                     255
```

<210> SEQ ID NO 113
<211> LENGTH: 255
<212> TYPE: DNA
<213> ORGANISM: H. Sapiens

<400> SEQUENCE: 113

```
caacagcatc agcatgctga ccaattacac cttcagtaac atgtctcacc tctccactct    60
gatcctgagc tacaaccggc tgaggtgcat ccccgtccac gccttcaacg ggctgcggtc   120
cctgcgagtg ctaaccctcc atggcaatga catttccagc gttcctgaag ctccttcaa    180 cgacctcaca tctctttccc atctggcgct gggaaccaac ccactccact gtgactgcag   240
tcttcggtgg ctgtc                                                    255
```

<210> SEQ ID NO 114
<211> LENGTH: 255
<212> TYPE: DNA
<213> ORGANISM: H. Sapiens

<400> SEQUENCE: 114

```
ggctgcccga gcgagcgttc ggacctcgca ccccgcgcgc cccgcgccgc cgccgccgcc    60
ggcttttgtt gtctccgcct cctcggccgc cgccgcctct ggaccgcgag ccgcgcgcgc   120
cgggaccttg gctctgccct tcgcggggcgg gaactgcgca ggaccccggcc aggatccgag   180 agaggcgcgg gcgggtggcc gggggcgccg ccggccccgc catggagctc cgggcccgag   240
gctggtggct gctat                                                    255
```

<210> SEQ ID NO 115
<211> LENGTH: 255
<212> TYPE: DNA
<213> ORGANISM: H. Sapiens

<400> SEQUENCE: 115

```
ggcggcgagc ggaatgcagc ggcccgaggc ctggccacgt ccgcacccgg ggaggggggc    60
cgcggcggcc caggccgggg gcccggcgcc gcctgctcga gccggggagc cctcggggct   120
gcggttgcag gaaccttccc tctacaccat caaggctgtt ttcatcctag ataatgacgg   180
gcgccggctg ctggccaagt attatgatga cacattcccc tccatgaagg agcagatggt   240
tttcgagaaa aatgt                                                    255
```

<210> SEQ ID NO 116
<211> LENGTH: 255
<212> TYPE: DNA
<213> ORGANISM: H. Sapiens

<400> SEQUENCE: 116

```
ttttgcggct ccacgtcggc accagctgcg ggcaagatg gaggcgctga ttttggaacc     60
ttccctgtat actgtcaaag ccatcctgat tctggacaat gatggagatc gactttttgc   120
caagtactat gacgacacct accccagtgt caaggagcaa aaggcctttg agaagaacat   180
tttcaacaag acccatcgga ctgacagtga aattgccctc ttggaaggcc tgacagtggt   240
atacaaaagc agtat                                                    255
```

<210> SEQ ID NO 117

```
<211> LENGTH: 255
<212> TYPE: DNA
<213> ORGANISM: H. Sapiens

<400> SEQUENCE: 117
atgtttaacc ctatgtatgc cttgttccgt acctcacctg gtgatcgagt cacctacacc      60
atcaatccat cttcccactg caaccccaac cacctcagct acttcaagtt tgtcggacgc     120
attgtggcca aagctgtata tgacaaccgt cttctggagt gctactttac tcgatccttt     180
tacaaacaca tcttgggcaa gtcagtcaga tatacagata tggagagtga agattaccac     240
ttctaccaag gtctg                                                      255

<210> SEQ ID NO 118
<211> LENGTH: 255
<212> TYPE: DNA
<213> ORGANISM: H. Sapiens

<400> SEQUENCE: 118
atgtcgacca agaatttccg agtcagtgac ggggactgga tttgccctga caaaaaatgt      60
ggaaatgtaa actttgctag aagaaccagc tgtaatcgat gtggtcggga gaaaacaact     120
gaggccaaga tgatgaaagc tgggggcact gaaataggaa agacacttgc agaaaagagc     180
cgaggcctat ttagtgctaa tgactggcaa tgtaaaactt gcagcaatgt gaattgggcc     240
agaagatcag agtgt                                                      255

<210> SEQ ID NO 119
<211> LENGTH: 255
<212> TYPE: DNA
<213> ORGANISM: H. Sapiens

<400> SEQUENCE: 119
cagaattcca ggacaaagag atcttcaaaa atcaaaaatg aggttcacat ttacaagccg      60
gtgcttggca ctgtttcttc ttctaaatca cccaacccca attcttcctg ccttttcaaa     120
tcaaacctat ccaacaatag agcccaagcc atttctttac gtcgtaggac gaaagaagat     180
gatggatgca cagtacaaat gctatgaccg aatgcagcag ttacccgcat accaaggaga     240
aggtccatat tgcaa                                                      255

<210> SEQ ID NO 120
<211> LENGTH: 255
<212> TYPE: DNA
<213> ORGANISM: H. Sapiens

<400> SEQUENCE: 120
tccgggtatg gatgtcaatc ttttgtctac aatgtgaata catttatcct tcggggacca      60
tcaagacttt caggaaaggc cccgcctgtc tctgcgcggc cactttgctg ggacaaaggt     120
caactgaaga agtgggcagg cccgaggcag gagagatgct gaggagtcca tgtgcagggg     180
agggaaaggg agaggcagtc agggagagga ggaggaggta ccgccagaag gggatcctcc     240
cgctccgaaa accag                                                      255

<210> SEQ ID NO 121
<211> LENGTH: 255
<212> TYPE: DNA
<213> ORGANISM: H. Sapiens

<400> SEQUENCE: 121
ggctgaaaga gcctgagctg tgcctctcca ttccactgct gtggcagggt cagaaatctt      60
```

```
ggatagagaa aacctttgc aaacgggaat gtatctttgt aattcctagc acgaaagact      120
ctaacaggtg ttgctgtggc cagttcacca accagcatat cccccctctg ccaagtgcaa      180
cacccagcaa aaatgaagag gaaagcaaac aggtggagac tcagcctgag aaatggtctg      240
ttgccaagca caccc                                                       255

<210> SEQ ID NO 122
<211> LENGTH: 255
<212> TYPE: DNA
<213> ORGANISM: H. Sapiens

<400> SEQUENCE: 122
gaggctgtta atgccaaatg ctcctcactg gagaagacca agcaccggct acagaatgag       60
atagaggact tgatggtgga cgtagagcgc tccaatgctg ctgctgctgc tctggacaag      120
aagcagagga actttgacaa gatcctggcc gagtggaagc agaagtatga ggagtcgcag      180
tctgagctgg agtcctcaca gaaggaggct cgctccctca gcacagagct cttcaagctc      240
aagaacgcct acgag                                                       255

<210> SEQ ID NO 123
<211> LENGTH: 255
<212> TYPE: DNA
<213> ORGANISM: H. Sapiens

<400> SEQUENCE: 123
tgatgtgata tggctgcaag tgcctttgac ccttttgtct cccttccata aactgaaata       60
cctaagctgc tccaacctcc tttttgtctt ttgtttcata aatcctttcc cattgcacat      120
caactcctgt ctctctttgt actgtcactc tcatctgttg cttccattc acactgcctt       180 tagccactca tcattttgtg cctacaccac agaaacctct gaatgtaatg gatgttccta      240
ccagaggaca agtcg                                                       255

<210> SEQ ID NO 124
<211> LENGTH: 255
<212> TYPE: DNA
<213> ORGANISM: H. Sapiens

<400> SEQUENCE: 124
ggcggcggag gcagcagtct tagaatgagt agcaatatcc acgcgaacca tctcagccta       60
gacgcgtcct cctcctcctc ctcctcctct tcctcttctt cttcttcctc ctcctcttcc      120
tcctcgtcct cggtccacga gcccaagatg gatgcgctca tcatcccggt gaccatggag      180
gtgccgtgcg acagccgggg ccaacgcatg tggtgggctt cctggcctc ctccatggtg       240 actttcttcg ggggc                                                       255

<210> SEQ ID NO 125
<211> LENGTH: 255
<212> TYPE: DNA
<213> ORGANISM: H. Sapiens

<400> SEQUENCE: 125
gtcactttta tttgggggtg tggacagctg ctttcccagg ggagtacttc ttacagtggg       60
atttcaagac aagatcggcc tgaagaaaaa ttatatttgt atattttta aaaagtggga      120 actttgaggc tcagagacag agcagaagac agaacctggt cttctgattc cctgtgttct      180
gcttttttca ttgttccact ggacgctcat cagagggaag atcttttttcc tcaattgatt      240
```

```
ccaacaatgt ctcac                                                    255

<210> SEQ ID NO 126
<211> LENGTH: 255
<212> TYPE: DNA
<213> ORGANISM: H. Sapiens

<400> SEQUENCE: 126 gaattcctg tttcagttca ttcatccttc tctcctttcc gctcagactg tagagctcgg      60
tctctccaag tttgtgccta agaagatgat aatcacacaa acaagtcact gttacatgac    120
cagccttggg attcttttcc tgattaatat tctccctgga accactggtc aaggggaatc    180
aagacgacaa gaacccgggg actttgtgaa gcaggacatt ggcgggctgt ctcctaagca    240
tgccccagat attcc                                                    255

<210> SEQ ID NO 127
<211> LENGTH: 255
<212> TYPE: DNA
<213> ORGANISM: H. Sapiens

<400> SEQUENCE: 127
gccagagcgt gagccgcgac ctccgcgcag gtggtcgcgc cggtctccgc ggaaatgttg     60
tccaaagttc ttccagtcct cctaggcatc ttattgatcc tccagtcgag ggtcgaggga   120
cctcagactg aatcaaagaa tgaagcctct tcccgtgatg ttgtctatgg cccccagccc   180
cagcctctgg aaaatcagct cctctctgag gaaacaaagt caactgagac tgagactggg   240
agcagagttg gcaaa                                                    255

<210> SEQ ID NO 128
<211> LENGTH: 255
<212> TYPE: DNA
<213> ORGANISM: H. Sapiens

<400> SEQUENCE: 128
agggattctt ctgcctccac ttcaggtttt agcagcttgg tgctaaattg ctgtctcaaa     60
atgcagagga tctaatttgc agaggaaaac agccaaagaa ggaagaggag gaaaaggaaa   120
aaaaaagggg tatattgtgg atgctctact tttcttggaa atgcaaaaga ttatgcatat   180
ttctgtcctc ctttctcctg ttttatgggg actgattttt ggtgtctctt ctaacagcat   240
acagataggg gggct                                                    255

<210> SEQ ID NO 129
<211> LENGTH: 255
<212> TYPE: DNA
<213> ORGANISM: H. Sapiens

<400> SEQUENCE: 129
tgacgactcc tgagttgcgc ccatgctctt gtcagcttcg ttttaggcgt agcatggcca     60
ggcagaagaa aatggggcaa agcgtgctcc gggcggtctt cttttagtc ctggggcttt    120 tgggtcattc tcacggagga ttccccaaca ccatcagcat aggtggactt ttcatgagaa    180
acacagtgca ggagcacagc gctttccgct tgccgtgca gttatacaac accaaccaga    240
acaccaccga gaagc                                                    255

<210> SEQ ID NO 130
<211> LENGTH: 255
<212> TYPE: DNA
<213> ORGANISM: H. Sapiens
```

<400> SEQUENCE: 130

```
gatgcctgat ctcatcaatc tagcgggaga gacaggataa cctgtccgag agtatagcgc    60
cacttatgac tccgccggaa aaattacttt aaaaatcgcc aaaaattact tggagcaaag   120
ggcagtccgg cggcgttcgc caaggtggcg cagtcggttt tgacctgtag cagagaacca   180
attctggaga acagcctcac ttctttgatt gaatacttac ataatgcatt ggaacatgac   240
atgagattaa ggttt                                                    255
```

<210> SEQ ID NO 131
<211> LENGTH: 255
<212> TYPE: DNA
<213> ORGANISM: H. Sapiens

<400> SEQUENCE: 131

```
cagagcaggg tggagagggc ggtgggaggc gtgtgcctga gtgggctcta ctgccttgtt    60
ccatattatt ttgtgcacat tttccctggc actctgggtt gctagcccccg ccgggcactg   120 ggcctcagac actgcgcggt tccctcggag cagcaagcta agaaagccc ccagtgccgg    180 cgaggaagga ggcggcgggg aaagatgcgc ggcgttggct ggcagatgct gtccctgtcg   240
ctggggttag tgctg                                                    255
```

<210> SEQ ID NO 132
<211> LENGTH: 255
<212> TYPE: DNA
<213> ORGANISM: H. Sapiens
<220> FEATURE:
<221> NAME/KEY: misc_feature
<222> LOCATION: 77, 85
<223> OTHER INFORMATION: n = A,T,C or G

<400> SEQUENCE: 132

```
ctatgatggc cagccaccgc tgagagcacg aagctgctgc tggctggcat ttttctctag    60
cgttgtggtg ccacctnccc ttatnacctt gggacaagaa gggaaggtgg ccattgtctt   120
tctctttgga atcataaagt ggaacagagt ccccagaact catgtggcca tttccgccag   180
catcactccc cggtgcctat ggggtcccgg tgtacctaaa gggagaagga ccccatgtgc   240
tagccagaaa tatac                                                    255
```

<210> SEQ ID NO 133
<211> LENGTH: 255
<212> TYPE: DNA
<213> ORGANISM: H. Sapiens

<400> SEQUENCE: 133

```
atgatgcagg aatctgcgac agagacaata agcaacagtt caatgaatca aaatggaatg    60
agcactctaa gcagccaatt agatgctggc agcagagatg gaagatcaag tggtgacacc   120
agctctgaag taagcacagt agaactgctg catctgcaac aacagcaggc tctccaggca   180
gcaagacaac ttcttttaca gcagcaaaca agtggattga aatctcctaa gagcagtgat   240
aaacagagac cactg                                                    255
```

<210> SEQ ID NO 134
<211> LENGTH: 255
<212> TYPE: DNA
<213> ORGANISM: H. Sapiens

<400> SEQUENCE: 134

```
cgcctagccg cgccggtccc agaagtggcg aaagccgcag ccgagtccag gtcacgccga    60
agccgttgcc cttttaaggg ggagccttga acggcgcct gggttccatg tttgcatccg   120
cctcgcggga aggaaactcc atgttgtaac aaagtttcct ccgcgccccc tccctccccc   180
tcccccctag aacctggctc ccctcccctc cggagctcgc ggggatccct ccctcccacc   240
cctcccctcc ccccc                                                    255

<210> SEQ ID NO 135
<211> LENGTH: 255
<212> TYPE: DNA
<213> ORGANISM: H. Sapiens

<400> SEQUENCE: 135
tttttatttt tttcgagtga aggacccgga gccgaaacac cggtagagcg gggaggtggg    60
tactacacaa ccgtctccag ccttggtctg agtggactgt cctgcagcga ccatgccccg   120
taaaggcacc cagccctcca ctgcccggcg cagagaggaa gggccgccgc cgccgtcccc   180
tgacggcgcc agcagcgacg cggagcctga ccgccgtcc ggccgcacgg agagcccagc   240
caccgccgca gagac                                                    255

<210> SEQ ID NO 136
<211> LENGTH: 255
<212> TYPE: DNA
<213> ORGANISM: H. Sapiens

<400> SEQUENCE: 136
gcgagctgag ctgacagcgc ggagctggcg ctgtggagcg cagggagcct tgccggttcc    60
tccgaccggc gtctgcgagt acagcggcgg ctaacctgcc ccggcttcag gatttacaca   120
gacgtggggc gatgcttgtg accctgcagc tcctcaaacc agcctgtatt gagcggtttg   180
cagcctgatg ctcagccccc tccccacagg gcccctagaa gcctgtttct ccgtacagtc   240
caggacctcc agccc                                                    255

<210> SEQ ID NO 137
<211> LENGTH: 255
<212> TYPE: DNA
<213> ORGANISM: H. Sapiens

<400> SEQUENCE: 137
gagcagcgga cgccggtctc tgttccgcag atggggtttg ttaaagttgt taagaataag    60
gcctacttta agagatacca agtgaaattt agaagacgac gagagggtaa aactgattat   120
tatgctcgga acgcttggt gatacaagat aaaaataaat acaacacacc caaatacagg   180
atgatagttc gtgtgacaaa cagagatatc atttgtcaga ttgcttatgc ccgtatagag   240
ggggatatga tagtc                                                    255

<210> SEQ ID NO 138
<211> LENGTH: 255
<212> TYPE: DNA
<213> ORGANISM: H. Sapiens

<400> SEQUENCE: 138
agggcgctcc aggcgacacg attgcagacg ccattatcct ctgtttctct gctgcaccga    60
cctcgacgtc ttgcctgtgt cccacttgtt cgcggcctat aggctactgc agcactgggg   120
tgtcagttgt tggtccgacc cagaacgctt cagttgtgct ctgcaaggat atataataac   180
tgattggtgt gcccgtttaa taaaagaata tggaaactga acagccagaa gaaaccttcc   240
```

```
ctaacactga aacca                                                     255

<210> SEQ ID NO 139
<211> LENGTH: 255
<212> TYPE: DNA
<213> ORGANISM: H. Sapiens

<400> SEQUENCE: 139
ggagctccaa cctccgctta gagctcgctg cggccgtcct gccccgtgcc ctcggagacc      60
tggaccgtac cacgatgtgg aaacgctggc tcgcgctcgc gctagcgctg gtggcggtcg     120
cctgggtccg cgccgaggaa gagctaagga gcaaatccaa gatctgtgcc aatgtgtttt     180
gtggagctgg ccgggaatgt gcagtcacag agaaagggga acccacctgt ctctgcattg     240
agcaatgcaa acctc                                                    255

<210> SEQ ID NO 140
<211> LENGTH: 255
<212> TYPE: DNA
<213> ORGANISM: H. Sapiens

<400> SEQUENCE: 140
ctccaggcac acgcagcaca cacagcacat gcaccacacg tagcacacac actgcatgca      60
gcacacacac accagaggac gcaccacaca gagcacgcac agcacacacc acacagcgca     120
cgcaccacac agagcacacg cggcacacac agcacacaca gcgcacgcac cacgcagagc     180
acacacggca catgcagcat acacaccaaa cagcgcatgc accacacaga gcacacgcgg     240
cacacgcagc acaca                                                    255

<210> SEQ ID NO 141
<211> LENGTH: 255
<212> TYPE: DNA
<213> ORGANISM: H. Sapiens

<400> SEQUENCE: 141
gcggccgcga gcaacggcag cggcggcggc ggcggcggca tcagcgctgg cggcggcgtc      60
gcttccagca cccccatcaa cgccagcacc ggcagcagca gcagcagcag tagcagcagc     120
agcagcagca gcagtagtag cagcagcagc agtagcagca gcagctgcgg ccccctcccc     180
gggaaacccg tgtactcaac cccgtcccca gtggaaaaca cccctcagaa taatgagtgc     240
aaaatggtgg atctg                                                    255

<210> SEQ ID NO 142
<211> LENGTH: 255
<212> TYPE: DNA
<213> ORGANISM: H. Sapiens

<400> SEQUENCE: 142
cggccagcac accccggcac ctcctctgcg gcagctgcgc ctcgcaagcg cagtgccgca      60
gcgcacgccg gagtggctgt agctgcctcg gcgcggctgc cgccctgcgc gggctgtggg     120
ctgcgggctg cgcccccgct gctggccagc tctgcacggc tgcgggctct gcggcgcccg     180
gtgctctgca acgctgcggc gggcggcatg ggataacgcg gccatggtgc gccgagatcg     240
cctccgcagg atgag                                                    255

<210> SEQ ID NO 143
<211> LENGTH: 255
<212> TYPE: DNA
```

<213> ORGANISM: H. Sapiens

<400> SEQUENCE: 143

```
ggcacgagtg ggagtacagg actcgcctcc tcagggttcc ctgtgctgcc acttttcagc    60
catggccaca agtgaacaga gtatctgcca agcccgggct tccgtgatgg tctacgatga   120
caccagtaag aaatgggtac caatcaaacc tggccagcag ggattcagcc ggatcaacat   180
ctaccacaac actgccagca acaccttcag agtcgttgga gtcaagttgc aggatcagca   240
ggttgtgatc aatta                                                    255
```

<210> SEQ ID NO 144
<211> LENGTH: 255
<212> TYPE: DNA
<213> ORGANISM: H. Sapiens

<400> SEQUENCE: 144

```
cgcccctcgg gggcggctgt ggcggaggaa cgatggccga cggcggcggc cctaaggagg    60
cgccaagcct gcggagctct cccgggccgg cgccgcgggt cccgcgcgcg gtcgggccga   120
gtggcggtgg cggggagacc ccgcggaccg cggcgctggc gctgcgcttc gacaagccca   180
ttaagcaggc cttctacaac accggggccg tgctgttcgt gtgcctgtgc tgcggcgccg   240
cggtgctggt ctact                                                   255
```

<210> SEQ ID NO 145
<211> LENGTH: 255
<212> TYPE: DNA
<213> ORGANISM: H. Sapiens

<400> SEQUENCE: 145

```
ctacgtgcaa aagcagaatg ggaaggctaa gggacagctt cccgatctaa actattggat    60
aaacttcaga cctatttacc accatcagtg atgcttcccc cacggcgttt acagactctc   120
ctgcggcagg cggtggaact acaaagggat cggtgcctat atcacaatac caaacttgat   180
aataatctag attctgtgtc tctgcttata gaccatgttt gtagtaggag gcagttccca   240
tgttatacgc agcag                                                   255
```

<210> SEQ ID NO 146
<211> LENGTH: 255
<212> TYPE: DNA
<213> ORGANISM: H. Sapiens

<400> SEQUENCE: 146

```
tgccgctgga gccggtgtcc gggctggtga tggggttaat tccctttcgt aagactctta    60
cttgcaccca cccagccccg ccgtcgcccc gccgcgccgc gctccaaccg cctcctcctc   120
ctcagtaacg cgggccacgg aaaggtatga tatatttgat ccaagacagt ccattccagt   180
ccgggaatct acagtggtga caaggacatg ggactcctcc tgccagatta cagatggttc   240
actacagttg acatc                                                   255
```

<210> SEQ ID NO 147
<211> LENGTH: 255
<212> TYPE: DNA
<213> ORGANISM: H. Sapiens

<400> SEQUENCE: 147

```
ctcagctacg caggtgcaac ttcttgcgcc aacgtctggt cctgtctacc ctgagcgggc    60
gccccgtcaa aatccgaaag attcgggcca gagacgacaa cccgggcctc cgagattttg   120
```

```
aagccagctt cataaggcta ttggacaaat aacgaatggt tctcgaattg aaataaacca      180
aacaggaaca accttatatt atcagcctgg cctcctgtat ggtggatctg tggaacatga      240
ctgtagcgtc cttcg                                                      255
```

<210> SEQ ID NO 148
<211> LENGTH: 255
<212> TYPE: DNA
<213> ORGANISM: H. Sapiens

<400> SEQUENCE: 148

```
gtgatttgct ggaattgtca ttagtgttga cgatgtgtca cactgtgtaa gggaatcgca      60
tggagatggg cattccgaac tgttaatggg gacatgggac tccagttgtc tctgatcact     120
tgtgtggatt ttcctggcgt agaacgacag aagccgctag taagtcgcca agacctacag     180
caggaattct gcaccaaagg gcataaaatc ttgttatttt aatttgcatc tgggagaatg     240
tctgagcaag gagac                                                      255
```

<210> SEQ ID NO 149
<211> LENGTH: 255
<212> TYPE: DNA
<213> ORGANISM: H. Sapiens

<400> SEQUENCE: 149

```
cccctcaccc cactcaactg ccccgggccc ccgcgcgcgc ggccgcccct ccactcaccc      60
tgtgtcggcc ccgctcccct ctcccccacc aggcgagcag gcgagcgggc agagcccgcg     120
gcggaggtcg gcgcggctcc ggggttcatg gtgacgaggc ggcggccgct cgagcccagc     180
ggcggcgggc ggcgggagct ggggcgcggg cccgggccgc ctctcccaga gcgcggggcc     240
gggcggcggg cgcgc                                                      255
```

<210> SEQ ID NO 150
<211> LENGTH: 255
<212> TYPE: DNA
<213> ORGANISM: H. Sapiens

<400> SEQUENCE: 150

```
taaatgaaag caacaggagc tgctccgggg actgcttttg ccagcaccca gaatcagtgc      60
tcaggctcag aaatcctgga tagaaagagc attttataaa agagaatgtg tccacatcat     120
acccagcacc aaagaccccc ataggtgttg ctgtgggcgt ctgataggcc agcatgctgg     180
cctcaccccc agtatctccg tgcttcagaa tgagaaaaat gaaagtcgcc tctcccgaaa     240
tgacatccag tctga                                                      255
```

<210> SEQ ID NO 151
<211> LENGTH: 255
<212> TYPE: DNA
<213> ORGANISM: H. Sapiens

<400> SEQUENCE: 151

```
atgctggggg aggggctggc ggcctcgacg gcagctgcgg aactaggccg agggacaaag      60
gctaagtttt tccatggttt ggactggata tcggtggaac tctggtcaag ctggtatatt     120
ttgaacccaa agacatcact gctgaagaag aagaggaaga agtggaaagt cttaaaagca     180
ttcggaagta cctgacctcc aatgtggctt atgggtctac aggcattcgg gacgtgcacc     240
tcgagctgaa ggacc                                                      255
```

```
<210> SEQ ID NO 152
<211> LENGTH: 255
<212> TYPE: DNA
<213> ORGANISM: H. Sapiens

<400> SEQUENCE: 152
agtgcggcgg cgccgcctct gctctcagtg ccccggatcg gaggccgtcc atcgcccctc      60
gggccgacgc catgaagatc aaagatgcca agaaaccctc tttcccatgg tttggcatgg     120
acattggggg aactctagta aagctctcgt actttgaacc tattgatatc acagcagagg     180
aagagcaaga agaagttgag agtttaaaaa gtattcggaa atatttgact tctaacgtgg     240
catatggatc caccg                                                      255

<210> SEQ ID NO 153
<211> LENGTH: 255
<212> TYPE: DNA
<213> ORGANISM: H. Sapiens

<400> SEQUENCE: 153
atgcgaggct ggggccggtt gcctaccggc cgcttctcgc cgaggcagtc cagactttc      60 ccccggcggt gcccgctcca agacagcatc tgtcaacgct cctcttctcc cctcctcctc    120
ctgccgggcc gggctccgcc ggctgcggcc gagaggacgc gggacccggc gcggtgagcc    180
catcagctgt caggcgagcg gcgaagcggc tggagggcgg cgagagacac acaaagaacg    240
cggtgggcgg cggcg                                                     255

<210> SEQ ID NO 154
<211> LENGTH: 255
<212> TYPE: DNA
<213> ORGANISM: H. Sapiens

<400> SEQUENCE: 154
atgtattgaa agggtatgta taggtgcaaa tgataaaaaa gaagagtttg atgtttccgg      60
aaatggaagg attgaaggcc atataggtgt gcaattacaa gagcattcct atcttgagaa     120
gggcatgctg gcgtctgagg aactgtcaca gtctggtggt agcaccaaag atgatgaatt     180
agcttcaacc actactccaa agagagggag acctaaaggt aacatctcac ggacgtgttc     240
acactgtggc ctttt                                                      255

<210> SEQ ID NO 155
<211> LENGTH: 255
<212> TYPE: DNA
<213> ORGANISM: H. Sapiens

<400> SEQUENCE: 155
ggcacgaggc tggtccctgg cccaacatga tactgaccaa agctcagtac gacgagatag      60
cccagtgcct agtgtctgtg ccgcctacca ggcagagcct gaggaagctg aagcagaggt     120
ttcccagtca atcgcaggcc actctgctga gcatcttctc ccaggagtac cagaaacaca     180
ttaaaagaac acatgccaaa catcatactt cggaagcaat tgaaagttat taccagaggt     240
acctgaatgg agtgg                                                      255

<210> SEQ ID NO 156
<211> LENGTH: 255
<212> TYPE: DNA
<213> ORGANISM: H. Sapiens

<400> SEQUENCE: 156
```

```
ggcacgaggt agagaagcag gggatagact cataggctgc aacaaaggtg actctgtccc    60
tggacactgc ctccgtactt tctccttgct tcactggcca cagcatctcc ctccagccct   120
cgctatgtgc ctctgccatc ttcacccatc atggagcaga ggtgaggaga ggcagcctgg   180
gaatatggag accagtgaag gaccaggcct ggagagcaca gggtcctacc tgggcatcca   240
gcagaggagc cccta                                                    255
```

<210> SEQ ID NO 157
<211> LENGTH: 255
<212> TYPE: DNA
<213> ORGANISM: H. Sapiens

<400> SEQUENCE: 157

```
ggctggaagg tttagcagca gcctggtgca gtgccctgtc atcaagacaa acccacggtc    60
ctcctgggtg cctaccaagc ttggtttgta caaaagcaag gtgggagtct attttttgtac  120 atgagataca tcacacttac ctgtgggcca gtattgtgaa gtgagtctga gttgtttaca   180
ctgatgcctt ccctgcccac acaaattgt gtacatagtc ttcagatgat accaccccttt   240 tccccagctc ccaac                                                    255
```

<210> SEQ ID NO 158
<211> LENGTH: 255
<212> TYPE: DNA
<213> ORGANISM: H. Sapiens

<400> SEQUENCE: 158

```
ggttcccagg cacaggaacc aatcctggtc tcagccaaga ccatgctgga gagttcatcg    60
tacctcattc gcactgcacg ctctctggcc atcaaccccca agacccacc cacctggtct   120 gtactggctg acattcccca tacagtgtcc gactccatca agagtctcat cacttctatc   180
agggacaagg cccctggaca gagggagtgt gattactcca tcgatggcat caaccggtgc   240
atccgggaca tcgag                                                    255
```

<210> SEQ ID NO 159
<211> LENGTH: 255
<212> TYPE: DNA
<213> ORGANISM: H. Sapiens

<400> SEQUENCE: 159

```
agttcatccg cattcacttt ggtccctctg ggaagctggc atccgcggat attgacagct    60
atctcctgga gaagtcgcgg gtgatcttcc agttgcctgg tgagcgcagc taccatgtct   120
actaccagat cctctcaggg aggaagccag agctgcagga catgctgctt ctgtctatga   180 accccctatga ctaccacttc tgcagccagg gcgtcatcac cgtggacaac atgaatgatg   240
gggaggagct catcg                                                    255
```

<210> SEQ ID NO 160
<211> LENGTH: 255
<212> TYPE: DNA
<213> ORGANISM: H. Sapiens

<400> SEQUENCE: 160

```
cgaggtgctg cgggtgcagg acaagtactt ccacatcaag tgcttcgtct gtaaagcatg    60
tggctgcgac ctggccgagg gcggcttctt cgtgcggcag ggcgagtaca tctgcacgct   120
ggactaccag aggctctacg gcacccgctg cttcagctgc gaccagttca ttgagggtga   180
```

```
ggtggtgtcg cgctgggca agacctacca ccccgactgc ttcgtgtgtg ccgtctgccg      240
gctgcccttc ccccc                                                     255

<210> SEQ ID NO 161
<211> LENGTH: 255
<212> TYPE: DNA
<213> ORGANISM: H. Sapiens

<400> SEQUENCE: 161
tctcagcgga cttgtgcatg ttagctgtgt agatttatgt gagggcttgt aaaactctgg      60
tcttgtaaac tagtcttaag cgcttttaat atggagacag atgagagccc ctctccgctc     120
ccgtgtgggc ccgcaggaga agcggtgatg gagagccgag ctcgcccctt ccaagcgctg     180
ccccgtgagc agtctccacc acctcccctg caaacgtcca gtggtgcaga ggtaatggac     240
gttggctctg gtggt                                                     255

<210> SEQ ID NO 162
<211> LENGTH: 255
<212> TYPE: DNA
<213> ORGANISM: H. Sapiens

<400> SEQUENCE: 162
ccttccggtc accatggcga ccaggcgcct tggggtcggg gagacgctgg gggccctcaa      60
cgcggccctg gggccaggcg gtccggtgtg gaccaaggag acgcgcaccc gccacctgcg     120
ttcccgagac tttctggcac cgcaccgcgc gctgcaggcg cgcttcgatg acggccaggt     180
tccggagcat ttgctccatg ccctcgcctg cctgcagggc cccggtgtgg ccccggtgct     240
gcgctgcgcg ccgac                                                     255

<210> SEQ ID NO 163
<211> LENGTH: 255
<212> TYPE: DNA
<213> ORGANISM: H. Sapiens

<400> SEQUENCE: 163
gcacaatcta aagcttgtat atataatggt agtttgtaaa gtgtaccttc cccacaggac      60
gctgtgggat gtaaatttgt aggtcgagtt tacagctggt ttttcttgac tgaagctcat     120
tcaactggtt acttctttgt gggtgtcttt aatgaagctt ataaatggca aaaagcaaac     180
attcccatgg tttggcatgg acatcggtgg aacgctggtt aaattggtgt atttcgagcc     240
gaaggatatt acagc                                                     255

<210> SEQ ID NO 164
<211> LENGTH: 255
<212> TYPE: DNA
<213> ORGANISM: H. Sapiens

<400> SEQUENCE: 164
agcggagccc cgagccgccc gcagagcaag cgcggggaac caaggagacg ctcctggcac      60
tgcagataac ttgtctgcat ttcaagaaca acctaccaga gaccttacct gtcaccttgg     120
ctctcccacc caatggagat ggctctaatg gtggcacaaa ccaggaaggg gaaatctgtg     180
gtttaaattc tttatgcctc atcctctgag tgctgaaggc ttgctgtagg ctgtatgctg     240
ttaatgctaa tcgtg                                                     255

<210> SEQ ID NO 165
<211> LENGTH: 255
```

```
<212> TYPE: DNA
<213> ORGANISM: H. Sapiens

<400> SEQUENCE: 165
gttctctcgc tcaggtctct gcatgtagtt gtcacttgca gctccatttc catcacgtgg      60
taaaatgccc tttctcttct ttcctgcaga tggatggttt ctagtgtgct tccaaacccc     120
acctcggctg agtgttgggc agcacttcta catgatccta tgactcttga tatggacgca     180
gtcctgtcag actttgttcg gtccacgggg gcagaacctg gtctggccag agacctgctg     240
gaaggcaaaa actgg                                                      255

<210> SEQ ID NO 166
<211> LENGTH: 255
<212> TYPE: DNA
<213> ORGANISM: H. Sapiens

<400> SEQUENCE: 166
tcggcggcgg tggcggaggc gacctcgcga cctgtgtcag cagagccgcc ctgcaccacc      60
atgtgcatca tcttctttaa gtttgatcct cgccctgttt ccaaaaacgc gtacaggctc     120
atcttggcag ccaacaggga tgaattctac agccgaccct ccaagttagc tgacttctgg     180
gggaacaaca acgagatcct cagtgggctg gacatggagg aaggcaagga aggaggcaca     240
tggctgggca tcagc                                                      255

<210> SEQ ID NO 167
<211> LENGTH: 255
<212> TYPE: DNA
<213> ORGANISM: H. Sapiens

<400> SEQUENCE: 167
acctgcatct gccaacaaga ctggaagcag gtgaggcaca cagaggggga ggcccgcagc      60
tgcgtgggag gaggggtggt ctgagggacg tgggatgccg ggaatgaggc tggtttgcag     120
gttggcgcat ggacattttc ccagaaaggg acagagacgg cgaagtttga cggtctggaa     180
agcagagacc agcagggctg actgcttggg agcaccaaat atccggacag cgcctctcgg     240
gaggtccgag aagag                                                      255

<210> SEQ ID NO 168
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 168
tccacaaagc tgaacatgtc t                                                21

<210> SEQ ID NO 169
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 169
ctaccatagg gtaaaaccac t                                                21

<210> SEQ ID NO 170
<211> LENGTH: 20
<212> TYPE: DNA
```

```
<213> ORGANISM: Artificial Sequence
<220> FEATURE:
<223> OTHER INFORMATION: synthetic oligomeric compound

<400> SEQUENCE: 170
tcacttttgt gactatgcaa                                              20

<210> SEQ ID NO 171
<211> LENGTH: 19
<212> TYPE: DNA
<213> ORGANISM: Artificial Sequence
<220> FEATURE:
<223> OTHER INFORMATION: synthetic oligomeric compound

<400> SEQUENCE: 171
caatgcaaca gcaatgcac                                               19

<210> SEQ ID NO 172
<211> LENGTH: 23
<212> TYPE: DNA
<213> ORGANISM: Artificial Sequence
<220> FEATURE:
<223> OTHER INFORMATION: synthetic oligomeric compound

<400> SEQUENCE: 172
tcaacaaaat cactgatgct gga                                          23

<210> SEQ ID NO 173
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 173
actttcggtt atctagcttt a                                            21

<210> SEQ ID NO 174
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 174
cttccagtca aggatgttta ca                                           22

<210> SEQ ID NO 175
<211> LENGTH: 19
<212> TYPE: DNA
<213> ORGANISM: Artificial Sequence
<220> FEATURE:
<223> OTHER INFORMATION: synthetic oligomeric compound

<400> SEQUENCE: 175
caatgcaact acaatgcac                                               19

<210> SEQ ID NO 176
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 176
gcattattac tcacggtacg a                                            21
```

<210> SEQ ID NO 177
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 177
ctacctgcac gaacagcact tt                                              22

<210> SEQ ID NO 178
<211> LENGTH: 18
<212> TYPE: DNA
<213> ORGANISM: Artificial Sequence
<220> FEATURE:
<223> OTHER INFORMATION: synthetic oligomeric compound

<400> SEQUENCE: 178
agacacgtgc actgtaga                                                   18

<210> SEQ ID NO 179
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 179
acatggttag atcaagcaca a                                               21

<210> SEQ ID NO 180
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 180
ggagtgaaga cacggagcca ga                                              22

<210> SEQ ID NO 181
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 181
ccaagttctg tcatgcactg a                                               21

<210> SEQ ID NO 182
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 182
acaaagttct gtgatgcact ga                                              22

<210> SEQ ID NO 183
<211> LENGTH: 22
<212> TYPE: DNA
<213> ORGANISM: Artificial Sequence
<220> FEATURE:

```
<223> OTHER INFORMATION: synthetic oligomeric compound

<400> SEQUENCE: 183
aactatacaa tctactacct ca                                           22

<210> SEQ ID NO 184
<211> LENGTH: 23
<212> TYPE: DNA
<213> ORGANISM: Artificial Sequence
<220> FEATURE:
<223> OTHER INFORMATION: synthetic oligomeric compound

<400> SEQUENCE: 184
aagcccaaaa ggagaattct ttg                                          23

<210> SEQ ID NO 185
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 185
gctgccgtat atgtgatgtc a                                            21

<210> SEQ ID NO 186
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 186
gtaagcgcag ctccacaggc t                                            21

<210> SEQ ID NO 187
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 187
aggcgaagga tgacaaaggg aa                                           22

<210> SEQ ID NO 188
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 188
acaagctttt tgctcgtctt at                                           22

<210> SEQ ID NO 189
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 189
accctccacc atgcaaggga tg                                           22
```

```
<210> SEQ ID NO 190
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 190
agtaacttct tgcagttgga                                                    20

<210> SEQ ID NO 191
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 191
acaggagtct gagcatttga                                                    20

<210> SEQ ID NO 192
<211> LENGTH: 23
<212> TYPE: DNA
<213> ORGANISM: Artificial Sequence
<220> FEATURE:
<223> OTHER INFORMATION: synthetic oligomeric compound

<400> SEQUENCE: 192
taaacggaac cactagtgac ttg                                                23

<210> SEQ ID NO 193
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 193
aacgataaaa catacttgtc a                                                  21

<210> SEQ ID NO 194
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 194
ggtaggtgga atactataac a                                                  21

<210> SEQ ID NO 195
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 195
cgccaatatt tacgtgctgc ta                                                 22

<210> SEQ ID NO 196
<211> LENGTH: 22
<212> TYPE: DNA
<213> ORGANISM: Artificial Sequence
<220> FEATURE:
<223> OTHER INFORMATION: synthetic oligomeric compound
```

```
<400> SEQUENCE: 196
agcctatcct ggattacttg aa                                          22

<210> SEQ ID NO 197
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 197
tatgaaatgc cagagctgcc a                                           21

<210> SEQ ID NO 198
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 198
aacctatcct gaattacttg aa                                          22

<210> SEQ ID NO 199
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 199
tatgatagct tccccatgta a                                           21

<210> SEQ ID NO 200
<211> LENGTH: 23
<212> TYPE: DNA
<213> ORGANISM: Artificial Sequence
<220> FEATURE:
<223> OTHER INFORMATION: synthetic oligomeric compound

<400> SEQUENCE: 200
acatttttcg ttattgctct tga                                         23

<210> SEQ ID NO 201
<211> LENGTH: 24
<212> TYPE: DNA
<213> ORGANISM: Artificial Sequence
<220> FEATURE:
<223> OTHER INFORMATION: synthetic oligomeric compound

<400> SEQUENCE: 201
gacgggtgcg atttctgtgt gaga                                        24

<210> SEQ ID NO 202
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 202
gcaacttagt aatgtgcaat a                                           21

<210> SEQ ID NO 203
<211> LENGTH: 21
```

```
<212> TYPE: DNA
<213> ORGANISM: Artificial Sequence
<220> FEATURE:
<223> OTHER INFORMATION: synthetic oligomeric compound

<400> SEQUENCE: 203
tccgagtcgg aggaggagga a                                           21

<210> SEQ ID NO 204
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 204
aaaagagacc ggttcactgt ga                                          22

<210> SEQ ID NO 205
<211> LENGTH: 20
<212> TYPE: DNA
<213> ORGANISM: Artificial Sequence
<220> FEATURE:
<223> OTHER INFORMATION: synthetic oligomeric compound

<400> SEQUENCE: 205
tcagttatca cagtactgta                                             20

<210> SEQ ID NO 206
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 206
gaaagagacc ggttcactgt ga                                          22

<210> SEQ ID NO 207
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 207
aggcatagga tgacaaaggg aa                                          22

<210> SEQ ID NO 208
<211> LENGTH: 23
<212> TYPE: DNA
<213> ORGANISM: Artificial Sequence
<220> FEATURE:
<223> OTHER INFORMATION: synthetic oligomeric compound

<400> SEQUENCE: 208
tcatagccct gtacaatgct gct                                         23

<210> SEQ ID NO 209
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 209
```

```
gctgcaaaca tccgactgaa ag                                              22

<210> SEQ ID NO 210
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 210
atatgtcata tcaaactcct a                                               21

<210> SEQ ID NO 211
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 211
acagttcttc aactggcagc tt                                              22

<210> SEQ ID NO 212
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 212
actgtacaaa ctactacctc a                                               21

<210> SEQ ID NO 213
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 213
actgtaggaa tatgtttgat a                                               21

<210> SEQ ID NO 214
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 214
taaacatcac tgcaagtctt a                                               21

<210> SEQ ID NO 215
<211> LENGTH: 22
<212> TYPE: DNA
<213> ORGANISM: Artificial Sequence
<220> FEATURE:
<223> OTHER INFORMATION: synthetic oligomeric compound

<400> SEQUENCE: 215
tgctcaataa atacccgttg aa                                              22

<210> SEQ ID NO 216
<211> LENGTH: 22
<212> TYPE: DNA
<213> ORGANISM: Artificial Sequence
```

```
<220> FEATURE:
<223> OTHER INFORMATION: synthetic oligomeric compound

<400> SEQUENCE: 216
agctgctttt gggattccgt tg                                              22

<210> SEQ ID NO 217
<211> LENGTH: 23
<212> TYPE: DNA
<213> ORGANISM: Artificial Sequence
<220> FEATURE:
<223> OTHER INFORMATION: synthetic oligomeric compound

<400> SEQUENCE: 217
tgatagccct gtacaatgct gct                                             23

<210> SEQ ID NO 218
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 218
aaacccctat cacgattagc a                                               21

<210> SEQ ID NO 219
<211> LENGTH: 21
<212> TYPE: DNA
<213> ORGANISM: Artificial Sequence
<220> FEATURE:
<223> OTHER INFORMATION: synthetic oligomeric compound

<400> SEQUENCE: 219
accgaacaaa gtctgacagg a                                               21
```

REGULATION OF EPIGENETIC CONTROL OF GENE EXPRESSION

CROSS-REFERENCE TO RELATED APPLICATIONS

This application is a U.S. National Phase filing, under 35 U.S.C. 371, of International Patent Application having Serial No. PCT/US2005/045063, filed Dec. 12, 2005, which claims priority to U.S. Provisional Application Ser. No. 60/634,840, filed Dec. 10, 2004, each of which is incorporated herein by reference in its entirety.

SEQUENCE LISTING

This application is submitted with a Sequence Listing in electronic format. The Sequence Listing is provided as a file entitled CORE0034USASEQ.txt, created on Jun. 8, 2007, which is 64 Kb in size. The information provided in the Sequence Listing is incorporated herein by reference in its entirety.

TECHNICAL FIELD

The present invention is directed, in part, to methods for evaluating the effects of oligomeric compounds on epigenetic changes in gene expression. The invention is further drawn to methods for regulating epigenetic control of gene expression by oligomeric compounds targeting or mimicking small non-coding RNAs.

BACKGROUND ART

Epigenetic Differences and Therapeutic Applications

Epigenetic changes alter gene expression, and are heritable and yet do not arise due to alterations of DNA sequence. Epigenetic differences allow two cells within the same organism, containing the same genetic complement of DNA, to express unique subsets of genes and to differentiate. Epigenetic differences are initiated and sustained by DNA methylation, RNA-associated silencing, or histone modifications. These components of epigenetic gene regulation can interact and stabilize each other, and as a result modulate chromatin structure. Disruption of one or more of these interacting systems can lead to inappropriate expression or silencing of genes, resulting in what are known as 'epigenetic diseases', which include developmental disorders such as fragile X syndrome, Angelman's syndrome, Prader-Willi syndrome, cancers such as leukemia, and immune regulation disorders such as ICF syndrome (Egger et al., Nature, 2004, 429, 457-463).

Methylation typically occurs at the cytosine of CpG dinucleotides within mammalian genomic DNA. "CpG islands" are long tracts of DNA with high GC content commonly found in promoter regions. In general, methylation of promoters is inhibitory and accounts for one type of epigenetic gene silencing, such as occurs in parentally imprinted genes. With the exception of the X-chromosome, CpG residues in promoter regions are typically unmethylated, and methylation occurs after DNA replication, resulting in a loss of gene expression (Gamis et al., Mol. Cancer, 2004, 3, 1-23).

Histone modifications occur post-transcriptionally and include the acetylation and methylation of conserved lysine residues on the amino-terminal tail domains of histones. Generally, the acetylation of histones marks active, transcriptionally competent regions, whereas under-acetylated histones are found in transcriptionally inactive euchromatic or heterochromatic regions. Histone methylation can be a marker for both active and inactive regions of chromatin. For example, methylation of lysine 9 on the N terminus of histone H3 (H3-K9) is a hallmark of silent DNA and is globally distributed throughout heterochromatic regions such as centromeres and telomeres. Conversely, methylation of lysine 4 of histone H3 (H3-K4) denotes activity and is found predominantly at promoters of active genes (Lachner and Jenuwein, Curr. Opin. Cell Biol., 2002, 14, 286-298).

RNA-associated silencing plays a role in post-transcriptional gene silencing and is accomplished by RNA in the form of antisense transcripts, non-coding RNAs, or RNA interference. RNA-associated silencing can also lead to mitotically heritable transcriptional silencing by the formation of heterochromatin.

Aberrant changes in the epigenetic control of gene expression have been increasingly recognized as factors contributing to the development of human disease, including hyperproliferative disorders, autoimmune disorders and developmental disorders. By way of example, aberrant, heritable gene silencing as a result of DNA hypermethylation has been linked to the genesis and progression of cancer. Inhibitors of DNA methylation, known as DNA demethylating agents, rapidly reactivate the expression of genes that have undergone epigenetic silencing, and are active only in S-phase cells. Likewise, the progression of cancer is often associated with epigenetic silencing associated with histone deacetylation, which is catalyzed by at least three classes of histone deacetylases (HDACs), thus HDAC inhibitors are used to induce differentiation, growth arrest and/or apoptosis in transformed cells in tumors (Egger et al., Nature, 2004, 429, 457-463).

While DNA demethylating drugs, such as 5-azacytidine, and HDAC inhibitors, such as phenylbutyric acid, are used to prevent or reverse hypermethylation, or acetylation, respective, such agents do not target individual enzymes or cell types. Thus, the application of demethylating agents or HDAC inhibitors to the treatment of disease lacks precision. The concerns regarding the clinical applications of these agents relate mainly to the nonspecific activation of genes and transposable elements in normal cells, and also to potential mutagenicity and carcinogenicity. Imprinted genes can be activated by 5-azacytidine, underscoring the need for careful application of this and related agents (Eversole-Cire, Mol. Cell. Biol., 1993, 13, 49284938).

Agents which work through RNA interference pathways are currently in research and development for possible therapeutic applications. There are concerns that these agents may induce specific or non-specific alterations in epigenetic control of gene expression. Thus, there is a need to ensure that any agents working through an RNA interference pathway that are developed for therapeutic applications do not cause undesired side effects through RNA associated silencing.

Heterochromatin also plays a role in the regulation of gene expression during development and cellular differentiation. Epigenetic control of gene expression may be a factor in the differentiation and dedifferentiation of pluripotent stem cells (such as embryonic stem cells) as well as in reprogramming the status of a cell during somatic cell nuclear transfer (i.e. cloning). Modulating the epigenetic control of gene expression in stem cells could be useful to keep stem cells in an undifferentiated state or in driving the stem cells towards a desired differentiated state.

As such, there remains a long-felt need for agents that regulate epigenetic processes such as DNA methylation, histone modifications and RNA-mediated silencing, without causing undesired alterations in the epigenetic control of gene expression. Similarly, there is a need for screening methods to identify agents that specifically regulate such epigenetic processes and allow for the development of therapeutic agents that modify aberrant epigenetic processes with precision. Oligomeric compounds targeting or mimicking specific small non-coding RNAs that participate in epigenetic processes are extremely attractive as therapeutic agents to selectively modulate epigenetic processes impacting human diseases such as cancers, developmental disorders, infections, and autoimmune disorders.

Mechanisms of Epigenetic Differences

Chromatin structure affects both gene transcription and cellular phenotype. The most condensed chromatin domains are known as heterochromatin, whereas the more extended chromatin domains are known as euchromatin. Euchromatic domains are generally transcriptionally active, accessible portions of the genome, whereas heterochromatic domains are generally inaccessible to DNA binding factors and are transcriptionally silent. Heterochromatin plays a role in chromosome structures, by stabilizing the repetitive DNA sequences at centromeres, telomeres and elsewhere in the genome and inhibiting recombination between homologous repeats. Furthermore, heterochromatin proteins associated with repeated DNA sequences surrounding centromeres are required for proper sister chromatid cohesion and chromosome segregation.

Faithful chromosome segregation and maintenance of genomic integrity are crucial cellular processes. For example, improper chromosome segregation during mitosis or meiosis results in aneuploidy, which is associated with tumorigenesis, spontaneous abortion, and congenital disorders such as trisomies (e.g., Down's syndrome). Telomere length is associated with cellular lifespan. Heterochromatin within centromeric and telomeric regions is believed to play both mechanical and regulatory roles in propagating and maintaining the integrity of the eukaryotic genome.

Heterochromatin-like structures are involved in the inactivation of developmental regulators such as the homeotic gene clusters in *Drosophila* and mammals, and the mating type genes in fungi. Moreover, dosage compensation in female mammals involves the heterochromatic inactivation of one of the two X chromosomes in somatic cells.

Another example of a heterochromatic region is an insulator. Insulators are DNA sequence elements that can, in some instances, act as barriers to protect a gene against the encroachment of adjacent inactive condensed chromatin. Insulators also can act as blocking elements to protect against the activating influence of neighboring cis-acting elements, and/or distal enhancers associated with other genes, for example, when the insulator is located between an enhancer and a promoter. Insulators thus are complex elements that can help to preserve the independent function of genes embedded in a genome in which they are surrounded by regulatory signals they must ignore.

Chromatin must be "remodeled" to allow transcription factors and RNA polymerase to interact with the DNA helix. Many of the trans-acting factors required for heterochromatin modulation are enzymes that directly modify histones. Histone modifying enzymes are known to regulate chromatin structure through acetylation, methylation, and/or phosphorylation of the histone proteins. In fission yeast and metazoans, several histone deacetylases (HDACs) are required for gene silencing. In fact, hypoacetylation works in conjunction with methylation to effect gene silencing. Methylation of a particular lysine in histone H3 (H3 K9) by the conserved histone methyltransferase Su(var)3-9 in *Drosophila*, SUV39H1 in human, and Clr4 in fission yeast creates a high affinity binding site within pericentric heterochromatin for the conserved heterochromatin protein 1 (HP1) in flies and humans, and the HP1-homolog in fission yeast, Swi6 (Grewel et al., Science, 2003, 301, 798-802; and Perrod et al., Cell. Mol. Life. Sci., 2003, 60, 2303-18). Furthermore, a complex containing both Suv39H1 and histone deacetylases is reported to be involved in heterochromatin silencing or transcriptional repression by the tumor suppressor retinoblastoma protein (Rb) (Vaute et al., Nucleic Acids Res., 2002, 30, 475-81). It has also been reported that cells entering mitosis with hyperacetylated histones displayed altered chromatin conformation associated with depletion of HP1 from the centromeric heterochromatin. Inhibition of histone deacetylation before mitosis produced defective chromosome condensation and impaired mitotic progression in living cells (Cimini et al., Mol. Biol. Cell, 2003, 14, 3821-3833). Thus, the methylation and acetylation states of histones may together direct centromeric heterochromatin formation.

Although chromatin compaction is necessary to contain huge lengths of DNA in the nucleus, chromatin structure must also be dynamic enough to allow genes to remain accessible and able to mount a rapid transcriptional response when cells are faced with infectious insults or environmental or developmental transitions. Complicating matters is the fact that a large percentage (up to 98%) of human DNA does not encode proteins, and consists of repetitive elements, some of which contain promoters from which transcription can initiate (Forsdyke et al., Trends Immunol., 2002, 23, 575-79). A cell must be able to distinguish desirable versus undesirable gene expression and "self" versus "nonself" nucleic acid material. One structural feature indicating unwanted, nonself, potentially predatory nucleic acid material is presence of double-stranded RNA (dsRNA). Not a usual byproduct of normal gene expression, dsRNA is a component of the life cycle of most viruses. By flagging dsRNA as a sign of unwanted RNA replication, and by avoiding production of dsRNA during most normal gene expression, the cell maintains some level of protection from infection.

RNA interference (RNAi) is an evolutionarily conserved type of epigenetic process in which small dsRNA molecules fully- or partially-complementary to a target nucleic acid induce highly specific gene silencing by triggering the degradation or translational suppression of homologous mRNA. RNAi is believed to represent a form of eukaryotic genome defense from invasion by exogenous sources of genetic material such as RNA viruses and retrotransposons (Carmell et al., Nature Struct. Mol. Bio., 2004, 11, 214-8; Eddy, Nat. Rev. Genet., 2001, 2, 919-929; and Silva et al., Trends Mol. Med., 2002, 8, 505-508).

Sources of triggers for RNAi include exogenously introduced dsRNA, RNA viruses, transposons and endogenous short dsRNAs. In the current model, these triggers are processed by the RNase III enzyme Dicer into small 21-24 nucleotide (nt) short interfering RNAs (siRNAs) which then serve as sequence specific guides to an effector complex called the RNA-induced silencing complex (RISC) that carries out the destruction of homologous mRNAs. Over the past two years, a populous class of endogenous substrates that enter the silencing pathways, the microRNAs or miRNAs, has been described. miRNAs are transcribed from the genomes of diverse organisms, and are reported to lead to suppression of translation, or to target mRNA destruction. In humans, some clustered miRNA genes are transcribed polycistronically as primary precursors (known as pri-miRNAs) that are several hundred bases long. Nonclustered miRNA genes are also predominantly expressed as long nascent transcripts that require further processing, and both the poly- and monocistronic pri-miRNAs undergo a processing step in the nucleus, by another RNase III enzyme, Drosha, that produces shorter, approximately 70-nt pre-miRNAs. The pre-miRNAs are then believed to be exported from the nucleus by exportin-5, a nuclear export factor. Once in the cytoplasm, Dicer processes the pre-miRNAs into mature, approximately 22-nt miRNAs (Carmell et al., Nature Struct. Mol. Bio., 2004, 11, 214-8).

There is evidence that endogenous substrates that enter the RNAi pathway such as the precursors of small non-coding RNAs may undergo RNA editing. RNA editing enzymes have been reported to interact with components of the RNAi pathway. Adenosine deaminases that act on RNA (ADARs) are a class of RNA editing enzymes that deaminate adenosines to create inosines in dsRNA. Inosine is read as guanosine during translation, and thus, one function of editing is to generate multiple protein isoforms from the same gene. ADARs bind to dsRNA without sequence specificity, and due to the ability of ADARs to create sequence and structural changes in dsRNA, ADARs could potentially antagonize RNAi by several mechanisms, such as preventing dsRNA from being recognized and cleaved by Dicer, or preventing siRNAs from base-pairing. Recently, it was shown that the editing of dsRNA by ADARs can prevent somatic transgenes from inducing gene silencing via the RNAi pathway (Knight et al., Mol. Cell, 2002, 10, 809-817). Furthermore, it was recently reported that human and mouse miRNA22 precursor molecules are subject to posttranscriptional modification by A-to-I RNA editing in vivo (Luciano et al., RNA, 2004, 10, 1174-7).

A surge of interest in the RNAi field has resulted in the identification of hundreds of small non-coding RNAs believed to act in gene silencing. One example is a class of small untranslated RNAs, the repeat-associated small interfering RNAs (rasiRNAs), that are associated with repeated sequences, transposable elements, satellite and microsatellite DNA, and Suppressor of Stellate (SOS) repeats, suggesting that small RNAs participate in defining chromatin structure (Aravin et al., Dev. Cell, 2003, 5, 337-350).

Although initially thought of as a purely post-transcriptional process, RNAi appears to act at the transcriptional level as well (Ekwall, Mol. Cell, 2004, 13, 304-5). RNAi may be involved in the formation of heterochromatin at centromere regions which can suppress recombination between homologous repeated DNA sequences. Furthermore, RNAi now believed to play a role in centromere function. A large percentage of small RNAs cloned from the fission yeast, S. pombe, were found to have perfect homology to portions of the centromere region in this organism (Reinhart et al., Science, 2002, 297, 1831), and it was shown that genes involved in the RNA interference pathway are required for pericentromere heterochromatin formation and chromosome segregation (Dawe, Plant Cell, 2003, 15, 297-301; and Volpe et al., Science, 2002, 297, 1833-7). An RNAi effector complex known as the RNA-induced Initiation of Transcriptional gene Silencing (RITS) complex was recently purified and found to be required for heterochromatin assembly in fission yeast. The RITS complex directly links small RNAs produced by Dicer to heterochromatin, because it contains both a previously known chromodomain protein, Chp1, which binds centromeres, and the S. pombe Argonaute homolog (Ago1), which plays a role in RNAi. The RITS complex also contains a previously uncharacterized protein, Tas3, as well as small RNAs that require Dicer for their production. These small RNAs are homologous to centromeric repeats and are required for the localization of the RITS complex to heterochromatic domains, as well as for the methylation of H3 K9 and Swi6 binding to centromeric chromatin, suggesting that RNAi-related processes and small RNAs are involved in epigenetic gene silencing at specific chromosomal loci (Verdel et al., Science, 2004, 203, 6726; and Ekwall, Mol. Cell, 2004, 13, 304-5).

Similar links between RNAi, chromatin modifications, and transcriptional regulation have been established in plants, flies, and the unicellular ciliate, Tetrahymena. In a screen for mutants that suppress silencing in Arabidopsis, the ago4-1 mutant (in the Argonaute family of genes involved in RNAi) was cloned and found to reactivate silenced alleles and decrease CpNpG and asymmetric DNA methylation as well as histone H3 K9 methylation. In addition, the ago4-1 mutant blocked the accumulation of 25-nt siRNAs corresponding to the retroelement AtSN1 (Zilberman et al., Science, 2003, 299, 716-9). In Drosophila, dosage compensation involves epigenetic processes such as the specific acetylation of histones by a histone acetyltransferase, MOF, which specifically binds through its chromodomain to the non-coding RNA roX, an RNA predicted to contribute to chromatin assembly of the dosage compensation complex (DCC) (Akhtar et al., Nature, 2000, 407, 405-9). Also in Drosophila, HP1 localization to heterochromatic regions is dependent on the RNAi machinery (Pal Bhadra et al., Science, 2004, 303, 669-672). In Tetrahymena, RNAi was shown to direct chromatin modifications and DNA elimination (Ekwall, Mol. Cell, 2004, 13, 304-5).

Another role of RNAi in fission yeast is to direct formation of localized repressive chromatin to genes in euchromatin, as was shown by expressing an inverted repeat RNA, which can form a short hairpin RNA (shRNA) capable of targeting heterochromatin formation and cohesin binding in trans. Endogenous, developmentally regulated, lineage-restricted genes (meiotic genes), were also found to be repressed by a similar process involving nearby retrotransposon long terminal repeats (LTRs), implicating interspersed LTRs in regulation of gene expression during cellular differentiation. It was concluded that dsRNA transcripts are acted on by the RNAi pathway to generate siRNAs which trigger the nucleation of a patch of dimethylated H3 K9, Swi6-bound silent chromatin, which can spread outward to silence adjacent genes and attract the evolutionarily conserved Cohesin protein complex mediating sister chromatid cohesion (Schramke et al., Science, 2003, 301, 1069-74). It was further noted that proteins related to CENP-B and the mariner class of transposases also bind pericentric regions of fission yeast centromeres and contribute to the formation of heterochromatin (Shramke et al., Science, 2003, 301, 1069-74; and Nakagawa et al., Genes Dev., 2002, 16, 1766-78).

Some heterochromatin proteins found associated with centromeres and/or telomeres have been shown to be involved in RNA modification and/or RNA degradative processes. Yeast Cbf5p was originally isolated as a low-affinity centromeric DNA binding protein; Cbf5p also binds microtubules in vitro and interacts genetically with two known centromere-related protein genes (NDC10/CBF2 and MCK1). However, Cbf5p was found to be nucleolar and was later found to be involved in transcription and processing of ribosomal RNAs (Jiang et al., Mol. Cell. Biol., 1993, 13, 4884-93; and Cadwell et al., Mol. Cell. Biol., 1997, 17, 6175-83). Cbf5p is a component of a ribonucleoprotein complex that includes box H/ACA small nucleolar RNAs (snoRNAs) and this complex was found to direct the site-specific pseudouridylation of ribosomal RNAs (rRNAs) (Zebarjadian et al., Mol. Cell. Biol., 1999, 19, 7461-72). The RNA component, hTR, of human telomerase, a ribonucleoprotein (RNP) particle required for the replication of telomeres, contains a domain structurally and functionally related to box H/ACA snoRNAs, and hTR is believed to be associated with Dyskerin (the human counterpart of yeast Cbf5p) (Des et al., Nucleic Acids Res., 2001, 29, 598-603). Furthermore, mutations in the human DKC1 gene encoding dyskerin cause dyskeratosis congenita, a rare and fatal inherited syndrome characterized by abnormal skin pigmentation, nail dystrophy and mucosal leukoplakia, and the predisposition to bone marrow failure and malignancies (Mochizuki et al., Proc. Natl. Acad. Sci. U.S., 2004, 101, 10756-61).

Another budding yeast gene, CEP1/CBF1/CP1, is believed to be involved in assembling higher order chromatin structures at centromeres and is associated with a multisubunit complex that processes and degrades RNAs. The CEP1 gene was found to genetically interact with the CSL4/SKI4 gene (Baker et al., Genetics, 1998, 149, 73-85), and the Csl4 protein was later found to be a core component of the exosome, a complex containing multiple 3'-to-5' riboexonucleases and RNA binding proteins, which is located in both the nucleus and the cytoplasm (van Hoof et al., Mol. Cell. Biol., 2000, 29, 8230-43). In the cytoplasm, the exosome participates in degradation of mRNAs containing AREs (AU-rich elements) such as mRNAs encoding growth factors, cytokines, and proto-oncogene products, whose abundance must be able to change rapidly. Also in the cytoplasm, the exosome has been shown to control the levels of the double-stranded LA virus in yeast. In the nucleus, the exosome is required for trimming the 5.8S rRNA from a 3'-extended precursor, it plays a role in degrading inefficiently spliced or unadenylated pre-mRNAs, and it participates in 3'-end maturation of small nuclear RNAs (snRNAs) and snoRNAs (van Hoof et al., Cell, 1999, 99, 347-50; van Hoof et al., Current Biol., 2002, 12, R285-7; and Butler, Trends Cell Biol., 2002, 12, 90-6).

At least one exosome component has another link to centromere-related function; the fission yeast dis3 gene was originally identified as a mitotic control protein required for sister chromatid separation. The dis3-54 mutation resulted in defective chromosome segregation (Kinoshita et al., Mol. Cell. Biol., 1991, 11, 5839-47; and Ohkura et al., EMBO J., 1988, 7, 1465-73). The S. pombe dis3 gene was later found to be the ortholog of the exosomal protein RRP44, suggesting involvement of nuclear exoribonucleases in chromosome segregation (Shobuike et al., Nucleic Acids Res., 2001, 29, 1326-33). Finally, the RRP44/dis3 gene may be linked to human cancer; human chromosomal region 13q21-q22, containing the KIAA1008 protein (homologous to the fission yeast mitotic control protein dis3), harbors a putative breast cancer susceptibility gene, and has been implicated as a common site for somatic deletions in a variety of malignant tumors (Rozenblum et al., Hum. Genet., 2002, 110, 111-21).

The human homologue of the yeast exosome was recently shown to be the autoantigenic polymyositis/scleroderma (PM/Scl) complex. In addition to targeting the known autoantigens PM/Scl-100 and PM/Scl-75, autoantibodies also target six recently identified components of the PM/Scl complex. In sera from patients with idiopathic inflammatory myopathy, scleroderma, or the PM/Scl overlap syndrome, autoantibodies were found to be directed to the human exosome components hRrp4p, hRrp40p, hRrp41p, hRrp42p, hRrp14p and hCsl4p (Brouwer et al., Arthritis Res., 2002, 4, 134-138).

Most recently, Dicer has been shown to be essential for heterochromatin formation in vertebrate cells. Loss of Dicer results in cell death with the accumulation of abnormal mitotic cells exhibiting premature sister-chromatid separation. Aberrant accumulation of transcripts from alpha-satellite sequences, which consist of human centromeric DNA repeats, was detected in Dicer-deficient cells. Furthermore, two heterochromatin proteins, the Rad21 cohesin protein and BubR1, a cell cycle checkpoint protein, were found to be mislocalized in cells lacking Dicer. It was concluded that the RNAi machinery is involved in the formation of heterochromatin structure in higher vertebrate cells (Fukagawa et al., Nature Cell Biol., 2004, 6, 784-91).

DISCLOSURE OF THE INVENTION

Summary of the Invention

The present invention includes a method of screening oligomeric compounds which modulate degradation or translational suppression of a target nucleic acid molecule, comprising identifying one or more heterochromatic regions subject to epigenetic regulation of gene expression, wherein the heterochromatic region does not modulate the expression of the target nucleic acid molecule, and assaying for modifications to the heterochromatic region after treatment with oligomeric compounds. The heterochromatin modification may be acetylation, deacetylation, phosphorylation, dephosphorylation, methylation, demethylation, ubiquitination, sumoylation, pseudouridylation, or a combination thereof.

The present invention also includes a method of screening an oligomeric compound for an effect on heterochromatin function comprising: integrating a reporter gene functionally linked to a target site for a small non-coding RNA into a genomic locus associated with heterochromatin function within a cell; contacting a cell with a vector that expresses a small non-coding RNA; contacting the cell with an oligomeric compound; and assaying the cell or lysate therefrom for an effect on heterochromatin function. The assay can comprise determining reporter vector activity, wherein an increase in reporter vector activity indicates that the oligomeric compound has an effect on heterochromatin function. The assaying can also comprise detecting a change in histone acetylation, histone methylation, RNA pseudouridylation, ubiquitination, sumoylation, or compartmentalization of a ribonucleoprotein complex, or any combination thereof. The small non-coding RNA can be a mature miRNA, or a precursor thereof.

The present invention also includes a method of determining whether a small non-coding RNA influences methylation at a genomic locus. At least one genomic locus having homology to a small non-coding RNA is identified. Methylation-specific primers are designed to amplify a DNA fragment from the genomic region. A cell is contacted with an oligomeric compound targeting the small non-coding RNA. Methylation-specific amplification, such as by PCR, is performed. Changes in the methylation status of the genomic locus in a cell contacted with the oligomeric compound as compared to a cell not contacted with the oligomeric compound is analyzed. A change in the methylation status indicates that the small non-coding RNA influences methylation at the genomic locus.

The present invention also includes a method of a determining whether a small non-coding RNA influences binding of a heterochromatin-related protein at a genomic locus. At least one genomic locus having homology to a small non-coding RNA is identified. Amplification primers, such as PCR primers, are designed to amplify a DNA fragment from the genomic locus. A cell is contacted with an oligomeric compound targeting the small non-coding RNA. A ChIP assay using the PCR primers and an antibody recognizing a heterochromatin-related protein is performed. Changes are analyzed in the outcome of the ChIP assay in a cell contacted with the oligomeric compound as compared to a cell not contacted with the oligomeric compound. A change in the outcome of the ChIP assay indicates that the small non-coding RNA influences binding of the heterochromatin-related protein at the genomic locus.

The present invention also provides a method of modulating epigenetic control of gene expression in a cell, tissue, or animal comprising contacting the cell, tissue, or animal with any of the compounds or compositions described herein. In some embodiments the cell can be a pluripotent stem cell.

The present invention also provides methods of modulating the expression of a heterochromatin-related protein in a cell, tissue, or animal comprising contacting the cell, tissue, or animal with any of the compounds or compositions described herein. In some embodiments the cell can be a pluripotent stem cell.

The present invention also provides methods of modulating chromosome segregation in a cell, tissue, or animal comprising contacting the cell, tissue, or animal with any of the compounds or compositions described herein.

The present invention provides oligomeric compounds comprising from about 8 to about 80 nucleobases wherein at least one nucleobase comprises a modification; at least an 8 nucleobase portion of the oligomeric compound is targeted to a small non-coding RNA that is cognate to or transcribed by a promoter, an enhancer, a centromeric region, a telomeric region, an origin of DNA replication, an imprinted locus, or a locus marked by dosage-compensation; and the small non-coding RNA regulates epigenetic control of gene expression. The compound can comprise from about 13 to about 30 nucleobases, from about 12 to about 50 nucleobases, or from about 15 to about 30 nucleobases, or from about 19 to about 23 nucleobases.

The small non-coding RNA can be produced in cis or in trans to the site it regulates. The small non-coding RNA can guide the activity of a CENP, INCENP, exosome/PM-Scl component, histone modifying enzyme, Polycomb group protein, or pseudouridylating enzyme, can regulate the expression of a gene encoding a CENP, INCENP, exosome/PM-Scl component, histone modifying enzyme, homeobox protein, or pseudouridylating enzyme, can regulate the binding of a kinetochore protein to a centromeric DNA region, can regulate the binding of a telomere-binding protein to a telomeric DNA region, can regulate the binding of an origin-recognition complex to an origin of DNA replication, can regulate dosage compensation, can regulate the formation, localization, or function of an exosome/PM-Scl complex or histone modifying complex, can mark one or more heterochromatic regions or heterochromatin proteins for modification, or can be cognate to a promoter or enhancer region within a genomic locus. The modification can be acetylation, deacetylation, phosphorylation, dephosphorylation, methylation, demethylation, ubiquitination, sumoylation, or pseudouridylation.

The present invention also provides oligomeric compounds comprising from about 17 to about 450 nucleobases wherein: at least one nucleobase comprises a modification; at least an 8 nucleobase portion of the oligomeric compound mimics a small non-coding RNA cognate to or transcribed by a promoter, an enhancer, a centromeric region, a telomeric region, an origin of DNA replication, an imprinted locus, or a locus marked by dosage-compensation; and the small non-coding RNA regulates epigenetic control of gene expression. The compound can comprise from about 110 to about 280 nucleobases, from about 50 to about 110 nucleobases, or from about 17 to about 25 nucleobases. The small non-coding RNA can be produced in cis or in trans to the site it regulates. The small non-coding RNA can guide the activity of a CENP, INCENP, exosome/PM-Scl component, histone modifying enzyme, Polycomb group protein, or pseudouridylating enzyme, can regulate the expression of a gene encoding a CENP, INCENP, exosome/PM-Scl component, histone modifying enzyme, homeobox protein, or pseudouridylating enzyme, can regulate the binding of a kinetochore protein to a centromeric DNA region, can regulate the binding of a telomere-binding protein to a telomeric DNA region, can regulate the binding of an origin-recognition complex to an origin of DNA replication, can regulate dosage compensation, can regulate the formation, localization, or function of an exosome/PM-Scl complex or histone modifying complex, can mark one or more heterochromatic regions or heterochromatin proteins for modification, or can be cognate to a promoter or enhancer region within a genomic locus. The modification can be acetylation, deacetylation, phosphorylation, dephosphorylation, methylation, demethylation, ubiquitination, sumoylation or pseudouridylation.

The present invention also provides compositions comprising any of the compounds described herein and a carrier or diluent. The carrier can be a pharmaceutically acceptable carrier.

The present invention also provides kits or assay devices comprising any of the compounds or compositions described herein.

The present invention also provides methods of arresting or delaying mitosis or meiosis in a cell, tissue, or animal comprising contacting the cell, tissue, or animal with any of the compounds or compositions described herein.

The present invention also provides methods of reducing spermatogenesis comprising contacting a male animal with any of the compounds or compositions described herein.

The present invention also provides methods of contraception comprising contacting a male animal undergoing spermatogenesis with any of the compounds or compositions described herein.

The present invention also provides methods of treating or preventing a disease or disorder associated with aberrant epigenetic control of gene expression comprising contacting an animal having or predisposed to having the disease or disorder with a therapeutically effective amount of any of the compounds or compositions described herein.

In the aforementioned methods, the small non-coding RNA can be a component of an exosome/PM-Scl complex or a component of a histone-modifying complex. The disease or disorder can be an autoimmune disorder, a result of a viral infection, a result of an active inflammatory response, or a result of aberrant regulation of gene activity (including hyperproliferation of cells) or gene dosage. The autoimmune disorder can be scleroderma, CREST syndrome, rheumatoid arthritis, diabetes, or systemic lupus erythematosus.

DESCRIPTION OF EMBODIMENTS

The present invention provides methods for determining whether an oligomeric compound that modulates degradation or translational suppression of a target nucleic acid (such as one which engages the RNase H pathway or the RNA interference pathway) causes undesirable alterations in the epigenetic control of gene expression. Such alterations can include heritable changes to gene expression such as the status of acetylation, methylation, and ubiquitination, among others; aberrant binding of, or interruption of binding of, a protein, protein complex or ribonucleoprotein complex to a genomic locus subject to epigenetic regulation. In preferred embodiments, the oligomeric compounds are used as therapeutic agents. The present invention further provides oligomeric compounds useful for modulating epigenetic processes, for example, heterochromatin formation and function, including those relying on mechanisms of action such as RNAi and dsRNA enzymes, as well as antisense and non-antisense mechanisms. As used herein, "translational suppression" means that there is a reduction in the translation of a protein encoded by a nucleic acid without a similar reduction in the amount of said target nucleic acid (i.e. the reduction in the amount of a protein is not directly tied to the degradation or cleavage of the mRNA encoding such protein).

The present invention additionally provides methods of determining whether a small non-coding RNA that is known to modulate the degradation or translational suppression of a target nucleic acid further modulates the epigenetic control of gene expression. For example, a small non-coding RNA such as an siRNA that is selected for its ability to inhibit the expression of its target gene through degradation of the target gene mRNA is tested for its ability to concomitantly modulate epigenetically controlled gene expression. Such testing includes determining, for example, whether the siRNA, in addition to inhibiting the expression of its target nucleic acid, influences methylation of one or more genomic loci, such that normal gene expression patterns are perturbed. This method provides a means for identifying small non-coding RNAs that specifically modulate the degradation or translation suppression of a target nucleic acid without deleteriously affecting the expression of epigenetically regulated genes. This method also provides a means for determining whether oligomeric compounds with either target or mimic endogenous microRNA further modulate the epigenetic control of gene expression.

The present invention also provides methods of a determining whether a small non-coding RNA influences methylation at a genomic locus. A genomic locus having homology to a small non-coding RNA is identified. Methylation-specific primers to amplify a DNA fragment from the genomic region are designed. A cell is contacted with an oligomeric compound targeting the small non-coding RNA. Methylation-specific amplification, such as PCR, is performed Whether there is a change in the methylation status of the genomic locus in cells contacted with the oligomeric compound as compared to cells not contacted with the oligomeric compound is determined. A change indicates that the small non-coding RNA influences methylation at the genomic locus.

The present invention also provides methods of a determining whether a small non-coding RNA influences binding of a heterochromatin-related protein at a genomic locus. A genomic locus having homology to a small non-coding RNA is identified. Amplification primers, such as PCR primers, are designed to amplify a DNA fragment from the genomic locus. A cell is contacted with an oligomeric compound targeting the small non-coding RNA. A ChIP assay, or other equivalent assay known to those skilled in the art, using the amplification primers and an antibody recognizing a hetero-chromatin-related protein is performed. Whether there is a change in the outcome of the ChIP assay in cells contacted with the oligomeric compound as compared to cells not contacted with the oligomeric compound is determined. A change indicates that the small non-coding RNA influences binding of the heterochromatin-related protein at the genomic locus.

Also provided are methods of screening for modulators of epigenetic control of gene expression, methods of modulating the expression of heterochromatin proteins, and methods of modulating the formation or function of heterochromatin in cells, tissues or animals comprising contacting said cells, tissues or animals with one or more of the compounds or compositions of the invention. Methods of modulating chromosome segregation, methods of arresting or delaying mitosis and/or meiosis, methods of inhibiting spermatogenesis, and methods of contraception are also set forth herein.

The present invention provides oligomeric compounds useful in, for example, the modulation of expression, levels or function of small non-coding RNAs cognate to or transcribed by heterochromatic regions subject to epigenetic regulation (i.e., gene promoters, enhancers, insulators, centromeres, telomeres, origins of DNA replication, imprinted loci, or loci marked by dosage-compensation), and which regulate the formation, assembly or function of heterochromatin in at least one of these regions. The present invention also provides oligomeric compounds that comprise at least one modification, wherein a portion of the oligomeric compound is targeted to or mimics a small non-coding RNA cognate to or transcribed by a gene promoter, enhancer, insulator, centromere, telomere, origin of DNA replication, imprinted locus, or locus marked by dosage-compensation, and which epigenetically regulates gene expression in at least one of these regions.

As used herein, the term "small non-coding RNA" is used to encompass, without limitation, a polynucleotide molecule ranging from about 17 to about 450 nucleotides in length, which can be endogenously transcribed or produced exogenously (chemically or synthetically), but is not translated into a protein. Small non-coding RNAs include isolated single-, double-, or multiple-stranded molecules, any of which may include regions of intrastrand nucleobase complementarity, wherein the regions are capable of folding and forming a molecule with fully or partially double-stranded or multiple-stranded character based on regions of perfect or imperfect complementarity. Examples of small non-coding RNAs include, but are not limited to, primary miRNA transcripts (also known as pri-pre-miRNAs, pri-mirs and pri-miRNAs, which range from about 70 nucleotides to about 450 nucleotides in length and often taking the form of a hairpin structure); pre-miRNAs (also known as pre-mirs and foldback miRNA precursors, which range from about 50 nucleotides to about 110 nucleotides in length); miRNAs (also known as microRNAs, Mirs, miRs, mirs, and mature miRNAs, and generally refer either to double-stranded intermediate molecules about 17 to about 25 nucleotides in length, or to single-stranded miRNAs, which may comprise a bulged structure upon hybridization with a partially complementary target nucleic acid molecule); siRNAs or mimics of pri-miRNAs, pre-miRNAs, miRNAs or siRNAs. Small non-coding RNAs can be endogenously transcribed in cells, or can be synthetic oligonucleotides, in vitro transcribed polynucleotides or nucleic acid oligomeric compounds expressed from vectors. Pri-miRNAs and pre-miRNAs, or mimics thereof, may be processed into smaller molecules.

As used herein, the term "miRNA precursor" is used to encompass, without limitation, primary RNA transcripts, pri-miRNAs and pre-miRNAs.

In some embodiments, small non-coding RNAs, or mimics thereof, comprise from about 70 to about 450 nucleobases in length. One having ordinary skill in the art will appreciate that this embodies oligomeric compounds of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449 or 450 nucleobases in length, or any range therewithin.

In some embodiments, small non-coding RNAs, or mimics thereof, comprise from about 110 to about 430 nucleobases in length, as exemplified above. In some embodiments, small non-coding RNAs, or mimics thereof, comprise from about 110 to about 280 nucleobases in length, as exemplified above. In some embodiments, small non-coding RNAs, or mimics thereof, comprise from about 50 to about 110 nucleobases in length, as exemplified above. In some embodiments, pre-miRNAs, or mimics thereof, comprise from about 60 to about 80 nucleobases in length, as exemplified above. In some embodiments, small non-coding RNAs, or mimics thereof, comprise from about 15 to about 49 nucleobases in length, as exemplified above. In some embodiments, miRNAs, or mimics thereof, comprise from about 17 to about 25 nucleobases in length, as exemplified above.

Thus, in accordance with the present invention, oligomeric compounds designed to mimic primary RNA transcripts (for example, pri-miRNAs) are from about 70 to about 450 monomeric subunits in length, or from about 110 to 430 subunits in length. Oligomeric compounds of the invention designed to mimic precursors of small non-coding RNAs (for example, the pre-miRNA products of the Drosha RNase) are from about 50 to about 110 monomeric subunits in length, or from about 60 to about 80 subunits in length. Oligomeric compounds of the invention designed to mimic mature miRNAs or siRNAs are from about 17 to about 25 monomeric subunits in length, and can be single- or double-stranded with either or both strands comprising from about 17 to about 25 subunits.

Oligomeric compounds of the invention modulate the levels, expression or function of small non-coding RNAs by hybridizing to a nucleic acid comprising or encoding a small non-coding RNA nucleic acid target resulting in alteration of normal function by, for example, facilitating destruction of the small non-coding RNA through cleavage, by sequestration, or by sterically occluding the function of the small non-coding RNA. Further, modified synthetic oligomeric compounds of the present invention may be designed to mimic endogenous small non-coding RNAs. These modifications include, but are not limited to, modifications which improve the pharmacokinetic or pharmacodynamic properties, binding affinity, stability, charge, localization or uptake of the oligomeric compound. Synthetic mimics can therefore act as replacements for small non-coding RNAs, as competitive inhibitors of naturally occurring small non-coding RNAs or as delivery systems wherein the mimic construct contains one or more functional components.

As used herein, the terms "target nucleic acid," "target RNA," "target RNA transcript" or "nucleic acid target" are used to encompass any nucleic acid capable of being targeted including, without limitation, RNA (including microRNAs, stRNAs, small nuclear RNAs, small nucleolar RNAs, small ribosomal RNAs, small hairpin RNAs, endogenous antisense RNAs, guide RNAS, tiny noncoding RNAs, small single or double stranded RNAs that are encoded by heterochromatic repeats at centromeres or other chromosomal origin, and any precursors thereof). These nucleic acid targets can be coding or non-coding sequences; pre-mRNAs or mRNAs; single- or double-stranded, or single-stranded with partial double-stranded character; may occur naturally within introns or exons of messenger RNAs (mRNAs), ribosomal RNAs (rRNAs), or transfer RNAs (tRNAs); and can be endogenously transcribed or exogenously produced.

In some embodiments of this invention, modulation of small non-coding RNA levels, expression or function is achieved via oligomeric compounds which target a further RNA associated with the particular small non-coding RNA. This association can be a physical association between that RNA and the particular small non-coding RNA such as, but not limited to, in an RNA or ribonucleoprotein complex. This association can also be within the context of a biological pathway, such as but not limited to, the regulation of levels, expression or function of a protein-encoding mRNA or its precursor by a small non-coding RNA. As such, the invention provides for modulation of the levels, expression or function of a target nucleic acid where the target nucleic acid is a messenger RNA whose expression levels and/or function are associated with one or more small non-coding RNAs. The messenger RNA function or processing may be disrupted by degradation through an antisense mechanism, including but not limited to, RNA interference, or RNase H, as well as other mechanisms wherein nucleic acid structures are recognized and degraded, cleaved, sterically occluded, sequestered or otherwise rendered inoperable.

The compounds or compositions of the present invention may also interfere with the function of endogenous RNA molecules. The functions of RNA to be interfered with can include, for example, nuclear events such as replication or transcription as the compounds of the present invention could target or mimic small non-coding RNAs active in these cellular processes. Replication and transcription, for example, can be from an endogenous cellular template, a vector, a plasmid construct or otherwise. The functions of RNA to be interfered with can include cytoplasmic events such as translocation of the RNA to a site of protein translation, translocation of the RNA to sites within the cell which are distant from the site of RNA synthesis, translation of protein from the RNA, splicing of the RNA to yield one or more RNA species, RNA signaling and regulatory activities, and catalytic activity or complex formation involving the RNA which may be engaged in or facilitated by the RNA as the compounds of the present invention could target or mimic small non-coding RNAs active in these cellular processes.

In the context of the present invention, "modulation" and "modulation of expression" mean either an increase (stimulation) or a decrease (inhibition) in the amount or levels of a small non-coding RNA, nucleic acid target, an RNA or protein associated with a small non-coding RNA, or a downstream target of the small non-coding RNA (e.g., a mRNA representing a protein-coding nucleic acid that is regulated by a small non-coding RNA). Inhibition is a suitable form of modulation and small non-coding RNA is a suitable target nucleic acid.

In the context of the present invention, "modulation of function" means an alteration in the function of the small non-coding RNA or an alteration in the function of any cellular component with which the small non-coding RNA has an association or downstream effect.

The present invention provides, inter alia, oligomeric compounds and compositions containing the same wherein the oligomeric compound includes one or more modifications that render the compound capable of supporting modulation of the levels, expression or function of the small non-coding RNA by a degradation or cleavage mechanism.

The present invention also provides oligomeric compounds and compositions containing the same wherein the oligomeric compound includes one or more modifications that render the compound capable of blocking or interfering with the levels, expression or function of one or more small non-coding RNAs by steric occlusion.

The present invention also provides oligomeric compounds and compositions containing the same wherein the oligomeric compound includes one or more modifications or structural elements or motifs that render the compound capable of mimicking or replacing one or more small non-coding RNAs.

Oligomeric Compounds

In the context of the present invention, the term "oligomeric compound(s)" refers to polymeric structures which are capable of hybridizing to at least a region of a small non-coding RNA molecule or a target of small non-coding RNAs, or polymeric structures which are capable of mimicking small non-coding RNAs. The term "oligomeric compound" includes, but is not limited to, compounds comprising oligonucleotides, oligonucleosides, oligonucleotide analogs, oligonucleotide mimetics and combinations of these. Oligomeric compounds also include, but are not limited to, antisense oligomeric compounds, antisense oligonucleotides, siRNAs, alternate splicers, primers, probes and other compounds that hybridize to at least a portion of the target nucleic acid. Oligomeric compounds are routinely prepared linearly but can be joined or otherwise prepared to be circular and may also include branching. Separate oligomeric compounds can hybridize to form double stranded compounds that can be blunt-ended or may include overhangs on one or both termini. In general, an oligomeric compound comprises a backbone of linked monomeric subunits where each linked monomeric subunit is directly or indirectly attached to a heterocyclic base moiety. The linkages joining the monomeric subunits, the sugar moieties or sugar surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers generally to an oligomer or polymer of ribonucleic acid (RNA) or deoxyribonucleic acid (DNA). This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts. In addition to the modifications described above, the nucleosides of the oligomeric compounds of the invention can have a variety of other modifications. Additional nucleosides amenable to the present invention having altered base moieties and or altered sugar moieties are disclosed in U.S. Pat. No. 3,687,808 and PCT application PCT/US89/02323.

For nucleotides that are incorporated into oligonucleotides of the invention, these nucleotides can have sugar portions that correspond to naturally occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar.

Altered base moieties or altered sugar moieties also include other modifications consistent with the spirit of this invention. Such oligomeric compounds are best described as being structurally distinguishable from, yet functionally interchangeable with, naturally occurring or synthetic unmodified oligonucleotides. All such oligomeric compounds are comprehended by this invention so long as they function effectively to mimic the structure or function of a desired RNA or DNA oligonucleotide strand.

A class of representative base modifications include tricyclic cytosine analog, termed "G clamp" (Lin et al., J. Am. Chem. Soc., 1998, 120, 8531). This analog can form four hydrogen bonds with a complementary guanine (G) by simultaneously recognizing the Watson-Crick and Hoogsteen faces of the targeted G. This G clamp modification when incorporated into phosphorothioate oligomeric compounds, dramatically enhances potencies as measured by target reduction in cell culture. The oligomeric compounds of the invention also can include phenoxazine-substituted bases of the type disclosed by Flanagan et al., Nat. Biotechnol., 1999, 17, 48-52.

The oligomeric compounds in accordance with this invention comprise from about 8 to about 80 monomeric subunits (i.e. from about 8 to about 80 linked nucleosides or nucleobases). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 subunits in length, or any range therewithin.

In one embodiment, the oligomeric compounds of the invention are about 12 to about 50 monomeric subunits (or nucleobases) in length, as exemplified above.

In one embodiment, the oligomeric compounds of the invention are about 13 to about 80 monomeric subunits (or nucleobases) in length, as exemplified above.

In one embodiment, the oligomeric compounds of the invention are about 15 to about 30 monomeric subunits (or nucleobases) in length, as exemplified above.

As used herein, the term "about" means±5% of the variable thereafter; this value can be rounded up to the nearest integer. Thus, for oligomeric compounds smaller than 20 monomeric subunits in length, "about" means±5% which is rounded up to equal ±one monomeric subunit.

In the context of this invention, "hybridization" means the pairing of complementary strands of oligomeric compounds. In the present invention, the mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under various circumstances.

An oligomeric compound of the invention is "specifically hybridizable" when association of the compound with the target nucleic acid interferes with the normal function of the target nucleic acid to alter the activity, disrupt the function, or modulate the level of the target nucleic acid, and there is a sufficient degree of complementarity to avoid non-specific binding of the oligomeric compound to non-target nucleic acid sequences under conditions in which specific hybridization is desired, i.e., under physiological conditions in the case of in vivo assays or therapeutic treatment, and under standard assay conditions in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated. One having ordinary skill in the art will understand variability in the experimental protocols and be able to determine when conditions are optimal for stringent hybridization with minimal non-specific hybridization events.

While not wishing to be bound by theory, it is believed that, under physiological conditions, miRNAs are able to specifically hybridize to specific sets of target nucleic acids, in spite of the presence of mismatched basepairs and imperfect complementarity between the miRNAs and their target nucleic acids. Target nucleic acids include genomic loci. Thus, the phrase "sufficient degree of complementarity to avoid non-specific binding" is herein used to refer to the set of conditions (percent complementarity, G:C content of each of the hybridizing sequences, temperature and salt conditions, and the presence of structured regions) which allow hybridization to occur and imitate a natural physiological setting or activity. An miRNA is considered to have homology to a genomic locus when there is a sufficient degree of complementarity to avoid non-specific binding.

"Complementary," as used herein, refers to the capacity for precise pairing between two monomeric subunits in the oligomeric compound or target nucleic acid regardless of where the two are located. For example, if a monomeric subunit at a certain position of an oligomeric compound is capable of hydrogen bonding with a monomeric subunit at a certain position of a target nucleic acid, then the position of hydrogen bonding between the oligomeric compound and the target nucleic acid is considered to be a complementary position. The oligomeric compound and the target nucleic acid are "substantially complementary" to each other when a sufficient number of complementary positions in each molecule are occupied by monomeric subunits that can hydrogen bond with each other. Thus, the term "substantially complementary" is used to indicate a sufficient degree of precise pairing over a sufficient number of monomeric subunits such that stable and specific binding occurs between the oligomeric compound and a target nucleic acid.

Generally, an oligomeric compound is "antisense" to a target nucleic acid when, written in the 5' to 3' direction, it comprises the reverse complement of the corresponding region of the target nucleic acid. "Antisense compounds" are also often defined in the art to comprise the further limitation of, once hybridized to a target, being able to induce or trigger a reduction in target gene expression.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization (e.g., a bulge, a loop structure or a hairpin structure).

In some embodiments of the invention, the oligomeric compounds comprise at least 50%, at least 60%, at least 70%, at least 75%, at least 80%, or at least 85% sequence complementarity to a target region within the target nucleic acid. In other embodiments of the invention, the oligomeric compounds comprise at least 90% sequence complementarity to a target region within the target nucleic acid. In other embodiments of the invention, the oligomeric compounds comprise at least 95% or at least 99% sequence complementarity to a target region within the target nucleic acid. For example, an oligomeric compound in which 18 of 20 nucleobases of the oligomeric compound are complementary to a target sequence would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In some embodiments of the invention, the oligomeric compounds act as mimics or replacements for small non-coding RNAs. In this case, the oligomeric compounds of the invention can comprise at least 70% sequence identity to a small non-coding RNA or a region thereof. In some embodiments the oligomeric compounds of the invention can comprise at least 90% sequence identity and in some embodiments can comprise at least 95% sequence identity to a small non-coding RNA or a region thereof.

In additional embodiments of the invention, the oligomeric compounds that target or mimic small non-coding RNAs include oligomeric compounds that comprise at least 70%, at least 75%, at least 80%, at least 85%, at least 90%, at least 95%, or a least 99% identity to an oligomeric compound of the invention. For example, a first oligomeric compound having 20 nucleobases shares 90% identity with a second oligomeric compound having 18 of the 20 nucleobases present in the first oligomeric compound.

It is understood that embodiment related to complementarity, hybridization or pairing between an oligomeric compound and its target nucleic acid is equally applicable to complementarity between a miRNA and its target nucleic acid, which includes genomic loci.

"Targeting" an oligomeric compound to a particular nucleic acid molecule, in the context of this invention, can be a multistep process. The process usually begins with the identification of a target nucleic acid whose levels, expression or function is to be modulated. This target nucleic acid may be, for example, a mRNA transcribed from a cellular gene whose expression is associated with a particular disorder or disease state, a small non-coding RNA or its precursor, or a nucleic acid molecule from an infectious agent.

The targeting process usually also includes determination of at least one target region, segment, or site within the target nucleic acid for the interaction to occur such that the desired effect, e.g., modulation of levels, expression or function, will result. Within the context of the present invention, the term "region" is defined as a portion of the target nucleic acid having at least one identifiable sequence, structure, function, or characteristic. Within regions of target nucleic acids are segments. "Segments" are defined as smaller or sub-portions of regions within a target nucleic acid. "Sites," as used in the present invention, are defined as specific positions within a target nucleic acid. The terms region, segment, and site can also be used to describe an oligomeric compound of the invention such as for example a gapped oligomeric compound having three separate segments. Targets of the present invention include both coding and non-coding nucleic acid sequences. Coding nucleic acid sequences include the translation initiation codon or start codon, the open reading frame or coding region, and the translation termination codon or stop codon. Non-coding nucleic acid sequences include the 5' untranslated region (5'UTR), the 3' untranslated region (3'UTR), and introns. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also target sites. mRNA transcripts produced via the process of splicing of two (or more) mRNAs from different gene sources are known as "fusion transcripts." It is also known that introns can be effectively targeted using oligomeric compounds targeted to, precursor molecules for example, pre-mRNA.

It is also known in the art that alternative RNA transcripts can be produced from the same genomic region of DNA. These alternative transcripts are generally known as "variants" and include pre-mRNA variants, mRNA variants, alternative start variants, alternative stop variants, and polyA variants. Within the context of the invention, the types of variants described herein are also target nucleic acids.

Certain non-coding RNA genes are known to produce functional RNA molecules with important roles in diverse cellular processes. Such non-translated, noncoding RNA molecules can include ribosomal RNAs, tRNAs, snRNAs, snoRNAs, tncRNAs, rasiRNAs, short hairpin RNAs (shRNAs), short temporal RNAs (stRNAs), short hairpin RNAs (shRNAs), siRNAs, miRNAs and smnRNAs. These non-coding RNA genes and their products are also suitable targets of the compounds of the invention. Such cellular processes include transcriptional regulation, translational regulation (including suppression of translation), developmental timing, viral surveillance, immunity, chromosome maintenance, ribosomal structure and function, gene imprinting, subcellular compartmentalization, pre-mRNA splicing, and guidance of RNA modifications. RNA-mediated processes are now also believed to direct heterochromatin formation, genome rearrangements, cellular differentiation and DNA elimination. Therefore, non-translated, non-coding RNAs are suitable target nucleic acids.

Of the 201 different expressed RNA sequences potentially encoding novel small non-messenger species (smnRNAs), several have been assigned to the snoRNA class of nucleolar localized molecules known to act as guide RNAs for rRNA modification, whereas others are predicted to direct modification within the U2, U4, or U6 small nuclear RNAs (snRNAs). Some of these newly identified smnRNAs remained unclassified and have no identified RNA targets. It was suggested that some of these RNA species may have novel functions previously unknown for snoRNAs, namely the regulation of gene expression by binding to and/or modifying mRNAs or their precursors via their antisense elements (Huttenhofer et al., Embo J., 2001, 20, 2943-2953). Therefore, these smnRNAs are also suitable targets for the compounds of the present invention.

The locations on the target nucleic acid to which compounds and compositions of the invention hybridize are herein referred to as "suitable target segments." As used herein, the term "suitable target segment" is defined as at least an 8-nucleobase portion of a target region to which oligomeric compound is targeted. Alternatively, a suitable target segment is defined as at least a 12-nucleobase portion of a target region to which an oligomeric compound is targeted. In another aspect, a suitable target segment is defined as at least a 15-nucleobase portion of a target region.

Once one or more targets, target regions, segments or sites have been identified, oligomeric compounds are designed to be sufficiently complementary to the target, i.e., hybridize sufficiently well and with sufficient specificity, to give the desired effect. The desired effect may include, but is not limited to, modulation of the levels, expression or function of the target.

In accordance with the present invention, single stranded oligomeric compounds can be designed to target or mimic one or more specific small non-coding RNAs. These oligomeric compounds can be of a specified length, for example from 8 to 80, 12 to 50, 13 to 80, 15 to 30, 13 to 30, 70 to 450, 110 to 430, 110 to 280, 50 to 110, 60 to 80, 15 to 49, 17 to 25 or 19 to 23 nucleotides long and have one or more modifications.

In accordance with one embodiment of the invention, double-stranded oligomeric compounds (duplexes) comprising, as the antisense strand, the single-stranded oligomeric compounds of the present invention, and the fully or partially complementary sense strand, can be designed to modulate the levels, expression or function of one or more small non-coding RNAs or small non-coding RNA targets. One or both termini of the duplex strands may be modified by the addition of one or more natural or modified nucleobases to form an overhang. The sense strand of the duplex may be designed and synthesized as the complement of the antisense strand and may also contain modifications or additions to either terminus. For example, in one embodiment, both strands of the duplex would be complementary over the central region of the duplex, each having overhangs at one or both termini.

For the purposes of this invention, the combination of an antisense strand and a sense strand, each of which can be of a specified length (for example from 8 to 80, 12 to 50, 13 to 30, 13 to 80, 15 to 30, 15 to 49, 17 to 25 or 19 to 23 subunits long), is identified as a complementary pair of oligomeric compounds. This complementary pair of oligonucleotides can include additional nucleotides on either of their 5' or 3' ends. They can include other molecules or molecular structures on their 3' or 5' ends, such as a phosphate group on the 5' end, or non-nucleic acid moieties conjugated to either terminus of either strand or both strands. One group of compounds of the invention includes a phosphate group on the 5' end of the antisense strand compound. Other compounds also include a phosphate group on the 5' end of the sense strand compound. Some compounds include additional nucleotides such as a two base overhang on the 3' end as well as those lacking overhangs.

In some embodiments, a single-stranded hairpin oligomeric compound may be designed comprising the antisense portion as a first region and the sense portion as a second region. The first and second regions can be linked together by either a nucleotide linker (a string of one or more nucleotides that are linked together in a sequence) or by a non-nucleotide linker region or by a combination of both a nucleotide and non-nucleotide structure. In any of these structures, the oligomeric compound, when folded back on itself, would form at least a partially complementary structure at least between a portion of the first region, the antisense portion, and a portion of the second region, the sense portion.

The oligomeric compounds targeting or mimicking the small non-coding RNAs may regulate dosage compensation, or may regulate the binding of a protein to a heterochromatic region, such as a kinetochore protein to a centromeric DNA region, a telomere-binding protein to a telomeric DNA region, a transcription factor to a gene promoter, enhancer, or insulator, or an origin-recognition complex to an origin of DNA replication.

In the context of the present invention, the term "epigenetic" means a difference in gene function or phenotype not attributable to a change in the primary DNA sequence. Epigenetic gene regulation relies on mechanisms that reversibly modify or "mark" the DNA itself or the chromatin into which DNA is packaged, thereby influencing the binding of transcription factors, proteins bearing methyl-CpG-binding domains (MBDs), or other chromatin-associated proteins. Mammalian cellular differentiation and development depend on stable and heritable epigenetic switches, such as X-chromosome inactivation and imprinting, by cytosine DNA methylation. Epigenetic marks such as methylation are also believed to play a role in tissue-specific gene repression and silencing of parasitic sequences, and methylation changes have been implicated in malignant transformation of cancer cells (Riggs et al., Proc. Natl. Acad. Sci., 2004, 101, 45; and Schubeler et al., Mol. Cell. Biol., 2000, 20, 9103-12).

In the context of the present invention, the phrase "epigenetic control of gene expression" and "epigenetic regulation of gene expression" are used interchangeably herein and are used to refer to the regulation of expression of genes by means of marking DNA or heterochromatin protein complexes in gene regulatory regions via modifications such as methylation, demethylation, acetylation, deacetylation, phosphorylation, dephosphorylation, ubiquitination, sumoylation or pseudouridylation. It is believed that small non-coding DNAs may be involved in the epigenetic control of gene expression by hybridizing to gene regulatory regions such as enhancers, promoters, or insulators, for example, and either guiding or inhibiting the activity of methyltransferases, acetylases, deacetylases, etc.

While not wishing to be bound by theory, examples of proteins believed to be involved in heterochromatin formation (also referred to herein as "heterochromatin-related proteins") include, but are not limited to, the silent information regulator (SIR) family of proteins, SIRT1, the SWI/SNF family of proteins, bromodomain proteins, nucleosome remodeling factor (NURF), BRD 1, BRG1, SUV39H1, histone deacetylases (HDACs), the MYST-like acetyltransferases, MOZ/ZNF 220, MBD proteins, and the polycomb group (PcG) proteins.

Examples of MBD proteins include, but are not limited to, methyl-CpG-binding domain proteins 1-4 (MBD1, MBD2, MBD3, and MBD4); methyl-CpG-binding domain protein 3-like-1 and -2 (MBD3L1 and MBD3L2); methyl-CpG-binding protein 2 (MeCP2); Chromobox homolog 5 (CBX5) (also known as heterochromatin protein-1 and HP1-alpha); Chromobox homolog 1 (CBX1) (also known as HP1-beta); KIAA187; Methyl-CpG binding protein 5 (also known as KIAA1461); Bromodomain adjacent to zinc finger domain 2A (also known as BAZ2A, Transcription termination factor-I interacting protein 5, TFF-I interacting protein 5, Tip5, and hWALp3); bromodomain adjacent to zinc finger domain, 1A (BAZ1A); BAZ2B; SET domain protein, bifurcated, 1 (SETDB1); and chronic lymphocytic leukemia deletion region gene 8 (CLLD8) (also known as SET domain protein, bifurcated, 2 (SETDB2)).

As used herein, "chromatin" is a general term referring to nucleoprotein complexes which compact and organize great lengths of cellular genetic material to contain it within cells. At the primary level of chromatin organization in the nucleus of eukaryotic cells is the nucleosome, in which double-stranded DNA (dsDNA) is wound approximately twice around a core of conserved histone or histone-like proteins. Higher-order chromatin organization involves further compaction of nucleosomes around additional chromatin-associated proteins, and employs an entourage of chromatin assembly factors.

The term "heterochromatin" is used to mean the subset of chromatin that is most densely compacted and is generally transcriptionally silent; however, heterochromatin may participate in other cellular functions. As used herein, the phrase "heterochromatin function" can mean transcriptional repression of genes; subcellular sequestration, compartmentalization, and/or silencing of particular genes or genomic DNA regions; stabilization of repetitive DNA sequences and inhibiting recombination between homologous repeats; silencing of parasitic DNA; or can refer to the activities of kinetochores or telomeres, such as microtubule attachment, sister chromatid adhesion and separation, chromosome segregation through mitosis and/or meiosis, cell-cycle checkpoint surveillance and coordination of cell division, maintenance of DNA integrity at chromosome ends.

As used herein, "euchromatin" generally refers to the more extended chromatin domains that are often transcriptionally active, accessible portions of the genome.

As used herein, the phrases "heterochromatin formation" and "heterochromatin assembly" mean the recruitment of heterochromatin proteins into nucleoprotein complexes with DNA sequences in regions considered to be heterochromatic, such as telomeres, centromeres, origins of DNA replication, certain temporally- and/or developmentally-regulated or tissue-specific promoters or enhancers, and loci subject to dosage compensation regulation. While not wishing to be bound by theory, one example of a family of developmentally regulated promoters includes, but is not limited to, genes regulated by the homeobox family of transcription factors. Additionally, origins of DNA replication are believed to be temporally-regulated. The origin recognition complex (ORC) is a multisubunit complex of proteins widely conserved, from yeast to metazoans, which binds origins of DNA replication and is required for chromosomal DNA replication. Furthermore, to maintain genome stability, the activity of "licensing factors" ensures that DNA is replicated only once per cell cycle. The processes of heterochromatin formation and DNA replication are linked, and may involve heterochromatin protein 1 (HP1) (Shareef et al., Mol. Biol. Cell, 2001, 12, 1671-85).

Furthermore, a large percentage of small RNAs cloned from the fission yeast, *S. pombe*, were found to have perfect homology to portions of the centromere region in this organism (Reinhart et al., Science, 2002, 297, 1831), and it was shown that genes involved in the RNA interference (RNAI) pathway are required for pericentromere heterochromatin formation and chromosome segregation (Dawe, Plant Cell, 2003, 15, 297-301; and Volpe et al., Science, 2002, 297, 1833-7).

The RNA-induced Initiation of Transcriptional gene Silencing (RITS) complex is a ribonucleoprotein complex involved in heterochromatin assembly. In fission yeast, the RITS complex includes, but is not necessary limited to, the chromodomain protein, Chp1, that binds centromeres and the *S. pombe* Argonaute homolog (Ago1) which plays a role in RNAi, and the Tas3 protein, as well as small RNAs that require Dicer for their production. These small RNAs are homologous to centromeric repeats and are required for the localization of the RITS complex to heterochromatic domains, as well as for the methylation of H3 K9 and Swi6 binding to centromeric chromatin (Verdel et al., Science, 2004, 203, 672-6; and Ekwall, Mol. Cell, 2004, 13, 304-5). While not wishing to be bound by theory, it is believed that a similar ribonucleoprotein complex and small non-coding RNAs are involved in epigenetic gene silencing at specific chromosomal loci in humans, and that this complex may contain small non-coding RNA molecules amenable to targeting with the oligomeric compounds of the present invention. Consequently, one embodiment of the invention includes oligomeric compounds that target or mimic RNA components of the RITS complex. Thus, as described herein, small non-coding RNAs are likely involved in the regulation or licensing of heterochromatin assembly at specific regions such as centromeres, telomeres, and origins of DNA replication, and oligomeric compounds targeting or mimicking these small non-coding RNAs may be used to modulate heterochromatin assembly at specific regions within centromeres, telomeres, and origins of DNA replication, thereby affecting their activities.

In the context of this invention, the terms "centromere" or "centromeric DNA" means the genetic locus or cis-acting DNA sequence required for chromosome segregation during mitosis and/or meiosis. For example, eukaryotic centromere regions are composed of multiple spatial and functional domains, and yet these centromeric DNA sequences are not evolutionarily conserved between species. Despite this lack of conservation in centromeric DNA sequence, in higher eukaryotes, (A+T) -rich and/or repetitive satellite DNA is generally believed to be a substrate for kinetochore nucleation, association of a highly conserved centromere-binding kinetochore proteins, and subsequent spindle microtubule attachment.

In the present invention, the terms "kinetochore" or "kinetochore proteins" are used to refer to the nucleoprotein complex that assembles upon centromeric DNA to form the spindle attachment site for chromosome segregation during mitosis and/or meiosis. The term "kinetochore complex" refers to this nucleoprotein complex of centromeric DNA and the associated kinetochore proteins.

As used herein, the term "CENP" means centromere protein or centromeric DNA-binding protein. Examples of CENPs include, but are not limited to, CENP-A, CENP-B, CENP-C, CENP-D, CENP-E, CENP-F, CENP-G, CENP-H, and CENP-I. The founding members of the CENP family of human centromere proteins, CENP-A, CENP-B, and CENP-C, were originally identified using autoimmune sera from patients with scleroderma, particularly the calcinosis, Raynaud's phenomenon, esophageal dysmotility, sclerodactyl), and telangiectasia (CREST) syndrome (Earnshaw et al., J. Clin. Invest., 1986, 77, 426-30). CENP-A is a histone H3-like protein believed to be involved in the nucleosomal packaging of centromeric DNA. CENP-B is an 80 kDa protein that binds a 17-basepair (bp) motif known as the CENP-B box, which is present in human alpha-satellite and mouse minor satellite DNA and is reported to be a cis-element for centromere-specific nucleosome assembly (Pietras et al., Nucl. Acids Res., 1983, 11, 6965-83; Earnshaw et al., J. Clin. Invest., 1986, 77, 426-30; and Tanaka et al., EMBO J., 2001, 20, 6612-8). CENP-E, as well as CENP-B antisera were shown to bind to a functional centromeric sequence associated with the minor satellite DNA in mice, and demethylation of the minor satellite sequences resulted in a redistribution of the CENP-B protein, suggesting that methylation may play a role in determining the binding of centromere proteins and organizing kinetochore structure and/or activity (Mitchell, et al., J. Cell Sci., 1996, 109, 2199-2206). In fission yeast, a stepwise model for the formation of centromeric heterochromatin involves coordinated activity of histone deacetylases (HDACs) in the deacetylation of Histone H3 K9 and K14 residues, and subsequent methylation of H3 K9 by histone methyltransferases (HMTases), with the centromeric DNA-binding activities of CENP-B homologs (Nakagawa et al., Genes Devel., 2002, 16, 1766-78). Additionally, CENP-B-like proteins (human jerky-like protein, and the Tigger1 and Tigger2 transposases), have been identified (Moore et al., Epilepsy Res., 2001, 46, 157-67; and Smit et al., Proc. Natl. Acad. Sci., 1996, 93, 1443-8).

As used herein, the term "INCENP" means inner centromere protein (INCENP). Kinetochores comprise both constitutive proteins that are associated with centromeric DNA throughout the cell-cycle and transient proteins that are present at various stages. INCENP localizes to the centromere at early mitosis but subsequently relocates to the spindle midzone at the metaphase to anaphase transition and is an early component of the cleavage furrow, thus it is known as a chromosomal passenger protein and is believed to have a role in cytokinesis (Eckley et al., J. Cell Biol., 1997, 136, 1169-83). Phenotypes associated with the perturbation of INCENP function include those that are consistent with a defect in the modulation of microtubule dynamics that severely affects chromosome segregation and results in poorly resolved chromatin masses, aberrant karyokinesis and internuclear bridge formation (Cutts et al., Hum. Mol. Genet., 1999, 8, 1145-55).

As used herein, the term "telomeric DNA" means the genetic locus or cis-acting DNA sequence, usually consisting of short, tandemly repeated DNA sequences loosely conserved in eukaryotes, which is responsible for maintenance of cellular replicative capacity and genomic integrity at DNA ends during chromosome replication. The terms "telomere" or "telomere complex" refer to the nucleoprotein complex that assembles upon and includes the telomeric DNA. Telomeres are structures at the ends of eukaryotic chromosomes that are involved in maintaining chromosome length during the process of DNA replication, as well as in positioning of chromosomes in the nucleus, transcriptional silencing. For example, mammalian telomeres consist of TTAGGG repeats, telomeric repeat binding factor (TRF), and other proteins, resulting in a protective structure at chromosome ends. Examples of proteins involved in telomere complexes include, but are not limited to, Ku70, Ku80, Dyskerin (DKC), TRF, and WRN. Human Werner syndrome protein (WRN) is a member of the RecQ helicase family and contains 3'→5' helicase and 3'→5' exonuclease activities. Recently, the exonuclease activity of WRN was shown to be greatly stimulated by the human Ku heterodimer protein (comprising the Ku70 and Ku80 proteins). Another example of a protein involved in the telomere complex is telomerase, a ribonucleoprotein which contains telomerase protein component 1 (TEP1) and the telomerase RNA component (TERC), and which, in vitro, recognizes a single-stranded G-rich telomere primer and adds multiple telomeric repeats to its 3-prime end by using an RNA template. It is believed that telomerase may have a role in de novo formation of telomeres.

In the present invention the phrase "origins of DNA replication" refers to the genetic loci at which DNA replication initiates and to which origin recognition complexes (ORCs) bind. In eukaryotes, the initiation of DNA replication is regulated by the ordered assembly of DNA-protein complexes on origins of DNA replication. Examples of ORC proteins include, but are not limited to, ORC1L, ORC2L, ORC3L, ORC4L, ORC5L, ORC5T, ORC6L, CDC18L, CHK2, CDK2, CDC45, NBS1 and RFC1. The WRN RecQ-like helicase protein may also be involved in origin recognition complexes.

As used herein, "hyperproliferative disorder" means a disease or disorder characterized by cell growth that is independent of normal regulatory mechanisms (e.g., loss of contact inhibition, loss of cell cycle checkpoint control, insufficient apoptosis). Hyperproliferative disorders include cancers.

As used herein, "autoimmune disorder" means a disease characterized by the presence of high levels of circulating autoantibodies that recognize intracellular "self" proteins, nucleic acids, or evolutionarily conserved molecules in an organism; these autoantibodies result in the immune attack of one or more organ systems.

In one embodiment, the invention provides an oligomeric compound/protein composition. This composition has both an oligomeric compound component and a protein component. The oligomeric compound component comprises at least one oligomeric compound, either the antisense or the sense oligomeric compound. The protein component of the composition can comprise at least one protein that forms heterochromatin at a centromere, a telomere, an origin of DNA replication, an imprinted locus, or a locus marked by dosage compensation, or is a component of an exosome, or of the RITS complex. The oligomeric compound component can also comprise both antisense and sense strand oligomeric compounds.

Within the context of the present invention, the term "region" is defined as at least a fragment of the nucleic acid target or oligomeric compound having at least one identifiable structure, function, or characteristic. Regions can include, but are not limited to, fragments of the nucleic acid target or oligomeric compound having 10 to 50, 10 to 70, 13 to 80, or 13 to 110 subunits. Within regions of nucleic acid targets or oligomeric compounds are segments. "Segments" are defined as smaller or sub-portions of regions 5 to 50, or 8 to 80 subunits in length within a nucleic acid target or oligomeric compound. "Sites," as used in the present invention, are defined as positions within a nucleic acid target or oligomeric compound. The terms region, segment, and site can also be used to describe an oligomeric compound of the invention such as for example a gapped oligomeric compound having three separate segments.

The oligomeric compounds targeting or mimicking the small non-coding RNAs may be cognate to a promoter or enhancer region within a genomic locus. Within the context of the present invention, the term "cognate" refers to the ability of a small non-coding RNA or an oligomeric compound to hybridize with a nucleic acid in a cell. The nucleic acid can be either strand of a double-stranded genomic DNA sequence, or it can be an RNA transcript produced from genomic DNA sequence. An oligomeric compound of the invention is "cognate to" a target nucleic acid when the compound has a nucleobase sequence that is sufficiently homologous or identical to the nucleic acid sequence of an endogenous nucleic acid sequence in the cell, such that the oligomeric compound cognate to the target nucleic acid can inhibit the normal function of the target nucleic acid, compete with its activity, or disrupt its function. For example, small non-coding RNAs cognate to genomic DNA regions at centromeres, telomeres, origins of replication, imprinted loci, or loci marked by dosage compensation are believed to hybridize to nucleic acids in regions within or transcribed by gene coding sequences, promoters, enhancers, or other regulatory regions of genes, as well as sites of heterochromatin formation. For example, oligomeric compounds cognate to the telomerase RNA may affect the function of sequences within telomeric DNA.

Small non-coding RNAs may enhance or suppress DNA methylation. DNA methylation can occur on cytosine residues, which may or may not reside within CpG islands, but may also occur on adenine, guanine, thymine, or uracil residues (comprising, for example, 3-methyladenine (3MeA), or 7-methylguanine (7MeG) nucleobases).

Double-stranded or structured small non-coding RNAs may act as decoys (for example, titrating transcription factor complexes away from promoters, enhancers or other gene regulatory sequences), thereby affecting transcriptional control of genomic DNA sequences. Recently, a small, non-coding dsRNA was reported to play a role in mediating neuronal differentiation. The sequence defined by this dsRNA was the repressor element 1/neuron-restrictive silencer element (RE1/NRSE), which is a target site in genes regulated by NRSF/REST, a negative transcriptional regulator that restricts neuronal gene expression to neurons. The NRSE dsRNA was found to trigger gene expression of neuron-specific genes through interaction with NRSF/REST transcriptional machinery, resulting in the transition from neural stem cells with neuron-specific genes silenced by NRSF/REST into cells with neuronal identity that can express neuronal genes. This effect appears to be mediated through a dsRNA/protein interaction, rather than through a siRNA or miRNA mechanism of action (Kuwabara, et al., Cell, 2004, 116, 779-93).

Some examples of promoters include, but are not limited to, genomic DNA sequences up to 10-kb upstream from the following genes: E-cadherin (CDH1), H-cadherin (CDH13), caspase-8, retinoic acid receptor beta-2 (RARβ), tissue inhibitor of metalloproteinase 3 (TIMP-3), $O^6$-methylguanine-DNA-methyltransferase (MGMT), p14$^{ARF}$, death-associated protein kinase (DAPK), glutathione S-transferase P1 (GSTP1), IGF-II (IGF2), IGF2R, EF1a, TFIIAα/β-like factor (ALF), DiGeorge syndrome critical region gene 8 (DGCR8); hypothetical protein FILJ 11753; Zinc finger protein 358 (ZNF358); Solute carrier family 12 (SLC12A7) (potassium/chloride transporters); Phosphodiesterase 4A, cAMP-specific (PDE4A) (phosphodiesterase E2 dunce homolog, *Drosophila*); Hermansky-Pudlak syndrome-6 (HPS6); Hypothetical protein FLJ22595; homeobox protein A9 isoform a (HOXA9); hypothetical protein MGC14376; homeobox B7 (HOXB7); dynamin 1 (DNM1); hypothetical protein FLJ21827; hypothetical protein FLJ10496; transcriptional activator of the c-fos promoter (CROC4); hypothetical protein FLJ20436; sprouty homolog 4 (SPR4); ring finger protein 1 (RING1); CD37 antigen; gene DKFZP564J0123: nuclear protein E3-3 isoform a; and peripheral benzodiazepine receptor-associated protein 1 (BZRAP1).

Some examples of enhancers include, but are not limited to, genomic DNA sequences within 10-kb upstream or downstream from, or within the open reading frame of the following genes: E-cadherin (CDH1), H-cadherin (CDH13), caspase-8, retinoic acid receptor beta-2 (RARβ), tissue inhibitor of metalloproteinase 3 (TIMP-3), $O^6$-methylguanine-DNA-methyltransferase (MGMT), p14$^{ARF}$, death-associated protein kinase (DAPK), glutathione S-transferase P1 (GSTP 1), IGF-II (IGF2), IGF2R, EF1a, TFIIAα/β-like factor (ALF), DiGeorge syndrome critical region gene 8 (DGCR8); hypothetical protein FLJ11753; Zinc finger protein 358 (ZNF358); Solute carrier family 12 (SLC12A7) (potassium/chloride transporters); Phosphodiesterase 4A, cAMP-specific (PDE4A) (phosphodiesterase E2 dunce homolog, *Drosophila*); Hermansky-Pudlak syndrome-6 (HPS6); Hypothetical protein FLJ22595; homeobox protein A9 isoform a (HOXA9); hypothetical protein MGC14376; homeobox B7 (HOXB7); dynamin 1 (DNM1); hypothetical protein FLJ21827; hypothetical protein FLJ10496; transcriptional activator of the c-fos promoter (CROC4); hypothetical protein FLJ20436; sprouty homolog 4 (SPRY4); ring finger protein 1 (RING1); CD37 antigen; gene DKFZP564J0123: nuclear protein E3-3 isoform a; and peripheral benzodiazepine receptor-associated protein 1 (BZRAP1).

As used herein, the term "transcribed by" means produced a nucleotide polymerization reaction catalyzed by an RNA polymerase. For example, a pri-miRNA or other small non-coding RNA may be transcribed by a genomic DNA sequence in the centromeric region by the action of an RNA polymerase.

As used herein, the phrase "imprinted" means allele-specific gene expression capacity. Imprinting is often based on the parental origin of the alleles. For example, altered paternal expression of genes within the chromosome 15q11-13 region gives rise to Prader-Willi syndrome, a condition causing neonatal hypotonia with subsequent hyperphagia and obesity. Altered maternal expression of the UBE3A (ubiquitin protein ligase E3A) gene, which lies in the same region, causes Angelman's syndrome, a neurodevelopmental disorder associated with characteristic movements and a sociable disposition.

The terms "locus" or "loci" as used herein, refer to a region or regions, respectively, of genomic DNA with definable attributes, such as being associated with a particular phenotype by genetic mapping techniques. For example, human alpha satellite DNAs are considered to be centromeric loci. The term "imprinted locus" is used to indicate a region of genomic DNA which has expression characteristics that differ from the corresponding homologus allele based on the parental origin of each allele. For example, imprinted loci sometimes differ in gene expression due to differences in DNA methylation or histone acetylation states in their promoter and/or enhancer regions.

As used herein, the phrase "locus marked by dosage-compensation" means that the two alleles at a genetic locus have specific markings that direct differential gene expression. For example, dosage-compensation in mammals is achieved by a mechanism that leads to transcriptional silencing of almost all genes present on one of the two X chromosomes in female cells, a process known as X-chromosome inactivation (XCI). Dosage-compensation is a counting process which ensures that only a single X chromosome remains active per diploid cell. Inactivation is initiated from an X-linked locus, the X-inactivation center (Xic), and inactivity spreads along the chromosome toward both ends. XCI is established by complex mechanisms, including DNA methylation, heterochromatinization, and late replication. Once established, inactivity is stably maintained in subsequent cell generations. The function of an X-inked regulatory gene, Xist, is critically involved in XCI. The Xist gene maps to the Xic locus, it is transcribed only from the inactive X chromosome, and the Xist RNA associates with the inactive X chromosome in the nucleus. Xist has been shown to be required in cis for XCI. Expression of the Xist gene has been proposed to be controlled by the antisense Tsix transcript.

The present invention provides oligomeric compounds targeting or mimicking small non-coding RNAs that are produced in cis or in trans to the sites they epigenetically regulate. As used herein, the phrase "produced in cis to the site it regulates" describes a small non-coding RNA that is produced by the promoter, enhancer, or insulator region that it regulates. For example, small non-coding RNAs can be transcribed from sequences in the same region of DNA that they regulate. Centromeric DNA regions may transcribe small non-coding RNAs that also have a role in regulating heterochromatin formation, function or maintenance of the centromere (cis-regulation).

As used herein, the phrase "produced in trans to the site it regulates" describes a small non-coding RNA that is produced by a site located away from the promoter, enhancer or insulator it regulates. For example, a small non-coding RNA that regulates a gene promoter or enhancer may be transcribed from sequences at a distance from (more than 10 kb from) the heterochromatic site in the DNA that they regulate (trans-regulation).

Examples of gene regulatory regions which can be regulated by small non-coding RNAs are promoters (TATA box regions), insulators and enhancers (which can act on promoters over many tens of kilobases of DNA and can be located 5' or 3' to the promoter they regulate, as well as being located within the open reading frame). As used herein, the term "promoter" refers to a genomic DNA site to which RNA polymerase will bind and initiate transcription. For example, while not wishing to be bound by theory, a promoter is usually upstream from the gene coding region upon which it acts to control expression; the promoter serves as a recognition signal for an RNA polymerase and marks the site of initiation of transcription.

As used herein, the term "enhancer" refers to a cis-acting genomic DNA element capable of regulating expression of a gene. For example, while not wishing to be bound by theory, an enhancer can facilitate transcription factor binding at gene promoters. The binding of a complex of transcription factors at an enhancer can affect the availability of the gene's promoter to RNA polymerase. A gene may have multiple enhancers. An enhancer may be a genomic DNA sequence, cognate to a small non-coding RNA or oligomeric compound, which plays a role in epigenetic control of gene expression. An enhancer can be located as far as many tens of kilobases upstream or downstream from the promoter of a gene, or can be located within a 5'-UTR, a 3'-UTR, an intron, or an exon of an open reading frame of a gene.

Other gene regulatory sequences can include one or more enhancers, silencers, and insulators, initiator sequences (INR), and downstream promoter elements (DPE). For example, a pre-mRNA transcript may contain introns or exons which may produce one or more small non-coding RNAs that play a role in the regulation of transcription of the pre-mRNA by interacting with their own promoters or enhancers in cis.

The oligomeric compounds targeting or mimicking small non-coding RNAs may regulate the expression of a gene encoding a heterochromatin protein, an exosome/PM-Scl component histone modifying enzyme, or pseudouridylating enzyme, or may guide the activity of the expressed gene product. As used herein the phrase "exosome/PM-Scl component" means an RNA or protein that comprises the nucleolar ribonucleoprotein complex with RNA exonucleolytic activity known as the exosome in yeasts and the PM-Scl complex in mammals. Examples of protein components include, but are not limited to, polymyositis/scleroderma (PM-Scl) autoantigen, 75-k) (PMSCL1), PM-Scl autoantigen, 100-kD (PMSCL2), CSL4, RRP40, RRP41, RRP42/KIAA0116, RRP46, RRP4, mRNA transport regulator 3 (MTR3), OIP2/RRP43, M-phase phosphoprotein 6 (MPP6) and SKIV2L. Another example of an exosome/PM-Scl component is the SUPT6H protein, which co-purifies with the exosome complex proper. Examples of RNA components of the exosome/PM-Scl complex include, but are not limited to, AU-rich element (ARE)-containing mRNAs, snRNAs, snoRNAs and possibly microRNAs or as-yet-unidentified guide RNAS.

As used herein, the phrase "guides the activity" means to direct the binding, hybridization, or catalytic activity of an RNA or a protein For example, a small non-coding RNA may hybridize to a specific target RNA and subsequently be bound by a dsRNA-binding protein, which may then interact with a ribonucleoprotein complex; thus, the small non-coding RNA guides and specifies which cis sequence gets modified by methylation or pseudouridylation, for example. For example, a snoRNA is believed to act as a guide RNA in directing the pseudouridylating activity of the Cbf5/DSK protein within its ribonucleoprotein complex to its target nucleic acids, ribosomal RNAs, thereby directing the modification of specific targets. Similar mechanisms may employ small non-coding RNAs to guide the methylation of genomic DNA, such as within gene promoters, enhancers, insulators, centromeres, telomeres, origins of DNA replication, imprinted loci, to influence heterochromatin formation or function, or within gene promoters or enhancers to cause repression or silencing of gene transcription.

While not wishing to be bound by theory, small nucleolar RNAs can be generally grouped into H/ACA or C/D box snoRNA subclasses. In a further embodiment of this invention, oligomeric compounds can be designed to target snoRNAs resulting in modulation of their function. These compounds can be targeted to the entire snoRNA or to substructures or domains within the snoRNA. Domains to be targeted include, but are not limited to, the box H, box ACA, box C, box C', box D, box D' motifs, as well as to U-turns, K-turns, and loop structures of the snoRNAs. Sites toward the 5' end of the box D and box D' motifs of C/D box snoRNAs can also be selected as mimics or as targets for compounds capable of blocking the association of a snoRNA with other biomolecules which will effectively modulate snoRNA function.

The oligomeric compounds targeting or mimicking the small non-coding RNAs may regulate the formation, localization, or function of an exosome/PM-Scl complex. As used herein, the terms "localization" or "compartmentalization" mean that proteins, nucleic acids, or ribonucleoprotein complexes are sequestered within a cell, putting them in contact with other substrates or enzymes involved in a catalytic process, for example, or removing them from contact with active areas, substrates or enzymes.

The oligomeric compounds targeting or mimicking the small non-coding RNAs may mark one or more heterochromatic regions or heterochromatin proteins for modifications. Examples of modifications are transcriptional modifications of nucleic acids, including but not limited to modifications on genomic DNA, as well as post-transcriptional modifications of nucleic acids, or post-translational modifications of proteins. As used herein, the phrase "marks one or more heterochromatic regions for modification" means that a small non-coding RNA hybridizes to a nucleic acid target and thereby forms a double- or multiple-stranded nucleic acid structure serving as a signal for a modification event that triggers the formation of heterochromatin. An example of an art-recognized small non-coding RNA marking a region for imprinting is the non-coding Air RNA which is paternally expressed in cis and is required for the silencing of the Igf2r, Slc22a2 and Slc22a3 genes.

Modifications can occur on genomic DNA, RNA or proteins (for example, histone proteins) and can include acetylation, deacetylation, phosphorylation, dephosphorylation, methylation, demethylation, ubiquitination, or pseudouridylation. These modifications may regulate the formation, localization or function of an exosome/PM-Scl complex, a kinetochore or telomerase complex, or a histone modifying complex. As used herein, the term "transcriptional modification" means a modification of a nucleic acid occurring at a time prior to or at the time it is transcribed. Examples of transcriptional modification include but are not limited to methylation and demethylation of genomic DNA sequences. As used herein, the term "post-transcriptional modification" means the modification of nucleic acids, such as mRNAs, rRNAs, tRNAs, snRNAs, snoRNAs and microRNAs. Examples of post-transcriptional modifications are the 5'-methyl-G capping of mRNAs or the pseudouridylation of snRNAs, snoRNAs or rRNAs, as well as the post-transcriptional gene silencing processes such as RNAi. As used herein, the term "post-translational modification" means the modification of a protein after is has been translated. Examples of protein modifications are acetylation, deacetylation, methylation, demethylation, ubiquitination, sumoylation, phosphorylation or dephosphorylation of histone proteins. For example, a common way to control gene expression is by controlling the post-translational phosphorylation of transcription factors. Such post-translational modifications might activate or inhibit the transcription factor in turning on gene expression. Posttranslational modification by small ubiquitin-like modifier (SUMO) conjugation is reported to regulate the subnuclear localization of several proteins. Any of these modifications might be necessary for direct binding interactions between the nucleic acid or protein being modified and other nucleic acids or proteins, or they might be necessary for the assembly of a ribonucleoprotein complex. Furthermore, any of these transcriptional, post-transcriptional or post-translational modifications may lead to a change in the subcellular localization of a ribonucleoprotein complex, or might change the regulation of gene transcription.

A body of evidence shows the interplay between different modifications on single or multiple histone tails. Phosphorylation of histone H3 at serine 10 can enhance acetylation on lysine 14 and affect transcription at specific genes. Histone H4 arginine 3 (H4 R3) methylation mediated by PRMT1 facilitates p300-mediated acetylation on H4-K8 and H4-K12, and conversely, histone H4 acetylation on any of four lysines (K5, K8, K12, or K16) also inhibits the subsequent methylation at H4-R3 by PRMT1 (Ren, et al., Mol. Cell. Biol., 2003, 23, 2778-89; and Thang, et al., Genes Dev., 2001, 15, 2343-60). Methylation of certain amino acid residues in histones H3 and H4 has been correlated with certain functions. Methylation of histone H3 K9 and H3 K27, as well as histone H4 K20 is generally associated with imprinting and transcriptional silencing. Methylation of histone H3 K4, H3 K36 and H3 K79 is generally associated with transcriptional stimulation. Methylation of arginine residues within histone H3 has been linked to active transcription. Furthermore, a process of deimination that converts arginine to citrulline, mediated by peptidyl arginine deiminase 4 (PADI4) was recently reported to antagonize histone arginine methylation (Cuthbert, et al., Cell, 2004, 118, 545-53).

DNA methyltransferase 1 (DNMT1) is one non-limiting example of an enzyme that catalyzes DNA methylation. DNMT1 plays an essential role in murine development and is thought to be the enzyme primarily responsible for maintenance of the global methylation status of genomic DNA. Loss of DNMT1 in human cancer cells affects the methylation status of some pericentromeric sequences, leading to a profound disorganization of nuclear architecture and an altered pattern of histone H3 modification that results in an increase in the acetylation and a decrease in the dimethylation and trimethylation of lysine 9. Additionally, this phenotype is associated with a loss of interaction of histone deacetylases (HDACs) and HP1 (heterochromatin protein 1) with histone H3 and pericentromeric repetitive sequences (satellite 2). DNMT1 activity, via maintenance of the appropriate histone H3 modifications, contributes to the preservation of the correct organization of large heterochromatic regions (Espada et al., J. Biol. Chem., 2004, 279, 37175-84). Thus, DNA methylation status can have effects on histone methylation patterns, as well.

In some cases, the methylation status of DNA and the acetylation status of histone proteins appear to be inversely related, and may be coordinately regulated. Whereas DNA methylation often leads to histone deacetylation, histone acetylation also appears to prevent methylation; acetylation has been reported to be responsible for the maintenance of a region of unmethylated DNA over promoter regions (Mutskov, et al., Genes Dev., 2002, 16, 1540-54). Furthermore, it was recently demonstrated that aberrantly silenced genes in cancer cells exhibit a heterochromatic structure characterized by histone H3 K9 hypermethylation and histone H3 K4 hypomethylation, and that this aberrant heterochromatin state was incompatible with transcriptional initiation but does not inhibit elongation by RNA polymerase II. Treatment with 5-aza-2'-deoxycytidine (5-aza-dC), known to inhibit cytosine methylation, was found to induce a rapid and substantial remodeling of the heterochromatic domains of the p14ARF/p16INK4a locus in T24 bladder cancer cells, as well as a loss of methyl-CpG binding protein (MeCP2) binding, reduced levels of dimethylated H3 K9 and increased levels of dimethylated H3 K4 at this locus. Treatment with 5-Aza-dC also increased acetylation and H3-K4 methylation at the unmethylated p14 promoter, suggesting it can induce chromatin remodeling independently of its effects on cytosine methylation. Thus, H3 K9 methylation may play a role in the silencing of tumor-suppressor genes in cancer (Nguyen, et al., Cancer Res., 2002, 62, 6456-61)

The DNA methyltransferases DNMT3a and DNMT3b are effective in methylation of both hemi and unmethlyated DNA, required for de novo DNA methylation. Recently, a novel set of RNA-binding proteins, well known for their function in chromatin regulation, was identified and found to be components of the mammalian DNA methylation system. A subset of the DNA methyltransferases (including DNMT3a and DNMT3b) as well as Methyl DNA Binding Domain proteins were demonstrated to form RNA-protein complexes. The high affinity RNA-binding activity of a Methyl DNA Binding Domain protein was characterized and shown to be distinct from the methyl DNA binding domain. In fact, the RNA and methyl-CG binding properties of the Methyl DNA Binding Domain proteins were reported to be mutually exclusive; in gel mobility shift assays, RNAs were found to bind to DNMT3a and DNMT3b and to prevent association with DNA substrates. It was hypothesized that DNA methyltransferases and Methyl DNA Binding Domain proteins may allow RNA molecules to participate in DNA methylation-mediated chromatin control (Jeffery and Nakielny, J. Biol. Chem., 2004, 279, 49479-49487).

As used herein, the phrase "histone modifying enzyme" and "histone modifying complex" means the complex of proteins which catalyze the acetylation, deacetylation, methylation or demethylation of histone proteins. Examples of histone modifying enzymes include, but are not limited to the SET-domain-containing proteins of the evolutionary conserved SU(VAR)3-9 family of histone methyltransferases, the histone acetyltransferases CBP and PCAF, and histone deacetylases (HDACs). For example, lysine (Lys) 79 of histone H3 is methylated in eukaryotic organisms. In the yeast *Saccharomyces cerevisiae*, Lys 79 of histone H3 is methylated by Dot1, a protein shown previously to play a role in telomeric silencing (Ng et al., Genes Dev., 2002, 16, 1518-27). Some HDACs, which are believed to favor chromatin condensation and play a critical role in transcriptional repression, exhibit the unique property of being regulated by nucleocytoplasmic shuttling and have been shown to be sumoylated. Moreover, the modification of HDAC4 depends on the presence of an intact nuclear localization signal and is catalysed by the nuclear pore complex (NPC) RanBP2 protein, recently identified to function as a SUMO E3 ligase. These findings suggest that sumoylation of HDAC4 takes place at the NPC and is coupled to its nuclear import (Kirsh et al., EMBO J., 2002, 21, 2682-91).

In some embodiments, inhibitors of methylation, acetylation, phosphorylation, sumoylation, ubiquitination, or pseudouridylation may be employed. Inhibitors of methylation are known in the art, and may include, but are not limited to, inhibitors of DNA methyltransferase enzymes, such as 5-azacytidine, 5-aza-dC, procainamide, and methylgene MG98. Inhibitors of histone deacetylase activity are known in the art, and may include, but are not limited to, suberoylanilide hydroxamic acid (SAHA), Trichostatin A (TSA), trapoxin (TPX), MS-27-275, sodium butyrate, phenylbutyrate, valproic acid, apicidin, oxamflatin, depsipeptide, and FR901228.

As used herein, the phrase "ribonucleoprotein complex" means a multimeric complex that includes nucleic acid and protein components. Examples of ribonucleoprotein complexes include, but are not limited to the RNA-induced silencing complex (RISC), RNA-induced Initiation of Transcriptional gene Silencing (RITS) complex, the X-inactivation center (XIC), telomeres, centromere/kinetochores, origin recognition complexes and exosome/PM-Scl complexes. As used herein, the phrase "origin-recognition complex" or "ORC" means the multimeric complex that assembles on origins of DNA replication.

In some embodiments, the oligomeric compounds of the invention may be in the form of single-stranded, double-stranded, circular or hairpin oligomeric compounds and may contain structural elements such as internal or terminal bulges or loops. Furthermore, the oligomeric compounds of the invention can have one or more moieties bound or conjugated, which facilitates the active or passive transport, localization, or compartmentalization of the oligomeric compound. Cellular localization includes, but is not limited to, localization to within the nucleus, the nucleolus, or the cytoplasm. Compartmentalization includes, but is not limited to, any directed movement of the oligonucleotides of the invention to a cellular compartment including the nucleus, nucleolus, mitochondrion, or embedding into a cellular membrane. Once introduced to a system, the oligomeric compounds of the invention may elicit the action of one or more enzymes or proteins to effect modulation of the levels, expression or function of the target nucleic acid.

One non-limiting example of a protein whose activity may be elicited is the Drosha RNase III enzyme. Drosha is a nuclear enzyme that processes long primary RNA transcripts (pri-miRNAs) from approximately 70 to 450 nucleotides in length into pre-miRNAs (from about 50 to about 80 nucleotides in length) which are exported from the nucleus to encounter the human Dicer enzyme which then processes pre-miRNAs into miRNAs. It is believed that, in processing the pri-miRNA into the pre-miRNA, the Drosha enzyme cuts the pri-miRNA at the base of the mature miRNA, leaving a 2-nt 3' overhang (Lee, et al., Nature, 2003, 425, 415-419). The 3' two-nucleotide overhang structure, a signature of RNaseIII enzymatic cleavage, has been identified as a critical specificity determinant in targeting and maintaining small RNAs in the RNA interference pathway (Murchison et al., Curr. Opin. Cell Biol., 2004, 16, 223-9).

The Drosha enzyme was recently reported to be a component of two multiprotein complexes; the larger complex contains multiple classes of RNA-associated proteins including helicases, dsRNA-binding proteins, heterogenous nuclear ribonuclearproteins, and the Ewing's sarcoma family of proteins, and the smaller complex (dubbed "Microprocessor") is composed of Drosha and the dsRNA-binding protein DiGeorge syndrome critical region gene 8 (DGCR8). Both components of Microprocessor were reported to be necessary and sufficient in mediating the genesis of miRNAs from the primary miRNA transcript (Gregory, et al., Nature, 2004, 432, 235-40).

A further non-limiting example involves the enzymes of the RISC complex. Use of the RISC complex to effect cleavage of RNA targets thereby greatly enhances the efficiency of oligonucleotide-mediated inhibition of gene expression.

The present invention provides, inter alia, oligomeric compounds and compositions containing the same wherein the oligomeric compound includes one or more modifications that render the compound capable of supporting modulation of the expression or function of the small non-coding RNA or its precursor by a degradation or cleavage mechanism.

Pharmaceutical and other compositions, as well as kits or assay devices comprising the compounds and compositions of the invention are also provided. The present invention also provides use of the compounds and compositions disclosed herein in the manufacture of medicaments for carrying out any of the methods and treatments described herein.

As used herein, the phrase "chromosome segregation" means the partitioning of homologous sister chromatids into daughter cells during cell divisions such as mitosis or meiosis. As used herein, "arresting or delaying mitosis or meiosis" means activating a cell cycle checkpoint such that the sequence of events that normally occurs in the process of mitosis or meiosis is paused or halted. As used herein, "inhibiting spermatogenesis" means inhibiting meiotic divisions in gametogenic cells. As used herein, "contraception" means preventing the ability of gametes to join and complete the process of fertilization. One form of contraception may be achieved by preventing gametogenesis in an organism.

In one embodiment, the oligomeric compounds of the invention are designed to exert their modulatory effects via mimicking or targeting small non-coding RNAs associated with cellular factors such as transporters or chaperones. These cellular factors can be protein, lipid or carbohydrate based and can have structural or enzymatic functions that may or may not require the complexation of one or more metal ions.

In some embodiments of the invention, the oligomeric compounds are designed to exert their modulatory effects via mimicking or targeting small non-coding RNAs associated with cellular factors that affect gene expression, more specifically those involved in RNA or DNA modifications.

These modifications include, but are not limited to, post-transcriptional or chromosomal modifications such as methylation, acetylation, pseudouridylation, sumoylation, amination or imination.

Furthermore, the oligomeric compounds of the invention comprise one or more conjugate moieties which facilitate posttranscriptional modification.

Oligomeric compounds or compositions of the invention are used to induce potent and specific modulation of gene function through interactions with or mimicry of small non-coding RNAs that are processed by the RISC complex. These compounds include single-stranded oligomeric compounds that bind in a RISC complex, double-stranded antisense/sense pairs of oligomeric compounds, or single-stranded oligomeric compounds that include both an antisense portion and a sense portion.

General Oligomer Synthesis:

Oligomeric compounds and phosphoramidites are made by methods well known to those skilled in the art. Oligomerization of modified and unmodified nucleosides is performed according to procedures known in the art for synthesis of DNA-like compounds (Protocols for Oligonucleotides and Analogs, Ed. Agrawal, 1993, Humana Press) and/or RNA-like compounds (Scaringe, Methods, 2001, 23, 206-217; Gait et al., Applications of Chemically synthesized RNA in RNA:Protein Interactions, Ed. Smith, 1998, 1-36; Gallo et al., Tetrahedron, 2001, 57, 5707-5713).

RNA oligomers can be synthesized by methods disclosed herein or purchased from various RNA synthesis companies such as for example Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

RNA Synthesis:

Methods of RNA synthesis are well known in the art (Scaringe, Ph.D. Thesis, University of Colorado, 1996; Scaringe et al., J. Am. Chem. Soc., 1998, 120, 11820-11821; Matteucci et al., J. Am. Chem. Soc., 1981, 103, 3185-3191; Beaucage et al., Tetrahedron Lett., 1981, 22, 1859-1862; Dahl et al., Acta Chem. Scand., 1990, 44, 639-641; Reddy et al., Tetrahedrom Lett., 1994, 25, 43114314; Wincott et al., Nucleic Acids Res., 1995, 23, 2677-2684; Griffin et al., Tetrahedron, 1967, 23, 2301-2313; Griffin et al., Tetrahedron, 1967, 23, 2315-2331).

Oligonucleotide Isolation:

Methods of isolation, synthesis and analysis of oligonucleotides are well known in the art. A 96-well plate format is particularly useful for the synthesis, isolation and analysis of oligonucleotides.

Oligonucleotide Modifications

Specific examples of oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain oligomeric compounds of the invention can also have one or more modified internucleoside linkages. A suitable phosphorus-containing modified internucleoside linkage is the phosphorothioate internucleoside linkage.

Modified oligonucleotide backbones (internucleoside linkages) containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In other embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Modified oligonucleotide backbones (internucleoside linkages) that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleotides include, but are not limited to, U.S. Pat. Nos. 5,034,506; 5,166,315; 5,185,444; 5,214,134;

5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Another group of oligomeric compounds amenable to the present invention includes oligonucleotide mimetics. The term mimetic as it is applied to oligonucleotides is intended to include oligonucleotides within oligomeric compounds wherein only the furanose ring or both the furanose ring and the internucleotide linkage are replaced with novel groups, replacement of only the furanose ring is also referred to in the art as being a sugar surrogate. In these nucleotide mimetics, the heterocyclic base moiety or a modified heterocyclic base moiety is maintained for hybridization with an appropriate target nucleic acid. One example of an oligomeric compound comprising an oligonucleotide mimetic, which has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA oligomeric compounds include, but are not limited to, U.S. Pat. Nos. 5,539,082; 5,714,331; and 5,719,262, each of which is herein incorporated by reference. Teaching of PNA oligomeric compounds can be found in Nielsen et al., Science, 1991, 254, 1497-1500.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A suitable class of linking groups have been selected to give a non-ionic oligomeric compound. The non-ionic morpholino-based oligomeric compounds are less likely to have undesired interactions with cellular proteins. Morpholino-based oligomeric compounds are non-ionic imitations of oligonucleotides which are less likely to form undesired interactions with cellular proteins (Braasch et al., Biochemistry, 2002, 41, 4503-4510). Morpholino-based oligomeric compounds are disclosed in U.S. Pat. No. 5,034,506. The morpholino class of oligomeric compounds have been prepared having a variety of different linking groups joining the monomeric subunits.

Another class of oligonucleotide mimetic is referred to as cyclohexenyl nucleic acids (CeNA). The furanose ring normally present in an DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore, the incorporation of CeNA into a sequence targeting RNA was stable to serum and able to activate E. coli RNase resulting in cleavage of the target RNA strand.

Another class of oligonucleotide mimetic (anhydrohexitol nucleic acid) can be prepared from one or more anhydrohexitol nucleosides (see, Wouters and Herdewijn, Bioorg. Med. Chem. Lett., 1999, 9, 1563-1566).

Another group of modifications includes nucleosides having sugar moieties that are bicyclic thereby locking the sugar conformational geometry. The most studied of these nucleosides is a bicyclic sugar moiety having a 4'-$CH_2$—O-2' bridge, in which the 2'-O— has been linked via a methylene group to the 4' carbon. This bridge attaches under the sugar as shown forcing the sugar ring into a locked 3'-endo conformation geometry. The α-L nucleoside has also been reported wherein the linkage is above the ring and the heterocyclic base is in the a rather than the β-conformation (see U.S. Patent Application Publication No.: Application 2003/0087230). The xylo analog has also been prepared (see U.S. Patent Application Publication No.: 2003/0082807). The preferred bridge for a locked nucleic acid (LNA) is 4'-(—$CH_2$—)$_n$—O-2' wherein n is 1 or 2. The literature is confusing when the term locked nucleic acid is used but in general locked nucleic acids refers to n=1, ENA™ refers to n=2 (Kaneko et al., U.S. Patent Application Publication No.: US 2002/0147332, Singh et al., Chem. Commun., 1998, 4, 455-456, also see U.S. Pat. Nos. 6,268,490 and 6,670,461 and U.S. Patent Application Publication No.: US 2003/0207841). However the term locked nucleic acids can also be used in a more general sense to describe any bicyclic sugar moiety that has a locked conformation.

ENA™ (n=2) along with LNA (n=1) have been studied more than the myriad of other analogs. Oligomeric compounds incorporating LNA and ENA analogs display very high duplex thermal stabilities with complementary DNA and RNA ($T_m$=+3 to +10 C), stability towards 3'-exonucleolytic degradation and good solubility properties.

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000,13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points ($T_m$=+15/+11) toward DNA complements.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Some oligonucleotide mimetics have been prepared to include bicyclic and tricyclic nucleoside analogs (Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting oligomeric compounds containing tricyclic nucleoside analogs have shown increased thermal stabilities ($T_m$s) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

Another oligonucleotide mimetic has been reported wherein the furanosyl ring has been replaced by a cyclobutyl moiety.

Modified Sugars

Modifications can also be substitutions, and oligomeric compounds of the invention may contain one or more substituted sugar moieties. These oligomeric compounds comprise a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Some oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. One modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—$N(CH_3)_2$.

Other sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. One 2'-arabino modification is 2'-ara-F.

Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative substituents groups are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Representative guanidino substituent groups are disclosed in U.S. patent application Ser. No. 09/349,040, entitled "Functionalized Oligomers," filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", hereby incorporated by reference in its entirety.

Chimeric Oligonucleotides:

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers." Methods of synthesizing chimeric oligonucleotides are well known in the art.

The stability of the duplex formed between a target RNA and a synthetic sequence is central to therapies such as, but not limited to, antisense mechanisms, including RNase H-mediated and RNA interference mechanisms, as these mechanisms involved the hybridization of a synthetic sequence strand to an RNA target strand. In the case of RNase H, effective inhibition of the mRNA requires that the antisense sequence achieve at least a threshold of hybridization. The terms used to describe the conformational geometry of homoduplex nucleic acids are "A Form" for RNA and "B Form" for DNA. In general, RNA:RNA duplexes are more stable and have higher melting temperatures ($T_m$s) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

One routinely used method of modifying the sugar puckering is the substitution of the sugar at the 2'-position with a substituent group that influences the sugar geometry. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is also correlated to the stabilization of the stacked conformation.

Steric bulk at the 2'-position of the sugar moiety is also better accommodated in an A-form duplex than a B-form duplex.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron, 2001, 57, 5707-5713. Harry-O'kuru et al., J. Org. Chem., 1997, 62, 1754-1759 and Tang et al., J. Org. Chem., 1999, 64, 747-754.) Alternatively, preference for the 3'-endo conformation can be achieved by deletion of the 2'-OH as exemplified by 2'deoxy-2'F-nucleosides (Kawasaki et al., J. Med. Chem., 1993, 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters, 1995, 5, 1455-1460 and Owen et al., J. Org. Chem., 1976, 41, 3010-3017), or for example modification to yield methanocarba nucleoside analogs (Jacobson et al., J. Med. Chem. Lett., 2000, 43, 2196-2203 and Lee et al., Bioorganic and Medicinal Chemistry Letters, 2001, 11, 1333-1337) also induce preference for the 3'-endo conformation.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used as RNA-like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds designed to act as triggers of RNAi having one or more nucleosides modified in such a way as to favor a C3'-endo type conformation.

Along similar lines, oligomeric triggers of RNAI response might be composed of one or more nucleosides modified in such a way that conformation is locked into a C3'-endo type conformation, i.e. Locked Nucleic Acid (LNA) (Singh et al, Chem. Commun., 1998, 4, 455-456), and ethylene bridged Nucleic Acids (ENA) (Morita et al, Bioorganic & Medicinal Chemistry Letters, 2002, 12, 73-76).

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2 aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

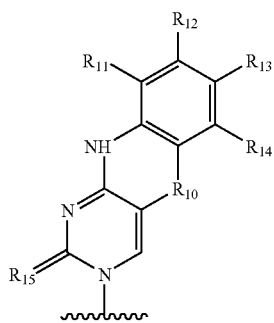

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov et al., Nucleosides and Nucleotides, 1997, 16, 1837-1846), 1,3-diazaphenothiazine-2-one ($R_{10}$=S, $R_{11}$—$R_{14}$=H), (Lin, K.-Y.; Jones, R. J.; Matteucci, M. J. Am Chem. Soc. 1995, 117, 3873-3874) and 6,7,8,9-tetrafluoro-1,3-diazaphenoxazine-2-one ($R_{10}$=O, $R_{11}$-$R_{14}$=F) (Wang et al., Tetrahedron Lett., 1998, 39, 8385-8388). When incorporated into oligonucleotides, these base modifications were shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Helix-stabilizing properties have been observed when a cytosine analog/substitute has an aminoethoxy moiety attached to the rigid 1,3-diazaphenoxazine-2-one scaffold ($R_{10}$=O, $R_{11}$=—O—CH$_2$)$_2$—NH$_2$, $R_{12\text{-}14}$=H) (Lin et al., J. Am. Chem. Soc., 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$) which is the highest known affinity enhancement for a single modification. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Tricyclic heterocyclic compounds and methods of using them that are amenable to the present invention are disclosed in U.S. Pat. No. 6,028,183, and U.S. Pat. No. 6,007,992, the contents of both are incorporated herein in their entirety.

The enhanced binding affinity of the phenoxazine derivatives together with their sequence specificity makes them valuable nucleobase analogs for the development of more potent antisense-based drugs.

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

One substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, carbohydrates, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. patents that teach the preparation of such oligonucleotide conjugates include, but are not limited to, U.S. Pat. Nos. 4,828,979; 4,948,882; 5,218,105; 5,525, 465; 5,541,313; 5,545,730; 5,552,538; 5,578,717; 5,580, 731; 5,580,731; 5,591,584; 5,109,124; 5,118,802; 5,138, 045; 5,414,077; 5,486,603; 5,512,439; 5,578,718; 5,608, 046; 4,587,044; 4,605,735; 4,667,025; 4,762,779; 4,789, 737; 4,824,941; 4,835,263; 4,876,335; 4,904,582; 4,958, 013; 5,082,830; 5,112,963; 5,214,136; 5,082,830; 5,112, 963; 5,214,136; 5,245,022; 5,254,469; 5,258,506; 5,262, 536; 5,272,250; 5,292,873; 5,317,098; 5,371,241; 5,391, 723; 5,416,203; 5,451,463; 5,510,475; 5,512,667; 5,514, 785; 5,565,552; 5,567,810; 5,574,142; 5,585,481; 5,587, 371; 5,595,726; 5,597,696; 5,599,923; 5,599,928 and 5,688, 941, each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. For double-stranded oligomeric compounds, the cap may be present at either or both termini of either strand. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (see Wincott et al., International PCT publication No. WO 97/26270, incorporated by reference herein).

Suitable 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49,1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, an oligomeric compound may be designed to comprise a region that serves as a substrate for RNase H. RNase H is a cellular endonuclease which cleaves the RNA strand of an RNA:DNA duplex. Activation of RNase H by an oligomeric compound having a cleavage region, therefore, results in cleavage of the RNA target, thereby enhancing the efficiency of the oligomeric compound. Consequently, comparable results can often be obtained with shorter oligomeric compounds having substrate regions when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide mimics, oligonucleotide analogs, oligonucleosides and/or oligonucleotide mimetics as described above. Such oligomeric compounds have also been referred to in the art as hybrids, hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In one aspect, the present invention is directed to oligomeric compounds that are designed to have enhanced properties compared to native RNA. One method to design optimized or enhanced oligomeric compounds involves each nucleoside of the selected sequence being scrutinized for possible enhancing modifications. One modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention may include at least one 5'-modified phosphate group on a single strand or on at least one 5'-position of a double-stranded sequence or sequences. Other modifications considered are internucleoside linkages, conjugate groups, substitute sugars or bases, substitution of one or more nucleosides with nucleoside mimetics and any other modification that can enhance the desired property of the oligomeric compound.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one, or about 1 to about 3 hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12, from 1 to about 6, and the total number of ring members varies from three to about 15, or from about 3 to about 8. Suitable ring heteroatoms are N, O and S. Suitable heterocycloalkyl groups include, but are not limited to, morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Suitable aryl rings have about 6 to about 20 ring carbons. Especially suitable aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. The ring system can contain about 1 to about 4 rings. The number of carbon atoms can vary from 1 to about 12, from 1 to about 6, and the total number of ring members varies from three to about 15, or from about 3 to about 8. Suitable ring heteroatoms are N, O and S. Suitable hetaryl moieties include, but are not limited to, pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the submoieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Suitable halo (halogen) substituents are Cl, Br, F and I.

The aforementioned optional substituents are, unless otherwise herein defined, suitable substituents depending upon desired properties. Included are halogens (Cl, Br, F, I), alkyl, alkenyl, and alkynyl moieties, NO$_2$, NH$_3$ (substituted and unsubstituted), acid moieties (e.g. —CO$_2$H, —OSO$_3$H$_2$, etc.), heterocycloalkyl moieties, hetaryl moieties, aryl moieties, etc. In all the preceding formulae, the squiggle (~) indicates a bond to an oxygen or sulfur of the 5'-phosphate.

Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Screening methods for the identification of effective modulators of small non-coding RNAs are also comprehended by the instant invention and comprise the steps of contacting a small non-coding RNA, or portion thereof, with one or more candidate modulators, and selecting for one or more candidate modulators which decrease or increase the levels, expression or alter the function of the small non-coding RNA. Once it is shown that the candidate modulator or modulators are capable of modulating (e.g. either decreasing or increasing) the levels, expression or altering the function of the small non-coding RNA, the modulator may then be employed in further investigative studies, or for use as a target validation, research, diagnostic, or therapeutic agent in accordance with the present invention.

Screening methods for the identification of small non-coding RNA mimics are also within the scope of the invention. Screening for small non-coding RNA modulators or mimics can also be performed in vitro, ex vivo, or in vivo by contacting samples, tissues, cells or organisms with candidate modulators or mimics and selecting for one or more candidate modulators which show modulatory effects. Design and Screening of Duplexed Oligomeric Compounds:

In screening and target validation studies, oligomeric compounds of the invention can be used in combination with their respective complementary strand oligomeric compound to form stabilized double-stranded (duplexed) oligonucleotides. In accordance with the present invention, duplexes comprising the oligomeric compounds of the present invention and their complements can be designed to target a small non-coding RNA. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in some embodiments, both strands of the duplex would be complementary over the central nucleobases, each having overhangs at one or both termini, as described supra.

In some embodiments, a duplex comprising an antisense strand having the sequence CGAGAGGCG-GACGGGACCG (SEQ ID NO: 1) may be prepared with blunt ends (no single stranded overhang) as shown:

```
cgagaggcggacgggaccg Antisense Strand (SEQ ID NO: 1)
|||||||||||||||||||
gcucuccgccugcccuggc Complement (SEQ ID NO: 2)
```

In other embodiments, a duplex comprising an antisense strand having the sequence CGAGAGGCG-GACGGGACCG (SEQ ID NO: 1), having a two-nucleobase overhang of deoxythymidine (dT) and its complement sense strand may be prepared with overhangs as shown:

RNA strands of the duplex can be synthesized by methods disclosed herein or purchased from Dharmacon Research Inc., (Lafayette, Colo.).

For double-stranded compounds of the invention, once synthesized, the complementary strands are annealed. The single strands are aliquoted and diluted to a concentration of 50 µM. Once diluted, 30 µL of each strand is combined with 15 µL of a 5× solution of annealing buffer. The final concentration of the buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the double-stranded compounds are used in experimentation. The final concentration of the duplexed compound is 20 µM. This solution can be stored frozen (−20° C.) and freeze-thawed up to 5 times.

Once prepared, the double-stranded compounds are evaluated for their ability to modulate target levels, expression or function. When cells reach 80% confluency, they are treated with synthetic double-stranded compounds comprising at least one oligomeric compound of the invention. For cells grown in 96-well plates, wells are washed once with 200 µL OPTI-MEM™-1 reduced-serum medium (Gibco BRL) and then treated with 130 µL of OPTI-MEM™-1 containing 12 µg/mL LIPOFECTIN™ (Invitrogen Corporation, Carlsbad, Calif.) and the desired double stranded compound at a final concentration of 200 nM. After 5 hours of treatment, the medium is replaced with fresh medium. Cells are harvested 16 hours after treatment, at which time RNA is isolated and target reduction measured by real-time RT-PCR.

For use in drug discovery, oligomeric compounds of the present invention are used to elucidate relationships that exist between small noncoding RNAs, genes or proteins and a disease state, phenotype, or condition. These methods include detecting or modulating a target comprising contacting a sample, tissue, cell, or organism with the oligomeric compounds and compositions of the present invention, measuring the levels of the target and/or the levels of downstream gene products including mRNA or proteins encoded thereby, a related phenotypic or chemical endpoint at some time after treatment, and optionally comparing the measured value to an untreated sample, a positive control or a negative control. These methods can also be performed in parallel or in combination with other experiments to determine the function of unknown genes for the process of target validation or to determine the validity of a particular gene product as a target for treatment or prevention of a disease.

The oligomeric compounds and compositions of the present invention can additionally be utilized for diagnostics, therapeutics, prophylaxis and as research reagents and kits. Such uses allows for those of ordinary skill to elucidate the function of particular non-coding or coding nucleic acids or to distinguish between functions of various members of a biological pathway.

For use in kits and diagnostics, the oligomeric compounds and compositions of the present invention, either alone or in combination with other compounds or therapeutics, can be

```
cgagaggcggacgggaccgTT  Antisense Strand (SEQ ID NO: 3)
|||||||||||||||||||
TTgcucuccgccugcccuggc  Complement Sense Strand (SEQ ID NO: 4)
``` used as tools in differential and/or combinatorial analyses to elucidate expression patterns of a portion or the entire complement of non-coding or coding nucleic acids expressed within cells and tissues.

As one non-limiting example, expression patterns within cells or tissues treated with one or more oligomeric compounds or compositions of the invention are compared to control cells or tissues not treated with the compounds or compositions and the patterns produced are analyzed for differential levels of nucleic acid expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Cell Culture and Oligonucleotide Treatment:

The effects of oligomeric compounds on target nucleic acid expression or function can be tested in any of a variety of cell types provided that the target nucleic acid is present at measurable levels. This can be readily determined by methods routine in the art, for example Northern blot analysis, ribonuclease protection assays, or real-time RT-PCR. Cell types used for such analyses are available from commerical vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to: T-24 cells, A549 cells, normal human mammary epithelial cells (HMECs), MCF7 cells, T47D cells, BJ cells, B16-F10 cells, human vascular endothelial cells (HUVECs), human neonatal dermal fibroblast (NHDF) cells, human embryonic keratinocytes (HEK), 293T cells, HepG2, human preadipocytes, human differentiated adipocytes (preapidocytes differentiated according to methods known in the art), NT2 cells (also known as NTERA-2 cl.D1), and HeLa cells.

Treatment with Oligomeric Compounds:

In general, when cells reach approximately 80% confluency, they are treated with oligomeric compounds of the invention. Oligomeric compounds are introduced into cells using the cationic lipid transfection reagent LIPOFECTIN® (Invitrogen Life Technologies, Carlsbad, Calif.). Oligomeric compounds are mixed with LIPOFECTIN® in OPTI-MEM® (Invitrogen Life Technologies, Carlsbad, Calif.) to achieve the desired final concentration of oligomeric compound and LIPOFECTIN®. Before adding to cells, the oligomeric compound, LIPOFECTIN® and OPTI-MEM® are mixed thoroughly and incubated for approximately 0.5 hrs. The medium is removed from the plates and the plates are tapped on sterile gauze. Each well of a 96-well plate is washed with 150 µl of phosphate-buffered saline or Hank's balanced salt solution. Each well of a 24-well plate is washed with 250 µL of phosphate-buffered saline or Hank's balanced salt solution. The wash buffer in each well is replaced with 100 µL or 250 µL of the oligomeric compound/OPTI-MEM®/LIPOFECTIN® cocktail for 96-well or 24-well plates, respectively. Untreated control cells receive LIPOFECTIN® only. The plates are incubated for approximately 4 to 7 hours at 37° C., after which the medium is removed and the plates are tapped on sterile gauze. 100 µl or 1 mL of full growth medium is added to each well of a 96-well plate or a 24-well plate, respectively. Cells are harvested 16-24 hours after oligonucleotide treatment, at which time RNA can be isolated and target reduction measured by real-time RT-PCR, or other phenotypic assays performed. In general, data from treated cells are obtained in triplicate, and results presented as an average of the three trials.

In some embodiments, cells are transiently transfected with oligomeric compounds of the instant invention. In some embodiments, cells are transfected and selected for stable expression of an oligomeric compound of the instant invention.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide may be selected from ISIS 13920 (TCCGTCATCGCTCCTCAGGG, SEQ ID NO:5) which is targeted to human H-ras, or ISIS 18078, (GTGCGCGCGAGCCCGAAATC, SEQ ID NO:6) which is targeted to human Jun-N-terminal kinase-2 (JNK2) or another suitable positive control. Controls are 2'-O-methoxyethyl gapmers (2'-O-methoxyethyls shown in bold) with a phosphorothioate backbone or having chemical modifications similar to the oligonucleotides being tested. For mouse or rat cells the positive control oligonucleotide may be ISIS 15770 (ATGCATTCTGCCCCCAAGGA, SEQ ID NO:7), a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) or other suitable control target RNA may then be utilized as the screening concentration for new oligonucleotides in subsequent experiments for that cell line. If 80% inhibition is not achieved, the lowest concentration of positive control oligonucleotide that results in 60% inhibition of target expression or function is then utilized as the oligonucleotide screening concentration in subsequent experiments for that cell line. The concentrations of oligonucleotides used herein can range from 10 nM to 300 nM. For double-stranded oligomeric compounds, the concentration may be determined based upon the molecular weight of both strands together as a single active compound, or may treated as if each strand represents a single active compound and adjusted accordingly, such as halved, for example.

Examples of methods of gene expression analysis known in the art include DNA arrays or microarrays (Brazma et al., FEBS Lett., 2000, 480, 17-24; Celis et al., FEBS Lett., 2000, 480, 2-16), SAGE (serial analysis of gene expression) (Madden et al., Drug Discov. Today, 2000, 5, 415-425), READS (restriction enzyme amplification of digested cDNAs) (Prashar et al., Methods Enzymol., 1999, 303, 258-72), TOGA (total gene expression analysis) (Sutcliffe et al., Proc. Natl. Acad. Sci. U.S.A., 2000, 97, 1976-81), protein arrays and proteomics (Celis et al., FEBS Lett., 2000, 480, 2-16; Jungblut et al., Electrophoresis, 1999, 20, 2100-10), expressed sequence tag (EST) sequencing (Celis et al., FEBS Lett., 2000, 480, 2-16; Larsson et al., J. Biotechnol., 2000, 80, 143-57), subtractive RNA fingerprinting (SuRF) (Fuchs et al., Anal. Biochem, 2000, 286, 91-98; Larson et al., Cytometry, 2000, 41, 203-208), subtractive cloning, differential display (DD) (Jurecic et al., Curr. Opin. Microbiol., 2000, 3, 316-21), comparative genomic hybridization (Carulli et al., J. Cell Biochem. Suppl., 1998, 31, 286-96), FISH (fluorescent in situ hybridization) techniques (Going et al., Eur. J. Cancer, 1999, 35, 1895-904), mass spectrometry methods (To, Comb. Chem. High Throughput Screen, 2000, 3, 23541) and real-time quantitative RT-PCR (Heid et al., Genome Res., 1996, 6(10), 986-94).

Analysis of Oligonucleotide Inhibition of Target Levels or Expression:

Modulation of target levels or expression can be assayed in a variety of ways known in the art. For example, target nucleic acid levels can be quantitated by, e.g., Northern blot analysis, competitive polymerase chain reaction (PCR), or real-time quantitative PCR (also known as real-time PCR). Real-time PCR is presently preferred. RNA analysis can be performed on total cellular RNA or poly(A)+ mRNA. Methods of RNA isolation are well known in the art. Northern blot analysis is also routine in the art. Real-time PCR can be conveniently accomplished using the commercially available ABI PRISM™ 7600, 7700, or 7900 Sequence Detection System, available from PE-Applied Biosystems, Foster City, Calif. and used according to manufacturer's instructions.

Real-Time Quantitative PCR Analysis of a Target RNA Levels:

Quantitation of a target RNA levels is accomplished by real-time PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of RNA from untreated control samples generates a standard curve that is used to quantitate the percent inhibition after oligonucleotide treatment of test samples.

Prior to quantitative PCR analysis, primer/probe sets specific to the target gene (or RNA) being measured are evaluated for their ability to be "multiplexed" with a GAPDH amplification reaction. In multiplexing, both the target gene (or RNA) and the internal standard gene GAPDH are amplified concurrently in a single sample. In this analysis, RNA isolated from untreated cells is serially diluted. Each dilution is amplified in the presence of primer/probe sets specific for GAPDH only, target gene (or RNA) only ("single-plexing"), or both (multiplexing). Following PCR amplification, standard curves of GAPDH and target RNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer/probe set specific for that target is deemed multiplexable. Other methods of PCR are also known in the art.

PCR reagents were obtained from Invitrogen Corporation, (Carlsbad, Calif.). Prior to the real-time PCR, a reverse transcriptase (RT) reaction is performed to generate a cDNA template for real-time PCR. The RT and real-time PCR are performed in the same well, by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene (or RNA) target quantities obtained by real time PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers are designed to hybridize to the target sequence.

Northern Blot Analysis of Target RNA Levels:

Eighteen hours after treatment, cell monolayers are washed twice with cold PBS and lysed in 1 mL RNAZOL™ (TEL-TEST "B" Inc., Friendswood, Tex.). Total RNA is prepared following manufacturer's recommended protocols. Twenty micrograms of total RNA is fractionated by electrophoresis through 1.2% agarose gels containing 1.1% formaldehyde using a MOPS buffer system (AMRESCO, Inc. Solon, Ohio). RNA is transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer is confirmed by UV visualization. Membranes are fixed by UV cross-linking using a STRATALNKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect a target, a target specific primer/probe set is prepared for analysis by PCR. To normalize for variations in loading and transfer efficiency, membranes can be stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data can be normalized to GAPDH levels in untreated controls.

The compounds and compositions of the invention are useful for research and diagnostics, because these compounds and compositions hybridize to nucleic acids or interfere with the normal function of these nucleic acids. Hybridization of the compounds and compositions of the invention with a nucleic acid can be detected by means known in the art. Such means may include conjugation of an enzyme to the compound or composition, radiolabeling or any other suitable detection means. Kits using such detection means for detecting the level of selected proteins in a sample may also be prepared.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder presenting conditions that can be treated, ameliorated, or improved by modulating the expression of a selected small non-coding target nucleic acid is treated by administering the compounds and compositions. For example, in one non-limiting embodiment, the methods comprise the step of administering to or contacting the animal, an effective amount of a modulator or mimic to treat, ameliorate or improve the conditions associated with the disease or disorder. The compounds of the present invention effectively modulate the activity or function of the small non-coding RNA target or inhibit the expression or levels of the small non-coding RNA target. In one embodiment, the activity or expression of the target in an animal is inhibited by about 10%. In another embodiment the activity or expression of a target in an animal is inhibited by about 30%. Further, the activity or expression of a target in an animal is inhibited by 50% or more, by 60% or more, by 70% or more, by 80% or more, by 90% or more, or by 95% or more.

The reduction of target expression levels may be measured in serum, adipose tissue, liver or any other body fluid, tissue or organ of the animal known to contain the small non-coding RNA or its precursor. Further, the cells contained within the fluids, tissues or organs being analyzed may express a nucleic acid molecule produced by a gene downstream from and regulated or modulated by the small non-coding RNA target itself.

Compositions and Methods for Formulating Pharmaceutical Compositions

The present invention also includes pharmaceutical compositions and formulations that include the oligomeric compounds and compositions of the invention. Compositions and methods for the formulation of pharmaceutical compositions are dependent upon a number of criteria, including, but not limited to, route of administration, extent of disease, or dose to be administered. Such considerations are well understood by those skilled in the art.

The oligomeric compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

The oligomeric compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. Suitable examples include, but are not limited to, sodium and postassium salts.

In the context of the present invention, suitable organisms which may be contacted with oligomeric compounds include animals. An animal subject may be a mammal, such as a mouse, a rat, a dog, a hamster, a pig, or a non-human primate. In some embodiments, the animal subject may be a human or a human patient. In certain embodiments, the subject may be in need of modulation of epigenetic control of gene expression.

In some embodiments of the invention, compositions for administration to a subject will comprise modified oligonucleotides having one or more modifications, as described herein.

Analysis of Protein Levels:

Protein levels of a downstream target modulated or regulated by a small non-coding RNA can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vitro Assays:

Once modulators are designed or identified by the methods disclosed herein, the oligomeric compounds are further investigated in one or more phenotypic assays, each having measurable endpoints predictive or suggestive of efficacy in the treatment, amelioration or improvement of physiologic conditions associated with a particular disease state or condition.

Phenotypic assays, kits and reagents for their use are well known to those skilled in the art and are herein used to investigate the role and/or association of a target in health and disease. Representative phenotypic assays include cell cycle assays, apoptosis assays, angiogenesis assays (e.g. endothelial tube formation assays, angiogenic gene expression assays, matrix metalloprotease activity assays), adipocyte assays (e.g. insulin signaling assays, adipocyte differentiation assays), inflammation assays (e.g. cytokine signaling assays, dendritic cell cytokine production assays); examples of such assays are readily found in the art (e.g., U.S. Application Publication No. 20050261218 which is hereby incorporated by reference in its entirety. Additional phenotypic assays include those that evaluate differentiation and dedifferentiation of stem cells, for example, adult stem cells and embryonic stem cells; protocols for these assays are also well known in the art (e.g. Turksen, Embryonic Stem Cells: Methods and Protocols, 2001, Humana Press; Totowa, N.J.; Klug, Hematopoietic Stem Cell Protocols, 2001, Humana Press, Totowa, N.J.; Zigova, Neural Stem Cells: Methods and Protocols, 2002, Humana Press, Totowa, N.J.).

In Vivo Studies:

Animal models used to evaluate the methods and oligomeric compounds of the invention include animal models of tumorigenesis, dyslipidemia, lipid metabolism, glucose metabolism, viral infection, inflammatory diseases, and autoimmune diseases. Examples of such in vivo assays are readily found in the art (e.g., U.S. Application Publication No. 20050261218; Cohen and Miller, Autoimmune Disease Models, 1994, Academic Press, Burlington, Mass.; Svendsen, Handbook of Laboratory Animal Science, 1994, CRC Press, Boca Raton, Fla.).

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Oligomeric Compounds Targeting Small Non-Coding RNAs

In accordance with the present invention, oligomeric compounds were designed to target different regions of small non-coding target RNAs. The oligomeric compounds can be investigated for their effect on small non-coding RNA levels by quantitative real-time PCR. The target regions to which these sequences are complementary are herein referred to as "suitable target regions."

Example 2

Oligomeric Compounds that Mimic or Replace Small Non-Coding RNAs

In accordance with the present invention, oligomeric compounds were designed to mimic the structure and/or function of small non-coding RNAs. These mimics may include isolated single-, double-, or multiple-stranded compounds, any of which may include regions of intrastrand nucleobase complementarity, said regions capable of folding and forming a molecule with fully or partially double-stranded or multiple-stranded character based on regions of precise or imperfect complementarity. The oligomeric compound mimics can then be investigated for their effects on a cell, tissue or organism system lacking endogenous small non-coding RNAs or systems with aberrant expression of small non-coding RNAs using the screening methods disclosed herein or those commonly used in the art. Changes in levels, expression or function of the small non-coding RNA or its downstream target nucleic acid levels can be analyzed by quantitative real-time PCR as described above.

Example 3

Isolation of Small Noncoding RNAs

In accordance with the present invention, small noncoding RNA samples can be size fractionated and gel purified by methods disclosed herein or those commonly used in the art. Briefly, total RNA is extracted using a guanidine-based denaturation solution and standard methods known in the art. Subsequently, low molecular weight RNA is isolated by anion-exchange chromatography (RNA/DNA Midi Kit, Qiagen, Valencia, Calif.). Small RNAs are further resolved by electrophoresis on 15% polyacrylamide (30:0.8) denaturing gels containing 7 M urea in TBE buffer (45 mM Tris-borate, pH 8.0, 1.0 mM EDTA), and a gel slice containing RNAs of approximately 15 to 35 nucleotides (based on RNA oligonucleotide size standards) is excised and eluted in 0.3 M NaCl at 4° C. for approximately 16 hours. The eluted RNAs are then precipitated using ethanol and resuspended in diethyl pyrocarbonate-treated water.

Example 4

SnoRNAs Targeted or Mimicked by Oligomeric Compounds

In accordance with the present invention, oligomeric compounds can be designed to target or mimic one or more small non-coding RNA genes or gene products. Certain genetic loci encoding small non-coding RNAs have been reported; for example, DNA sequences encoding snoRNAs have been identified, often occurring within intronic sequences of other genes. These snoRNAs can be targeted or mimicked by oligomeric compounds of the present invention.

Some snoRNA targets are shown in Table 1. The gene name for each of the targets is given in the table as well as a GenBank Accession number. Also shown is the nucleotide sequence for each. The sequence is written in the 5' to 3' direction and is represented in the DNA form. It is understood that a person having ordinary skill in the art would be able to convert the sequence of the targets to their RNA form by simply replacing the thymidine (T) with uracil (U) in the sequence. Also noted is any reported association of the snoRNA with a disease state (as reported in the Online Mendelian Inheritance in Man (OMIM) database, available through the internet at www.ncbi.nlm.nih.gov/entrez/query.fcgi?db=OMIM) or any known functional characteristics of the snoRNA.

TABLE 1

Small non-coding RNAs

| GenBank Accession# | Small RNA name | Notes | sequence of the snoRNA gene | SEQ ID NO: |
|---|---|---|---|---|
| AY055808.1 | HBII-438A/B C/D box snoRNA | Prader-Willi syndrome | GGATCGATGATGAGAAT AATTGTCTGAGGATGCT GAGGGACTCATTCCAGA TGTCAATCTGAGGTCC | 8 |
| AF081279.1 | U25 snoRNA | (within intron of UHG host gene) | TTCCTATGATGAGGACC TTTTCACAGACCTGTACT GAGCTCCGTGAGGATAA ATAACTCTGAGGAGA | 9 |
| AJ243200.1 | U83 C/D box small nucleolar RNA | (2'-O-methylation guide) | GCCAAATGATGTTTATTT GAAACAGGAGCACCTCA GTGCAAGGACGACTCTT ATCTATCACCCATGACT GATGGCT | 10 |
| AY055807.1 | HBII-437 C/D box snoRNA | Prader-Willi syndrome | GCTTAATGATGAGAATC ATTATTTCTTGAATTGGA TGACACTTTCCATTCCTG CAAAGGGAGCGTGAGGG C | 11 |
| AY055806.1 | HBII-436 C/D box snoRNA | Prader-Willi syndrome | GGTTCATGATGACACAG GACCTTGTCTGAACATA ATGATTTCAAAATTTGA GCTTAAAAATGACACTC TGAAATC | 12 |
| AJ311853.1 | U86 C/D box snoRNA AJ311853.1 is 100% identical to BC004937 over residues 20-86 of AJ311853. | encoded by an intron of the NOP56 gene (nucleolar protein with KKE/D repeat). NOP56 contains putative snoRNA binding domain | GATCACGGTGATGGCTG ACCAGGGCTCCCTGACC TATACAGGCCTCTGCTAT GGGGGTGATGGCCAGTC CTGGTGTCTGAGTGATT | 13 |
| AJ243199.1 | U84 C/D box snoRNA | putative 2'-O-ribose methylation guide snoRNA lacking complementarity to ribosomal RNAs | GCCATATGATGTTTCTT TTCGAAAGGTGAGCGCT TTGCGCAGTGATGACCC TCATCTATCACCCTTGAC TGATGGCT | 14 |
| AJ243222.1 | mgU6-53 snoRNA | putative 2'-O-methylation guide snoRNA for U6 snRNA | TCCCAATGATGAGTTGC CATGCTAATACTGAGCC ACCAGGTAGGGCAGTGT TGCCTGGTTTGGGTGCC AGTGAGTTTAACAAAAC TTCTCACATGAAGATGT GAGGGGT | 15 |
| AJ009638.1 | Z32 small nucleolar RNA | Z32 is a methylation guide snoRNA for the Am30 residue in U2 snRNA | GGGCAATGATGAAAAGG TTTTACTACTGATCTTTG TAACTATGATGGTTTCTA CACTTGACCTGAGCTC | 16 |
| NR_000008 | intron-encoded U22 small nucleolar RNA | U22 snoRNA (nt797-921 GenBank Acc# L36588.1) is cotranscribed with other snoRNAs as part of the UHG pre-mRNA transcript | TCCCAATGAAGAAACTT TCACATGTCTTACTCTCT GTCCTAGTCCCAGAGCC TGTAAAGGTGAACCACT GGGACTGGCTGGGGAG AAGAGGAAGATTTGTTC CAGAAGGAACTGTCTGA GGGAT | 17 |

The snoRNA sequences disclosed above can be used in certain embodiments of the present invention. Structured regions of snoRNAs, such as H/ACA and C/D boxes, are known in the art and have been reported to target the conversion of uridine into pseudouridine, or to direct the 2'-O-methylation of riboses, respectively, within RNA molecules. These structured regions of snoRNAs are believed to play important functional roles in assembly and function of ribonucleoprotein particles (RNPs). Targeting these structures in snoRNAs or small non-coding RNA sequences involved in guiding the activity of a RNP at the site of epigenetic control of gene expression or heterochromatin formation or function is encompassed by certain embodiments of the present invention.

These oligomeric compounds can target the entire snoRNA or small non-coding RNA, or substructures or domains within the snoRNA or small non-coding RNA. Domains within snoRNAs to be targeted include, but are not limited to, the box H, box ACA, box C, box C', box D, box D' motifs, as well as to U-turns, K-turns, and loop structures. Sites to the 5' end of the box D and box D' motifs of C/D box snoRNAs are also preferred as targets for compounds capable of blocking the association of a snoRNA with other biomolecules which will effectively modulate snoRNA function.

The oligomeric compound targeting snoRNAs or small noncoding RNAs can then be investigated for their affects on a cell, tissue or organism system lacking endogenous snoRNAs or systems with aberrant expression of snoRNAs by screening methods disclosed herein or those commonly used in the art. Changes in expression levels of the snoRNA, small non-coding RNA or its downstream target levels can be analyzed by Northern analysis, ribonuclease protection assays (RPA), or quantitative real-time PCR as described in other examples herein. Furthermore, the subcellular localization of the targeted snoRNAs or small non-coding RNAs can be assessed using methods known in the art (such as labeling the compounds followed by fluorescence in situ hybridization (FISH) or other visualization tool), and this data may be correlated with alteration in function or temporal expression of the snoRNA, the small non-coding RNA or its downstream targets.

Example 5

Oligomeric Compounds that Mimic or Replace Small Nucleolar RNAs

In some embodiments of the invention, oligomeric compounds can be designed to mimic the structure or function of snoRNAs. Oligomeric compounds can be designed to include and mimic structured regions of snoRNAs or small non-coding RNA sequences, and these oligomeric compounds may be designed to guide the activity of a RNP to sites of epigenetic control of gene expression or heterochromatin formation or function.

Oligomeric compounds of the present invention can also be designed to mimic the snoRNA structure, or parts thereof, while incorporating certain chemical modifications that alter one or more properties of the snoRNA mimic, thus creating a construct with superior attributes over the endogenous snoRNA. These oligomeric compounds can mimic the entire snoRNA or small non-coding RNA, or substructures or domains within the snoRNA or small non-coding RNA. Domains within snoRNAs to be mimicked include, but are not limited to, the box H, box ACA, box C, box C', box D, box D' motifs, as well as to U-turns, K-turns, and loop structures. Sites to the 5' end of the box D and box D' motifs of C/D box snoRNAs believed to specify the association of a snoRNA with other biomolecules may be preferable as regions serving as the basis for design of mimics.

The oligomeric compound mimics can then be investigated for their affects on a cell, tissue or organism system lacking endogenous small non-coding RNAs or systems with aberrant expression of small non-coding RNAs by screening methods disclosed herein or those commonly used in the art. Changes in expression levels of the small non-coding RNA or its downstream target levels can be analyzed by Northern analysis, ribonuclease protection assays (RPA), or quantitative real-time PCR as described in other examples herein. Furthermore, the subcellular localization of these small non-coding RNA mimics can be assessed using methods known in the art (such as labeling the compounds followed by fluorescence in situ hybridization (FISH) or other visualization tool), and this data may be correlated with alteration in function or temporal expression of the snoRNA, small non-coding RNA or its downstream targets.

Example 6

List of Proteins Involved in Heterochromatin Modulation

Several genes are known in the art to encode proteins involved in heterochromatin formation or function. The proteins encoded by these genes may be components of ribonucleoprotein complexes involving small non-coding RNAs. Furthermore, these genes may be, at least in part, regulated by small non-coding RNAS. Small non-coding RNAs may bind genomic DNA in the promoters, enhancers or other regulatory regions of these genes and direct DNA or protein modification by methylation, demethylation, acetylation, or deacetylation, which may epigenetically regulate gene expression and/or alter the formation or function of heterochromatin. Oligomeric compounds of the present invention may be used to target or mimic the small non-coding RNAs involved in these ribonucleoprotein complexes and modulate their cellular activities.

TABLE 2

| Genes encoding heterochromatin-associated proteins | | |
|---|---|---|
| Gene | GenBank Accession # | Notes |
| chromodomain helicase DNA binding protein 1 | NM_001270.1 | chromodomains and SNF2-related helicase/ATPase domains. CHD genes alter gene expression possibly by modification of chromatin structure |
| chromodomain helicase DNA binding protein 1-like | NM_004284.1 | chromodomains and SNF2-related helicase/ATPase domains. CHD genes alter gene expression possibly by modification of chromatin structure |
| chromodomain helicase DNA binding protein 2 | NM_001271.1 | chromodomains and SNF2-related helicase/ATPase domains. CHD genes alter gene expression possibly by modification of chromatin structure |

TABLE 2-continued

Genes encoding heterochromatin-associated proteins

| Gene | GenBank Accession # | Notes |
|---|---|---|
| chromodomain helicase DNA binding protein 3 | NM_001272.1 | chromodomains and SNF2-related helicase/ATPase domains. CHD genes alter gene expression possibly by modification of chromatin structure |
| chromodomain helicase DNA binding protein 4 | NM_001273.1 | chromodomains and SNF2-related helicase/ATPase domains. CHD genes alter gene expression possibly by modification of chromatin structure |
| chromodomain protein, Y chromosome, 1 | NM_004680.1 | located in the nonrecombining portion of the Y chromosome (NRY). Contains chromodomain and a putative catalytic domain. May have arisen by retroposition. |
| chromodomain protein, Y chromosome-like | NM_004824.1 | located in the nonrecombining portion of the Y chromosome (NRY). Contains chromodomain and a putative catalytic domain |
| HP1alpha | NM_012117.1 | HP1gamma andHP1alpha associate with nucleoplasmic N terminus of lamin B receptor at the interface of the nuclear lamina and heterochromatin, adjacent to the inner nuclear membrane |
| HP1gamma | NM_016587.1 | HP1gamma andHP1alpha associate with nucleoplasmic N terminus of lamin B receptor at the interface of the nuclear lamina and heterochromatin, adjacent to the inner nuclear membrane |
| HP1beta/HSM1 | NM_006807.1 | Found in autoimmune sera along with CENPs. Suv39h HMTases methylate histone H3 K9, and HP1s bind methylated H3 K9 |
| HP1-BP74 | NM_016287.1 | (likely ortholog of mouse heterochromatin protein 2, binding protein 3) |
| SUV39H1 | NM_003173.1 | human homolog of *Drosophila* PEV modifier Su(var)3-9 and of *S. pombe* silencing factor clr4. encodes heterochromatic protein that transiently associates with centromeres during mitosis |
| homolog of *Drosophila* MOF | AL050395.1 | acetyltransferase involved in dosage compensation in flies |
| RAE1 (RNA export 1, *S. pombe*) homolog | NM_003610.1 | mRNA export factor; interacts with nuclear pore |
| skb1 (*S. pombe*) homolog | NM_006109.1 | protein methyltransferase superfamily; negative regulation of mitosis in fission yeast; scr.priority 349 |
| similar to *S. pombe* dim1 | NM_006701.1 | associates with pre-mRNA splicing proteins; Yeast 18S rRNA dimethylase (Tollervey); interacts with APC/cyclosome; essential for mitosis |
| CENP-A | NM_001809.2 | Centromere protein |
| CENP-B | NM_001810.4 | Centromere protein |
| CENP-C | NM_001812.1 | Centromere protein |
| CENP-D | | Centromere protein |
| CENP-E | NM_001813.1 | Centromere protein |
| CENP-F | NM_016343.2 | Centromere protein |
| CENP-G | | Centromere protein |
| CENP-H | NM_022909.3 | Centromere protein |
| CENP-I | NM_006733.2 | Centromere protein |
| INCENP | NM_020238.1 | Centromere protein. INCENP-Aurora B kinase complex helps coordinate chromosome segregation, spindle behavior, and cytokinesis during mitosis. |
| Zeste-white 10(ZW10) | NM_004724.2 | Involved in chromosome segregation during anaphase of mitosis and both meiotic divisions. |
| Sjogren's syndrome/scleroderma autoantigen 1 (SSSCA1) | NM_006396.1 | Centromeric autoantigen 27-kD |
| MAD2L1 | NM_002358.2 | Cell cycle checkpoint protein |
| MAD2L2 | NM_006341.2 | Cell cycle checkpoint protein |
| MAD1L1 | NM_003550.1 | Cell cycle checkpoint protein |
| BUB1 | NM_004336.1 | Cell cycle checkpoint protein |

TABLE 2-continued

Genes encoding heterochromatin-associated proteins

| Gene | GenBank Accession # | Notes |
| --- | --- | --- |
| BUBR1 | NM_001211.3 | Cell cycle checkpoint protein |
| BUB3 | NM_004725.1 | Cell cycle checkpoint protein |
| MTS1 | NM_058195.2 | tumor suppressor; involved in Cell cycle checkpoint; predominantly localizes to the nucleolus |
| SUMO1; UBL1 | NM_003352.3 | Ubiquitin-like protein; homolog of yeast SMT3, which functionally associates with MIF2, a centromere protein involved in chromosome segregation at mitosis |
| SUMO3 | NM_006936.2 | small ubiquitin-like modifier; homolog of yeast SMT3, which functionally associates with MIF2, a centromere protein involved in chromosome segregation at mitosis |
| Cdh1/Hec1 | NM_016263.2 | binds to anaphase promoting complex and activate its cyclin ubiquitination activity |
| SGT1 | NM_006704.2 | required for G1/S and G2/M cell cycle transitions. Physically associates with the SCF ubiquitin ligase complex and is required for kinetochore function |
| RANGAP1 | NM_002883.2 | Ras-related GTP binding protein; associates with SUMO-1; concentrated at kinetochores |
| RANBP2 | NM_006267.3 | RAN-binding protein; localizes to kinetochores at mitosis |
| nuclear mitotic apparatus protein 1 (NUMA1) | NM_006185.1 | nuclear protein required for organizing mitotic spindle poles. May be regulated by Ran. Some patients with autoimmune disease have antibodies directed against the NuMA protein. |
| NUFIP1 | NM_012345.1 | Nuclear Fragile X Mental Retardation Protein-interacting protein 1 (NUFIP1); shows RNA-binding activity |
| FXR1 | NM_005087.1 | Fragile X Mental Retardation; RNA binding, polyribosomal association and nucleocytoplasmic shuttling |
| FXR2 | NM_004860.2 | Fragile X Mental Retardation; shuttles between cytoplasm and nucleolus |
| FMR1 | NM_002024.3 | Fragile X Mental Retardation; RNA binding, polyribosomal association and nucleocytoplasmic shuttling |
| FMR2; FRAXE | NM_002025.1 | Mental retardation X-linked; mentally retarded, FRAXE-positive persons exhibit amplification of a GCC nucleotide repeat adjacent to a CpG island in Xq28, which is methylated |
| DDX38 | NM_014003.3 | Homolog of yeast PRP16 |
| chromosome associated protein E (CAPE)/structural maintenance of chromosomes 2-like 1 (SMC2L1) | NM_006444.1 | Involved in mitotic chromosome condensation and DNA repair |
| CAPC/SMC4L1 | NM_005496.3 (variant 1); NM_001002800.1 (variant 2); NM_001002799.1 (variant 3) | Involved in mitotic chromosome condensation and DNA repair |
| OBP-2/Kinesin-like 4 | NM_007317.1 | involved in spindle formation and function, including chromosome segregation |
| mitotic centromere-associated kinesin (MCAK)/Kinesin family member 2C (KIF2C) | NM_006845.2 | microtubule-depolymerizing ATPase |
| RAD21/KIAA0078 | NM_006265.1 | Component of cohesin complex. association of the cohesin complex with chromatin can be regulated by the state of DNA methylation and/or modification of histone tails. |
| Extra spindle poles (ESPL1)/separin | NM_012291.3 | Involved in sister chromatid cohesion |

It has been proposed that the fragile X syndrome is caused by abnormal chromosome imprinting. According to this model, the fragile X mutation leads to an imprint (a stable inactivation of a gene or genes at the fragile X site), because the mutation prevents complete reactivation, before oogenesis, of a mutant fragile X chromosome that had been inactivated in a female for dosage compensation. The basis of this localized block to complete reactivation of a fragile X chromosome was proposed to be late replication of DNA at the fragile site (Laird, Genetics, 1987, 117, 587-99).

It has been reported that the DIS3 protein has been structurally and functionally conserved through evolution; the human DIS3 protein can complement the fission yeast dis3-54 mutant (Shiomi et al., J. Biochem., 1998, 123, 883-90). Using the yeast two-hybrid system, the RAN GTPase was found to directly interact with the DIS3 protein, an exosome component (Noguchi et al., EMBO J., 1996, 15, 5595-605; and Suzuki et al., Genetics, 2001, 158, 613-25).

RanGAP1 is the activating protein for the Ran GTPase. Vertebrate RanGAP1 is conjugated to a small ubiquitin-like protein, SUMO-1. This modification promotes association of RanGAP1 with the interphase nuclear pore complex (NPC) through binding to the nucleoporin RanBP2, also known as Nup358. During mitosis, RanGAP1 is concentrated at kinetochores in a microtubule-(MT) and SUMO-1-dependent fashion. RanBP2 is also abundantly found on kinetochores in mitosis. Ablation of proteins required for MT-kinetochore attachment (Hecl/Ndc80, Nuf2) disrupts RanGAP1 and RanBP2 targeting to kinetochores. RanBP2 and RanGAP1 are targeted as a single complex that is both regulated by and essential for stable kinetochore-MT association (Joseph et al., Curr. Biol., 2004, 14, 611-7).

Several genes are known in the art to encode protein components of nucleoprotein complexes, or proteins with predicted or confirmed ribonuclease activity, and these proteins are believed to be involved in heterochromatin formation or function. The regulation of these genes may be, at least in part, regulated by the binding of small non-coding RNAs in their promoters, enhancers or other regulatory regions. Furthermore, small non-coding RNAs may direct the modification of these genes or their products by methylation, demethylation, acetylation, or deacetylation, which may epigenetically regulate gene expression and/or alter the formation or function of heterochromatin in the promoters, enhancers or other regulatory regions or the genes themselves, or may alter the activity of the gene product. Oligomeric compounds of the present invention may be used to target or mimic the small non-coding RNAs involved in these ribonucleoprotein complexes and modulate their cellular activities.

TABLE 3

Genes encoding RNases or proteins in nucleoprotein complexes (exosome, telomerase)

| Gene | GenBank Accession # | Nucleoprotein complex | Notes |
|---|---|---|---|
| RRP4 | NM_014285; BC000747 | exosome/ Pm-Scl | 3'->5' exonuclease activity |
| PM-Scl100; PMSCL2 | NM_001001998.1 (transcript variant 1); NM_002685.2 (transcript variant 2) | exosome/ Pm-Scl | RNase D-like |
| RRP40 | XM_005323 | exosome/ Pm-Scl | 3'->5' exonuclease activity |
| RRP41 | NM_019037 | exosome/ Pm-Scl | RNase PH-like |
| RRP42 | D29958 | exosome/ Pm-Scl | RNase PH-like; human KIAA0116 |
| OIP2 | AF025438 | exosome/ Pm-Scl | RNase PH-like; similar to XM_069517 |
| DIS3; human KIAA1008 | NM_014953.2 | exosome/ Pm-Scl | RNase R-like; mitotic control protein in S. pombe |
| PM-Scl75; PMSCL1 | NM_005033.1 | exosome/ Pm-Scl | RNase PH-like |
| RRP46 | NM_020158 | exosome/ Pm-Scl | RNase PH-like |
| MTR3 | NM_058219 | exosome/ Pm-Scl | RNase PH-like |
| CSL4 | NM_016046 | exosome/ Pm-Scl | core component of exosome; has S1-RNA binding domain |
| mitotic phosphoprotein 6 (MPP6) | NM_005792 | exosome associated | Chen, et al., 2001 |
| SKIV2L | XM_059782 | exosome associated | helicase-like SKI2W; Chen, et al., 2001 |
| Dyskerin (DKC1) | NM_001363 | snoRNP | associated with disease dyskeratosis congenita 1 |
| NOLA1 | NM_032993; NM_018983 | snoRNP | nucleolar protein family A, member 1 (H/ACA small nucleolar RNPs) |
| NOLA3 | NM_018648 | snoRNP | nucleolar protein family A, member 3 (H/ACA small nucleolar RNPs) |
| NOLA2 | NM_017838 | snoRNP | nucleolar protein family A, member 2 (H/ACA small nucleolar RNPs) |

TABLE 3-continued

Genes encoding RNases or proteins in nucleoprotein complexes (exosome, telomerase)

| Gene | GenBank Accession # | Nucleoprotein complex | Notes |
|---|---|---|---|
| SUPT6H; Suppressor of Ty 6 | NM_003170.2 | copurifies with exosome | may regulate transcription via establishment or maintenance of chromatin structure |
| Spt5 | NM_003169.2 | associates with exosome | elongation factor; chromatin structure regulator |
| exoribonuclease 1 (XRN1); strand exchange protein 1 | NM_019001.2 | 5' to 3' exonuclease activity | preference for G4 tetraplex substrates |
| Exonuclease 1 (EXO1) | NM_006027.3 (transcript variant 1); NM_130398.2 (transcript variant 2); NM_003686.3 (transcript variant 3) | 5' to 3' exonuclease activity | DNA repair protein; physically interacts with Werner syndrome protein (WRN) |
| LOC81691 | NM_030941 | Exonuclease NEF-sp | RNA-binding exonuclease |

In addition, several genes that transcribe functional RNAs having characteristics suggesting that the small non-coding RNA products may be involved in heterochromatin formation or function or epigenetic control of gene expression are identified herein.

Example 7

Comparison of Gene Regulatory Regions

Because microRNAs are believed to be involved in genomic transcriptional silencing at promoters and enhancers of genes that are silenced, imprinted, or subject to dosage compensation, it was hypothesized that gene regulatory regions (such as promoters or enhancers) bearing homology to miRNAs may be epigenetic regulatory elements, and that miRNA levels may affect the methylation status of the homologous gene regulatory region, promoter or enhancer, thereby affecting the expression of genes.

A bioinformatic analysis was performed which allowed the prediction of sites within the promoter or enhancer regions of human genes exhibiting complementarity to small non-coding RNAs. Such sites within promoters or enhancers could be considered miRNA binding sites, or to exhibit homology to a miRNA. In the context of this bioinformatic analysis, a gene regulatory region of DNA having "homology" to a miRNA indicates a sequence that is "cognate to", or complementary to, a miRNA sequence.

In some embodiments, as a first step, the first exon in each of 23,000 genes contained in an in-house database was identified. Within the first exon, the first AUG was then identified as the translation start site in each of the 23,000 genes. Next, the sequences directly upstream from each translation start site, encompassing a genomic fragment 1-kilobases (kb) in length, was retrieved for each gene; these were considered the promoter regions. Sequences downstream from the RNA polymerase binding site in the promoter (such as within the 5'-UTR, an intron, an exon, or the 3'-UTR) are considered to be enhancer regions. These promoter and enhancer regions were then compared (using a BLAST-based algorithm) to an in-house database of sequences representing mature microRNAs (miRNAs). Thus, sites within the 23,000 promoter or enhancer regions exhibiting complementarity to a mature microRNA sequence were identified. Using this method, a subset of ten promoters/enhancers with at least 80% complementarity to miRNAs resulted. These are shown in Table 4. The miRNAs are listed in Table 5. CG dinucleotides are indicated in bold and sites chosen for analysis by the MSP method are underlined.

TABLE 4

Promoter/enhancer regions of genes having homology to miRNAs

| Gene name | 1 kb Promoter/Enhancer sequence | SEQ ID NO: |
|---|---|---|
| DiGeorge syndrome critical region gene 8 (DGCR8) | CAGGTGGCACCCAGGCGTCTCTGTGCCTCGGCTCCAGCTG<br>TCTCTTGTGGCTCCCCACCCCAAATCCTGGCAGGTCCCTT<br>CCCCACAGCCACCCACCCCTCTCCTCCATCGGGAACAGA<br>ACTATGCTGCCACCTCTGGTGACCTCAGCACGCTGCATCA<br>CTGTCCCCGTCCACGTGCTACCCTGTGGGCCCAGGAGAG<br>CCCTGGGGTCCCTGGGTAGCAGAGCGCCTGGCCATGCCT<br>CTGAGGCCCCTAGTGCCGCAGAGTTGAGCTGAGGGTCTC<br>GCGCTCGCCCTCTGACTGACCCAGCCCTTGCAGGTGAGT<br>GGATTGCTGTGCTCTGGTGGCCTGAGGGAGGCCACGCGC<br>CTTCTGTGTGTTCCAGAAAGGGTGCCTCCCACTGCATGCT<br>TGCTTATCTGAGTTAGAAGAATGCTGTGGTGGAGTTTAGT<br>GTAAATTTTTAAAATATTTTTTGAGCCTTATGATTATATA<br>GTTTTTGTGTTTCTGAAGTAGGAATTAAAGTGGGCATTAA<br>CAAAATATTTAACTTTGGACTTAAGTTATAATTCAGGTTC | 18 |

TABLE 4-continued

Promoter/enhancer regions of genes having homology to miRNAs

| Gene name | 1 kb Promoter/Enhancer sequence | SEQ ID NO: |
|---|---|---|
| | TGAAGAATAAAAGTAAGGTTAGTTTGTTTTGATGCCTAAA<br>AAGTCCTCTTAGGGAATATTATTTTGAAGCCCTTTACTAT<br>GCTGTTAATAGTGCTTGGCTTTTAACTTGGTACCAGGGAA<br>TTGGAAGGTTTCTGTCATTTTGTGACGATATTTTTAAATTT<br>CTTTGCAGGTAGAAGAGAAAGGTGCCACTCCGGCATGA<br>AGACAGACTCGCTTAGTCGCCAGTCACTTAAGCTGAGTG<br>CATTGTGATTTCCAATAATTGAGGCAGTGGTTCTAAAAGC<br>TGTGTACATTAATGAAAAGAGCAATGTGGCCAGCTTGAC<br>TAAGCCGCCAGCCGCACAGCGCGGCAGGACGCGCCCGG<br>GTGTCAGCGGACTTGTGCATGTTAGCTGTGTAGATTTATG<br>TGAGGGCTTGTAAAACTCTGGTCTTGTAAACTAGTCTTAA<br>GCGCTTTTAAT | |
| Hypothetical<br>protein<br>DKFZp761P1121<br>Chromosome 16<br>open reading<br>frame 7(C16orf7) | GTGGCCCGTTCCTGAGATGGGGCCGAATCTAAGGTTGGC<br>GACCAGGTAGAGAAGCTGGCCCAGCCACACCCGGCTGCC<br>CAAGGAGGGAAGGAGCCTGCCTGTGCCTAGGAGAAGCCT<br>CGTTCCTGAATCTGCTGCTTTCCCCAAGTTGGTTTTTAGG<br>GCAGCAGGTGCCCCCCGCAAGTCAGAAATCCTGCCTGGAT<br>TATATTTCGTCTTTCTCTGAGGCATAGACTTAAAGATA<br>GGAAACTTAACAGCTAGGGATAAAACAAAAAAACATAG<br>CATATTGCTGGGCGCTGTGGTTCACGCCTGTAATCGTGAC<br>ACTTTGGGAGGCCCAGGCGGTGGATCACCTGAGGTGAGG<br>AGTTTGAGACCAGCCTGGCCAACGTGGTGAAACCCCGTC<br>TCTACTAAAAATACAAAAATTAGCTGGGTGTGGCGGTGC<br>ACACCTGTAATCCTAGCTCCTGGGAGGCTGAGGGATGA<br>GAATCACTTGAACCCAGGAGGCGGAGGTTGCAGTGACTC<br>GAGATCCTGCCACTGCAGTCCAGCCTGGGCGACAGAGTG<br>AGACTCTGTGTCAACAAAACAAAACAAACCACGATTCTG<br>TGGTTCCAATGACCTGTGCGTTGTCAGAGGGGTCACACAG<br>CCTTGAAAGGTAACAGTTCTAGGCTCCTGTGTGCACTGGA<br>AATACGTAACTCGCAGGTTCTGGGAAAGGGATTTCTCGG<br>AACTTAAACCGGGAAGTGATTTGAAAACTTCCAGTATCA<br>CTCCCTTTATCCTCTCAGAAAAGTATTTTTTTAAGCCACTG<br>AATGAATCACCCTTGAGTTGCACAAGAAGGAAACATTGC<br>ATAGAATGAAAAATGACAGCAAACTGCTGAGGTCACTTC<br>CCCAGGCCCACTGAATGAGAATATCAGTTCCTGTGCTGG<br>AGAGAAAGGCAGTCAGAGGAGAAAATGAGGTCCAGCTC<br>GTCCCTGGCTCTCTCTCTCTCAGGTCCTGATGTCTTTTC<br>CAAGTCTGGAGAGCAGCG | 19 |
| hypothetical<br>protein FLJ11753 | GCATGTTATTTCCTGAGGAGTTGTATTTCTTCACCCCTTTT<br>TCCTTTGATCTCATATTCTCTGACTCCAGAGCTTCCCTGAC<br>TCTGTCTTGCAAAATGCTTTACCTAAAGCCTTCTTTAAGC<br>CTTTATTGAGCCCCAAGTCAGCATTAATCTCTTCCCCTCC<br>ATTAAAAAAAAACTGGAATGGCCATTGTATGTATAGTAT<br>GTTCCAGCGTAGGTTAGTTGGCTGTTCTTGTGTCTGTCTC<br>CTACTCTTCTCTAAGCACTAATGGTTTGCTTTCCAATAGA<br>CGGTGAGCTCCTTGAGGATAGCCCCTCTATTTGTATTATG<br>TGGCTTACAGGTTTTAAGCTATAATTTTTTAAGGTTTCATT<br>TTATTTTGATTCTCTATCGATAAGTAACAGACATTGAACT<br>CTTTGTGATAAAGTGTCCTGGAAAGATAGGAGAGAAATG<br>ATAATAAAAAAGATATTAAAATATACTTCAGGAAACATT<br>AGCCAAGTCAATTTAATACAAAGTATATTCAGATGCCCA<br>GGAATACAGAACAGTCATGAGCAGAAATGACCAGTGTTA<br>ATCAAGGAAGTI'CAAACATIT1TGTAGGlTAATGAACAA<br>GTATGGCCTGAAAATAAGCACTGGGCCATGTGGTGATTG<br>GAAAACACAAATGGAAATCCAGAAGGATGAGTGAGGG<br>AAGAGTGATAAACCATCTCTGTAATCTTATGTTTTATGGT<br>ATGTGCAGTGCAAGTTTTATAGCATAGAAACTCTTTGGA<br>AACTATTCAAAGACAGCCCAGTCCAATTTCAAACTTTTGA<br>ACTTCTCTTAGTGGCTACTACTTTTTACACTTTTTCTGGAA<br>TTTTTGTATAACATCTTTATTTTTTCTCAGTTTTATATATA<br>ATCATTATGTACTTACAGGAAGGTAAAGGACAAATTTTA<br>CATATTTTTTTCCACTAAAAGTATATTGCATTCTTTTTTTG<br>TAACAGATTCATGCCCAAGCACAAAACAACCCATTTAAA<br>GAAG | 20 |
| zinc finger protein<br>358 (ZNF358) | GAGAAGGAAGGAAAAGAAGGAAGGAAGGAAAGAAAGA<br>AAGAAAGAGAGAGAGAGAGAGAAAGAAAGAAAGAAGAA<br>AGAAAGAAAGAAAGAAAGAAGAATTGAAGTTAGCTGA<br>GTGTGGTGGTGCATCTGTAATTCCAGCTACTTGAGAGGCC<br>GAGGTGGGAGGATCCGCTTGAGCCCCGGGAGTTCCAGTCTG<br>CAGTGAGCTATGTATGATCACATCACTGCACTCTAGCCTG<br>GGTGACAGAGTGAGACCCCATCTCAAAAAAATAAAATA<br>AAGAAGTGGGGCTGGGGCGCGGTGGCTCACGCCTGTAATC | 21 |

TABLE 4-continued

Promoter/enhancer regions of genes having homology to miRNAs

| Gene name | 1 kb Promoter/Enhancer sequence | SEQ ID NO: |
|---|---|---|
| | CCAGCACTTTGGGAGGCTGAGGCATGCAGATCACCTGAG GTCAGGAGTTTGAGACCAGCCTGTCTAACATGCTGAAAT CCCATCTCTACTAAAAATACAAAAATTAGCCAGGCATGG TGGTGGACACCTGTAATCCCAGCTACTCAGGAGGCTGAG GCAGGAGAGTTGTTTGAACCTGGGAGGCGGAGGTTGCAG TGAGCCGAGATGGTACCTTTGCACTCCAGCCTTGGCAAC AGAACGAGACCCCATCTCAAAAAAAAAAAAAAAAAAAAA AAAGAAGTGGGTTCTGGGGGCACAATCGGGTCCCCGTCTC TCATCCCTAACCAGACTCCAAAAGACACCCCCGCTCCCA CAGAACCCACCTACCCTCTACCCTCTATCCTTGCCCTTGC AGGTCTTGCCCCAGAAGCTGCGGGCACATCCACGCCTGA AATGCGGCGCTCAGTCCTGGTCAGGAACCCAGGCCACAA AGGCCTGAGACCCGTTTATGAAGAGCTCGACTCTGACTC CGAGGACCTAGACCCCAATCCTGAAGATGTGGACCCGGT TTCTGAAGACCCAGAGCCTGATCCTGAAGACCTCAACAC TGTCCCGGAAGACGTGGACCCCAGCTATGAAGATCTGGA GCCCGTCTCGGAGGATCTGGACCCCGACGCCGAAGCTC CGGGGCTCGGAACCCAAGATCCCGACCCC | |
| solute carrier family 12 (potassium/ chloride transporters) member 7 (SLC12A7) | GGAACATTTCCCAAGGAGGGAAGGGAGGGTTCTAGGGCA GGGGCCGCGGGCACTCCTGGGGCAGGTGTGGAGGAGA CTGGGGTCTTCGTGGGTGGTATTTGTCATGGGTGGGGGG GGGGACTCCCTCTACTGGGTTAGGTCCCTAAACTGGAGCT GGACCAAGCTCCGGAGTACCCCACCCCCAGGCTATCCAA GGCTCCTTCCACTGGAGTTGCCTTTGCAGCCAGGTTGGGC TAGCCAGGAGCCAGGCTAGGAGCCCAGGGTCTGAGCGG GTGTTGACAGCCTGGAGTGGGTGGGCGGACTGTGTGGGA GGTGGGTGCTGGAGGATGGCAGGGGGGAACAGGAGGGG GAAGAAGGAGGGGTAGGGGGCTGGAGCAGGAAATGGGG GGCAAACAGGAGGGGGTGCGGGAGGGGGCGCAGAAGG AGGAGGGGCCCAGCAGGAGGGGGTGCAGAAAGGGCAGG GGTTCCAGCAGGAGGGGGTTCATAGGGGGCAGGGGGGCCC AGCAGGAGGGGGTGCAGGAAGGGTGGGGGGTGCAGGA GGGGTGAGGGGTTCCAGCAGAAGGGCGTGCAGGAGGGG CAGGGGGCTGGAGCAGGAGTGGGGGGTCGGGGAAGGGG ACAAGAGGGGAGGCGGGGAGGGGGCCGGGGAGGGCGG GGAGGGCGGGGAGTTCCAGCAGGAGGGGCAGGGGCTG GAGCAGGAGGGGTGCAGGAGACTGAGCGGGGATTCGC GGGCTCTGCGATGGTCGGGAGCCGCAGGCAGCGAAAGCC CCGCGTCCCGGGTCGCGGCGGTCAGACAGACGCAGCCT GGGTTGGGGTCCCTGCAGGAAGTCGCCGCGGGCCAACTT TTCGTGGGGCCGCGGGGCAAGCAGGTGAAGTCACGTGG CCCCGGGGCGGGGCGGGGCGGCTCGGTCGGACCCCGCCCC TGCCTCCAAGTCCCCGTGGCCGTCGGCGGGAGCGGCGCAG CGCGGGCCGGGCCGGGACGGGGACTGTCGGCTGCAGGC GGCC | 22 |
| phosphodiesterase 4A, cAMP-specific (phosphodiesterase E2 dunce homolog, *Drosophila*) (PDE4A) | CCCCGTCTCTACTAAACATACAAAATTAGTCGGGTGTGCT GGAGGGTGCCTGTAATCCCAACTACTCTGGAGGCTGAGG CGGGAGAATTGCTTGAACCTGGAAGGCGGAGGTTGTGGT GAGCCGAGATCGTGCCATTGCACTCCAGCCTGGGCGACA AGAGTGAAAACTCCGTCTCAAAAAAAAAAAAAAGAAATG TGGCTGGTATCCGGTGTCTGTCTATAGGTGTGGGTCTGG ATGTGGGTCTGATGTGGGTCTGTGCCCTTGGATGGGGC GTGTCTGAAGGCATTTGCTATATGCTCAGCTGTGGACCTA TAAGTGTGTTGGACATCAGAGTTGTGACTGTCTCCGGGTG TGTGTGTGTGTGTGCTGTAAGTGTACAACAGAAAGC ATTTGAGTATCTGTGTATATTCAAGTGTCAAGTGCCTGGA TGTGTGTGGGTGTCCCTGGAAGGTGTGTCTCAGGGTGTTT GTACATCTGTGAGTGTAAAGTGGATGTGTGTTTCTGTCTC TGGGTGTGTCCATGGAGGGGATGGGTCCTGATGGGGACA GCCCACCTAGGTTCTGGCTGAGGGCCATGGGCTCTGATGC CCCTTTAATACCCCCCACCCCCAGCACCACCTGACATCC CATGCAGCCTGCCAGTGCTGCAGTGAGCACACACGCACA CACACGGGTGCACACACAGAGCTCCGCAGCCTCCTCCTG GGACCCTTGCCCTGCCCCCCTCCCATGGGCACGGACCCCC CACCCGCCTCCACCCACTGCCGCGGGGGGGCCCCGTTGGGG CCCAGGGCTGGCGGGCCATGTAACCAGGGCTGCTGCTGG GAGCGCGGAGGGGAAGGGAGCCCCCAGCCCTGCTGGGC CGGCCCAGGCCCGTCCGCGGCTCCCCCTTCCACTACCCA CCTGCCCGGCACCCCCTCCCCAGTGGTTGTTAACCCCGG GACTCCCCAAGCCCAGCCTCTGTGTGCAGCAGCCCCAGG CGGGCTAAGTCTCCAAG | 23 |

TABLE 4-continued

Promoter/enhancer regions of genes having homology to miRNAs

| Gene name | 1 kb Promoter/Enhancer sequence | SEQ ID NO: |
|---|---|---|
| Hermansky-Pudlak syndrome-6 (HPS6) | GGCAGTCAAGGGGTGGAAGGACCCCTGCATACAAATTTG<br>TAGGTGTTACTGAAGAGTCGGTACACAGGCTCAGTGCTT<br>CTAAATTATGTTTCTCTGTTTTGGTTTGGGTGATGAGTTGT<br>TGATATGATAAAGTGATTTGTTGCACTGACTCTGGAGCCA<br>GAGTGCCTGTGGTTGAAATCCCACCTCCACCACTTAATAC<br>CTGCTTGATCTTAGTTAAGTTACGTAATCTCTCTGTGCTTC<br>ATCCTCCTTATCTGTAAAAGGGACTAGGGGATAGAGAAG<br>GCTGTCACATAGTGATATGGAAGTGGTTTTCTTTCCTTCC<br>TTCCTTCTCTCTCTCTCTTTCTTTCTTTCTGTCTTTTTAA<br>AATTTTTATAGAGACAAGGTCTGCCTATGTTGCTCAGGCT<br>GGTCTCGAACGCCTGGCCTCAAGCAATGCTCCCACCTCA<br>GCCTCCCAAAGTGCTAAGATTATAGGCGTGAGCCACCGC<br>GCCCAGCCATGTTTACTATTTCCACTAGATTGTCATCTCC<br>ATGAGGTTGAGGTTTTCTATTTTGTTTAGGGCTGTCTACTC<br>AGAGCCTGGCACAAAGCATGTGCTAACGAAAATTTCCT<br>GAATGAGTAAATTGGGGTGAAATTCTTGGGAGAGGGGCT<br>CAGGGGGCTGGAATCCCTATTCCTGCGTGGGACTCCGGG<br>CCACTGGGCGCGTCCTGGGGTCTGGGGAAGGGCCTCCC<br>CCTGCGCCGAGAGCGTGCCCGGGCGGGCGCGGTCCAGG<br>CGCTGAGCCCCTGGGGCGCTCCCGTGGCTCCTCCCCGG<br>CGGGCGTGTAGTGTCGGCCCAGCGACTGCGGGAGGCAT<br>CCCCGGAGCCGGCCGGGCGGGGCGGAGTCGACGCTCGGC<br>CCGGCCTCTGCTCACCTCATCCACGGGAGACGGAAGTCT<br>TGGCCCTGCTCCGCTCCCCCGAGAATCGGGCCTCGCCCT<br>GCTGGGCGGCTGGACCTGGGCAAAGCCTGGGCGCGCTCC<br>CGCGCAGCGGCGCC | 24 |
| hypothetical protein FLJ22595 | TAGTAGAGATGGGGTTTTACCATGTTGACCAGGCTGGTCT<br>TGATGTCCTGGCCTCATGATCCACCCACCTCGGCCTCCCA<br>AAGTGTTGGGATTACAGGCGTGAGCCACCATGCCTGGCC<br>TATATGTTCTTTTAATGCCTTTACCATTATTCTGTGGAGTC<br>TTGGGAAGGAGAGGAAATAAATGCATGTTTTTATTTGCC<br>ATCTTTAATTGGACTGCTTAATGTAAAACTGTTCGTGTTA<br>TAAATTCCCCCTCATATATTTGGTTTTGTGACTGCAGTAG<br>TGTAAATTCTCTGCCTAGAATTTTAAAGAAAGTGATTCTG<br>TATGTGATTAGGGAGTAAGGTTCAGATAACCTTGAGTGG<br>TTTAAAGTTTCCTACTGAGTAATGTGAACAAGGCGGATTT<br>AAGATACTGCAGACAGAGTGTGAGAATAACTCTCTCTTC<br>ACAACTTAAGAAGCCTGGTTCCTTATTTACAACTGGGATA<br>AGATAAATGGTTGAATACCTAGAGAAGTTCCACAAAAAG<br>TTACACAAAAAGTTTAGTTAAATTTAAGTTAAAAGTTAGT<br>TAAAATGAAAAGTTAAGTTTTTATTCTGCTACTAAACCAT<br>GCTCCTCTGCGTGTCTGAACCTTCAGGTTCCTCTAGATTT<br>CTAGCACCTGAAAGAAAACAAAACTGCAGCATCAGCCAG<br>GTAGGCCTCTCCTAATCTTACTCATTCACAGAGAATTTCC<br>CCTTTGAGTCACCATGGCATTGGCTGGTTACTCATACCAC<br>AGATCCCTCAGGATTGGCTGGGACTGCAAATAAAATACT<br>GTTTGCCCATAATCAAGTTGATAAGCTACAACATAAACA<br>CATCTAGGTTCTTGTTCTTAGAATACAGCATGAAGAATTT<br>GCTTTCTTCTTTCTTCCTAACATTTTCATGTGAGATCCAGA<br>AAGGACACATTGTCTCTGGCCATTCGAAGAAAGAAAGAA<br>AGAAAAAAAAAAAAGGTATTTAGAGACAGAGAGAGAAA<br>AAGGCTGAA | 25 |

Table 5 illustrates the miRNAs having complementary sequences in the promoter/enhancer regions of the 1-kb promoter/enhancer sequences subjected to the BLAST analysis. The miRNAs found through this analysis and their cognate sequences in promoter/enhancer regions are shown in Table 5; "%" indicates percent complementarity.

TABLE 5 miRNAs cognate to promoters/enhancers

| name of miRNA | Sequence of miRNA | SEQ ID NO: | Promoter/enhancer | Sequence in promoter/enhancer | SEQ ID NO: | % |
|---|---|---|---|---|---|---|
| hypothetical miRNA-088 | UGUGAUUUCCA AUAAUUGAGG | 26 | DGCR8 | TGTGATTTCC AATAATTGA GG | 26 | 100 |

TABLE 5-continued miRNAs cognate to promoters/enhancers

| name of miRNA | Sequence of miRNA | SEQ ID NO: | Promoter/ enhancer | Sequence in promoter/ enhancer | SEQ ID NO: | % |
|---|---|---|---|---|---|---|
| miR-185 | UGGAGAGAAAG GCAGUUC | 27 | C16orf7 | TGGAGAGAA AGGCAGT | 33 | 88.9 |
| miR-28 (Tuschl) | AAGGAGCUCAC AGUCUAUUGAG | 28 | Hypothetical protein FLJ11753 | CAATAGACG GTGAGCTCCT T | 34 | 86.4 |
| hypothetical miRNA-156 | UGCUUUCCCUC CUUCCUUCUU | 29 | ZNF358 | AAGAAGGAG GAAGGAAAG | 35 | 85.7 |
| hypothetical miRNA-168 | AGCCAGGUGCC UUCACCUGCUU | 30 | SLC12A7 | AGCAGGTGA AGTCACGTG GC | 36 | 85.7 |
| hypothetical miRNA-154 | UUAAAGUGGAU GUGUGUUAUU | 31 | PDE4A | TAAAGTGGA TGTGTGTT | 37 | 81 |
| hypothetical miRNA-156 | UGCUUUCCCUC CUUCCUUCUU | 29 | HPS6 | TGTGATTTCC AATAATTGA GG | 26 | 81 |
| miR-14 | UCAGUCUUUUU CUCUCUCCUA | 32 | Hypothetical protein FLJ22595 | TGGAGAGAA AGGCAGT | 33 | 81 |

From these data, it can be observed that there are ten promoter/enhancer-miRNA pairs in which the miRNA and a sequence within the 1-kb promoter/enhancer region exhibit more than 80% complementarity to each other; sites within eight different promoter/enhancer regions exhibit complementarity seven microRNAs (hypothetical miRNA-156 is complementary to the promoters/enhancers of Zinc finger protein 358 (ZNF358) and Hermansky-Pudlak syndrome-6 (HPS6)).

In some embodiments, the same 23,000 genes used in the first step described above were the basis for retrieval of genomic fragments 6-kb in length directly upstream from each translation start site, encompassing the promoter/enhancer regions of these genes. These promoter/enhancer regions were then compared (using a BLAST-based algorithm) to the in-house database of sequences representing mature miRNAs. Thus, sites within the 23,000 6-kb promoter/enhancer regions exhibiting homology to a mature microRNA sequence were identified. Using this method and the parameter of 100% homology, a subset of thirteen promoters/enhancers resulted. These promoter/enhancer regions exhibiting homology to miRNAs within 6-kb upstream of the translation start site are shown in Table 6, and the miRNAs as well as their cognate sequences in the promoters/enhancers are listed in Table 7. In Table 6, the column labeled "GenBank Accession: (nucleotides in range)" indicates the nucleotide numbers of GenBank Accession number of the range within the GenBank nucleotide sequence which exhibits homology to the miRNA; also in this column, the word "complement" indicates that the range of nucleotides is the complement of the GenBank sequence.

TABLE 6

Promoter/enhancer regions of genes exhibiting homology to miRNAs

| Gene name | GenBank Accession: (nucleotides in range) | miRNA exhibiting homology |
|---|---|---|
| homeobox protein A9 isoform a (HOXA9) | NT_007819.15 (26500750 . . . 26506749) complement | mir-196-2 |
| hypothetical protein MGC14376 | NT_010718.15 (1219234 . . . 1225233) complement | mir-22 |
| dynamin 1 (DNM1) | NT_008470.17 (38280954 . . . 38286953) | miR-95 (Mourelatos) |
| homeo box B7 (HOXB7) | NT_010783.14 (5341559 . . . 5347558) complement | mir-196-2 |
| hypothetical protein FLJ21827 | NT_033899.7 (21992961 . . . 21998960) complement | hypothetical miRNA-168 |
| hypothetical protein FLJ10496 | NT_022517.17 (48995267 . . . 49001266) complement | miR-191c |
| transcriptional activator of the c-fos promoter (CROC4) | NT_004487.17 (6876987 . . . 6882986) complement | miR-9 |
| hypothetical protein FLJ20436 | NT_029419.10 (11216868 . . . 11222867) complement | miR-95 (Mourelatos) |
| sprouty homolog 4 (SPRY4) | NT_029289.10 (2862258 . . . 2868257) complement | hypothetical miRNA-156 |

TABLE 6-continued

Promoter/enhancer regions of genes exhibiting homology to miRNAs

| Gene name | GenBank Accession: (nucleotides in range) | miRNA exhibiting homology |
|---|---|---|
| ring finger protein 1 (RING1) | NT_007592.14 (24029662 . . . 24035661) | mir-219 |
| CD37 antigen | NT_011109.15 (22100988 . . . 22106987) | hypothetical miRNA-156 |
| Gene DKFZP564J0123: nuclear protein E3-3 isoform a | NT_022517.17 (48993582 . . . 48999581) | miR-191c |
| peripheral benzodiazepine receptor-associated protein 1 (BZRAP1) | NT_010783.14 (15058560 . . . 15064559) complement | miR-142-as |

TABLE 7 miRNAs cognate to promoters/enhancers

| name of miRNA | Sequence of miRNA | SEQ ID NO: | Promoter/ enhancer |
|---|---|---|---|
| mir-196-2 | UAGGUAGUUUCAUGUUGUUGGG | 43 | HOXA9 |
| mir-196-2 | UAGGUAGUUUCAUGUUGUUGGG | 43 | HOXB7 |
| mir-22 | AAGCUGCCAGUUGAAGAACUGU | 44 | hypothetical protein MGC14376 |
| miR-95 (Mourelatos) | UUCAACGGGUAUUUAUUGAGCA | 45 | DNM1 |
| miR-95 (Mourelatos) | UUCAACGGGUAUUUAUUGAGCA | 45 | hypothetical protein FLJ20436 |
| hypothetical miRNA-168 | AGCCAGGUGCCUUCACCUGCU | 46 | hypothetical protein FLJ21827 |
| miR-191c | CAACGGAAUCCCAAAAGCAGCU | 47 | hypothetical protein FLJ10496 |
| mir-191c | CAACGGAAUCCCAAAAGCAGCU | 47 | nuclear protein E3-3 isoform a |
| miR-9 | UCUUUGGUUAUCUAGCUGUAUGA | 48 | CROC4 |
| hypothetical miRNA-156 | UGCUUUCCCUCCUUCCUUCUU | 29 | SPRY4 |
| hypothetical miRNA-156 | UGCUUUCCCUCCUUCCUUCUU | 29 | CD37 antigen |
| mir-219 | UGAUUGUCCAAACGCAAUUCU | 49 | RING1 |
| miR-142-as | UGUAGUGUUUCCUACUUUAUGG | 50 | BZRAP1 |

From these data, it can be observed that there are thirteen promoter/enhancer site-miRNA pairs in which the miRNA and a sequence within the 6-kb promoter/enhancer region upstream from the translational start site exhibit about 100% homology to each other; sites within 13 different promoter/enhancer regions exhibit homology to 9 microRNAs. Some 6-kb promoter/enhancer regions have multiple sites homologous to a particular miRNA. For example, sites homologous to mir-191c are found within promoters/enhancers of two different genes: one in the gene encoding hypothetical protein FLJ10496, and one in the gene DKFZP564J0123: nuclear protein E3-3 isoform a. Sites homologous to miR-95 (Mourelatos) are found within the promoter/enhancer regions of two different genes. Interestingly, sites homologous to mir-196-2 were found within the promoter/enhancer regions of two different genes in the family of genes encoding homeobox proteins, a family of transcription factors that orchestrates anterior-posterior pattern formation, determines segmental identity during embryogenesis, and contributes to lineage-specific proliferation and/or differentiation of hematopoietic progenitors; this suggests that mir-196-2 may have a role in regulation of homeotic genes and/or hematopoiesis.

Example 8

Bisulfite PCR 5-methylcytosine ($^m$C) is found mainly in symmetrical CpG/CpG dyads in double-stranded DNA, which are then transiently converted to hemimethylated sites at the time of DNA replication, but are then converted back to symmetrically methylated sites by a DNA methyltransferase with high specificity for hemimethylated sites. Hemimethylated sites are also transitional states in developmental processes; active demethylation or de novo methylation may sometimes be involved in gene reactivation or inactivation (Laird et al., Proc. Natl. Acad. Sci., 2004, 101, 204-9). Several methods are known in the art for determining the methylation status of CpG residues in DNA. Some examples of such methods are hairpin-bisulfite PCR (Laird et al., Proc. Natl. Acad. Sci., 2004, 101, 204-9), methylation sensitive restriction enzyme digestion, bisulfite sequencing, and restriction landmark genomic scanning (RLGS) (Kawai et al., Mol. Cell. Biol., 1994, 14, 7421-7; Smiraglia et al., Ann. NY Acad. Sci., 2003, 983, 110-9; and Matsuyama et al., Nucl. Acids Res., 2003, 31, 4490-6). Some of these methods include the use of methylation target microarrays (Weinmann et al., Genes Devel., 2002, 16, 235-44; and Chen et al., Am. J. Pathol., 2003, 163, 37-45).

In some embodiments, Methylation-specific PCR (MSP) was used to determine the presence or absence of methylated CpG residues within the DNA sequence of several of the promoters/enhancers described above. The MSP approach allows the determination of methylation patterns from very small samples of DNA, and can be used in to study abnormally methylated CpG islands in neoplastic tissue, in studies of imprinted genes, and in studies of human tumors for clonality by studying genes inactivated on the X chromosome by dosage compensation mechanisms. This method can also be used to observe the methylation status of genomic DNA at centromeres, telomeres, and origins of replication, as well as DNA in the promoters, enhancers, introns, exons, or other regions of genes regulated by small non-coding RNAs. Furthermore, bisulfite-PCR followed by restriction is a rapid and semi-quantitative method of analyzing DNA methylation. The PCR products are also suitable for either direct sequencing or cloning and sequencing.

The MSP method is based on the sequence differences between methylated alleles and unmethylated alleles which occur after sodium bisulfite treatment. A high frequency of CpG sites facilitates this method. Primers for a given locus are designed which distinguish methylated from unmethylated DNA in bisulfite-modified DNA. Because the distinction between methylated residues and unmethylated residues is built into the PCR amplification, extraordinary sensitivity, typically allowing the detection of 0.1% of alleles, can be achieved while maintaining specificity. Stringent conditions were maintained for amplification, and annealing temperatures were at the maximum temperature allowing annealing and subsequent amplification. Typically, amplifications were performed with an initial annealing temperature 5-8 degrees below the calculated melting temperature of the template-primer duplex, however slight (1-3° C.) increases or decreases in annealing temperature can by used to remedy non-specificity or lack of amplification product, respectively.

Using the MSP method, results are obtained immediately following PCR amplification and gel electrophoresis, without the need for further restriction or sequencing analysis. MSP also allows the analysis of very small samples, including paraffin-embedded and microdissected samples.

The DNA sequence in question is first modified by sodium bisulfite treatment converting unmethylated, but not methylated, cytosines to uracil. Following removal of bisulfite and completion of the chemical conversion, this modified DNA is used as a template for PCR. Two PCR reactions are performed for each DNA sample, one using primers specific for DNA originally methylated for the gene of interest, and one using primers specific for DNA originally unmethylated. PCR products (generally in the 80-200 bp range) are separated on 6-8% non-denaturing polyacrylamide gels, or, alternatively, on high-percentage (for example, 3%) horizontal agarose gels, and the bands are visualized by staining with ethidium bromide. The presence of a band of the appropriate molecular weight indicates the presence of unmethylated, and/or methylated alleles, in the original sample.

The most critical parameter affecting the specificity of methylation-specific PCR is primer design. Because the DNA modification by bisulfite deaminates cytosines to uracils, the two daughter strands of any given gene are no longer complementary after treatment. Either strand can serve as the template for subsequent PCR amplification, and the methylation pattern of each strand could then be determined. In practice, it is often easiest to deal with only one strand, most commonly the sense strand.

Primers were designed to amplify a region approximately 80-250 bp in length, and incorporated enough cytosines in the original sequence to assure that unmodified DNA would not serve as a template for the primers. In addition, the number and position of cytosines within the CpG dinucleotide determines the specificity of the primers for methylated or unmethylated templates. Where possible, one to three CpG dinucleotides were included in each primer, and concentrated nearest the 3' end of each primer, allowing optimal specificity of the primers while minimizing false positives due to mispriming. To facilitate simultaneous analysis of the unmethylated and methylated reactions of a given gene in the same thermocycler, the length of the primers was adjusted to give nearly equal melting/annealing temperatures, resulting in the unmethylated product being a few base pairs larger than the M product and conveniently providing a means of recognizing each lane in the gel after electrophoresis.

Primer Selection for Bisulfite-PCR:

The region of interest in the promoter/enhancer with the highest frequency of CpG dinucleotides is identified and its nucleotide sequence, written using A, G, C, and T symbols is saved as a document; this sequence is considered the "unconverted" sequence. The "methylated" sequence is generated by converting all C's to T's except those in CG dinucleotide pairs, using a word-processor or text-editor; this can be done by first converting all CG's to XG's, then converting all C's to T's, then converting all X's back to C's. The "unmethylated" sequence is generated by converting all C's to T's. If restriction analysis is to be performed, restriction enzyme sites unique to the methylated sequence (not in the unconverted or unmethylated sequence) can be used to further conform the methylation status of the region. Primers are chosen to hybridize to one or more CpG dinucleotides in the "methylated" sequence, preferably with the CpG residues in the 5'-end of the primer.

Eight gene promoters/enhancers which were found to bear sites homologous to microRNAs within 1-kb of the transcription start site as described above, were analyzed for design of CpG-specific PCR primer sets to be used in a methylation-specific PCR assay allowing the assessment of methylated versus unmethylated sequences (Herman et al., Proc. Natl. Acad. Sci., 1996, 93, 9821-6). For a subset of five of these promoters/enhancers, regions with high CpG density were chosen for the design of MSP primers. These primer sets are shown in Table 8. The column called "promoter/enhancer [expected product]" lists the name of the promoter/enhancer and the size in base pairs (bp) of the expected PCR product. The column called "Methylation state/primer strand" indicates the DNA strand that is primed by the given primer; for example, "uncoverted/sense" is the sequence of the sense strand in the promoter/enhancer of the genomic DNA untreated with bisulfite; "Methylated/sense" means that, in bisulfite-treated genomic DNA, the primer should be specific for methylated CpG residues and should only prime the amplification of the sense strand in the promoter/enhancer if the predicted CpGs were methylated, "Unmethylated/sense" means that, in bisulfite-treated genomic DNA, the primer should be specific for unmethylated CpG residues and should only prime the amplification of the sense strand in the promoter/enhancer if the predicted CpGs were unmethylated; "uncoverted/antisense" is the sequence of the antisense strand in the promoter/enhancer of the genomic DNA untreated with bisulfite; "Methylated/antisense" means that, in bisulfite-treated genomic DNA, the primer should be specific for methylated CpG residues and should only prime the amplification of the antisense strand in the promoter/enhancer if the predicted CpGs were methylated; "Unmethylated/antisense" means that, in bisulfite-treated genomic DNA, the primer should be specific for unmethylated CpG residues and should only prime the amplification of the antisense strand in the promoter/enhancer if the predicted CpGs were unmethylated.

NaOH and incubating at 37° C. for 10 minutes. 30 µl of 10 mM hydroquinone (Sigma), freshly prepared by adding 55 mg of hydroquinone to 50 ml of water, was added to each sample. 520 µl 3M Sodium bisulfite (Sigma S-8890) (freshly prepared by adding 1.88 grams of sodium bisulfite per 5 ml of H₂O, adjusting pH to 5.0 with NaOH) was then added, and sample was mixed thoroughly. Mineral oil was layered on top of each sample, and samples were incubated at 50° C. for 16 hours. Oil was then removed, and a DNA wizard miniprep kit (Promega A7280) was used to purify each sample according to the manufacturer's directions and adding 1 µl glycogen was as carrier (Boehringer).

Sequencing the bisulfite-PCR products can also be performed to further confirm the methylation status of the region. Bisulfite-PCR products can be cloned and sequenced using standard methods known in the art.

Genomic DNA was isolated from HeLa, A549, and T-24 cell lines. After bisulfite treatment of the genomic DNA, the methylation status of each of the five promoters/enhancers for which the MSP primers were designed was evaluated by the methylation-specific PCR method. In all three cell lines, methylation-specific PCR using the primer sets designed to amplify a 403-bp fragment from the DiGeorge syndrome critical region gene 8 (DGCR8) promoter/enhancer (bearing a site homologous to hypothetical miRNA-088) resulted in

TABLE 8

Methylation-specific primer sets

| promoter/enhancer [expected product] | Methylation state/ primer strand | Primer sequence | SEQ ID NO: |
|---|---|---|---|
| DiGeorge syndrome critical region gene 8 (DGCR8) [183 bp] | unconverted/sense | CGGCATGAAGACAGACTCGCTTAG | 51 |
| | Methylated/sense | CGGTATGAAGATAGATTCGTTAG | 52 |
| | Unmethylated/sense | TGGTATGAAGATAGATTTGTTTAGT | 53 |
| | unconverted/antisense | CATGCACAAGTCCGCTGAGACCCG | 54 |
| | Methylated/antisense | ACACAAATCCGCTAAAACCCG | 55 |
| | Unmethylated/antisense | CATACACAAATCCACTAAAACCCA | 56 |
| Hypothetical protein DKFZp761P1121 Chromosome 16 open reading frame 7 (C16orf7) [403 bp] | unconverted/sense | TTGCTGGGCGCTGTGGTTCACG | 57 |
| | Methylated/sense | GTTGGGCGTTGTGGTTTACG | 58 |
| | Unmethylated/sense | TTGTTGGGTGTTGTGGTTTATG | 59 |
| | unconverted/antisense | TCCCAGAACCTGCGAGTTACGTAT | 60 |
| | Methylated/antisense | TCCCAAAACCTACGAATTACGTA | 61 |
| | Unmethylated/antisense | TCCCAAAACCTACAAATTACATAT | 62 |
| zinc finger protein 358 (ZNF358) [222 bp] | unconverted/sense | ACGCCTGAAATGCGGCGCTCAGT | 63 |
| | Methylated/sense | ACGTTGAAATGCGGCGTTTAG | 64 |
| | Unmethylated/sense | ATGTTTGAAATGTGGTGTTTAGTT | 65 |
| | unconverted/antisense | TCCAAATCCTCCAAAACAAACTCC | 66 |
| | Methylated/antisense | CAAATCCTCCGAAACGAACTC | 67 |
| | Unmethylated/antisense | CAAATCCTCCAAAACAAACTCC | 68 |
| solute carrier family 12 (potassium/ chloride transporters) member 7 (SLC12A7) [254 bp] | unconverted/sense | CGATGGTCGGGAGCGCAGGCAG | 69 |
| | Methylated/sense | CGATGGTCGGGAGCGTAG | 70 |
| | Unmethylated/sense | TGATGGTTGGGAGTGTAGGTA | 71 |
| | unconverted/antisense | GCAGCCGACAGTCCCCGTCCCG | 72 |
| | Methylated/antisense | CCGACAATCCCCGTCCCG | 73 |
| | Unmethylated/antisense | ACAACCAACAATCCCCATCCCA | 74 |
| Hermansky-Pudlak syndrome-6 (HPS6) [185 bp] | unconverted/sense | CGGGCCACTGGGCGGCG | 75 |
| | Methylated/sense | CGGGTTATTGGGCGGCG | 76 |
| | Unmethylated/sense | GATTTTGGGTTATTGGGTGGTG | 77 |
| | unconverted/antisense | ACTCCGCCCCGCCCGGC | 78 |
| | Methylated/antisense | ACTCCGCCCCGCCCGACC | 79 |
| | Unmethylated/antisense | ACTCCACCCCACCCAACCAACT | 80 |

Bisulfite Treatment of DNA:

Genomic DNA (up to 2 µg) was diluted into 50 µl with distilled H₂O. DNA was denatured by adding 5.5 µl of 2M a prominent PCR product of the predicted size when the primers specific for the methylated CpG residues were used. Thus, the DiGeorge syndrome critical region gene 8

(DGCR8) promoter/enhancer is believed to be controlled by methylation, and its methylation state may be regulated by hypothetical miRNA-088.

Methylation-specific PCR using the primer sets designed to amplify a 403-bp fragment from the hypothetical protein DKFZp761P1121 (also known as Chromosome 16 open reading frame 7 (C16orf7)) promoter/enhancer, (bearing a site homologous to miR-185) resulted in a prominent PCR product of the predicted size when the primers specific for the methylated CpG residues were used on genomic DNA from A549 cells. In HeLa and T-24 cells, a more prominent PCR product resulted from the primers specific for unmethylated CpG residues. Thus, at least in A549 cells, the hypothetical protein DKFZp761P1121 promoter/enhancer is believed to be controlled by methylation, and its methylation state may be regulated by miR-185.

In all three cell lines, methylation-specific PCR using the primer sets designed to amplify a 222-bp fragment from the zinc finger protein 358 (ZNF358) promoter/enhancer (bearing a site homologous to hypothetical miRNA-156) resulted in a prominent PCR product of the predicted size when the primers specific for the methylated CpG residues were used. Thus, the zinc finger protein 358 (ZNF358) promoter/enhancer is believed to be controlled by methylation, and its methylation state may be regulated by hypothetical miRNA-156.

Methylation-specific PCR using the primer sets designed to amplify a 254-bp fragment from the solute carrier family 12 (potassium/chloride transporters) member 7 (SLC12A7) promoter/enhancer (bearing a site homologous to hypothetical miRNA-168) resulted in a prominent PCR product of the predicted size when the primers specific for the unmethylated CpG residues were used. Similarly, MSP using the primer sets designed to amplify a 185-bp fragment from the Hermansky-Pudlak syndrome-6 (HPS6) promoter/enhancer (bearing a site homologous to hypothetical miRNA-156) resulted in a prominent PCR product of the predicted size when the primers specific for the unmethylated CpG residues were used. Therefore, these preliminary experiments using MSP primers specific for sites within 1-kilobase regions from the promoters/enhancers of the SLC12A7 and HPS6 genes suggest that they are not down-regulated by CpG methylation.

Because sites within these promoter/enhancer regions exhibit homology to microRNAs, oligomeric compounds designed to target pri-miRNAs, pre-mRNAs or mature miRNAs can also be used to inhibit expression of these genes by altering the expression, levels or activity of the miRNA, ultimately affecting the ability of the mature miRNA to regulate the promoter/enhancer regions. The compounds can be analyzed for their effect on miRNA, pre-miRNA or pri-miRNA levels by quantitative real-time PCR as described above, or they can be analyzed for their effects on the expression of genes regulated by the promoters/enhancers exhibiting homology to the miRNA targeted by the compound. Uniform 2'-MOE oligomeric compounds targeting miRNAs which can be used to alter the activity of these homologous gene regulatory regions are shown in Table 9.

TABLE 9

Uniform 2'-MOE oligomeric compounds targeting pre-miRNAs and cognate to promoters/enhancers

| ISIS # | SEQ ID NO: | sequence | Oligomeric compound | Promoter/enhancer |
|---|---|---|---|---|
| 328105 | 81 | CCTCAATTATTGGAAATCACA | Targets hypothetical miRNA-088 | DiGeorge syndrome critical region gene 8 (DGCR8) |
| 341808 | 82 | GAACTGCCTTTCTCTCCA | Targets miR-185 | hypothetical protein DKFZp761P1121 (chromosome 16 ORF7) |
| 340356 | 83 | CTCAATAGACTGTGAGCTCCTT | Targets miR-28 (Tuschl) | Hypothetical protein FLJ11753 |
| 328120 | 84 | AAGAAGGAAGGAGGGAAAGCA | Targets hypothetical miRNA-156 | Zinc finger protein 358 (ZNF358) |
| 328124 | 85 | AGCAGGTGAAGGCACCTGGCT | Targets hypothetical miRNA-168 | Solute carrier family 12 (SLC12A7) (potassium/chloride transporters) |
| 328119 | 86 | AATAACACACATCCACTTTAA | Targets hypothetical miRNA-154 | Phosphodiesterase 4A, cAMP-specific (PDE4A) (phosphodies-terase E2 dunce homolog, Drosophila) |
| 328120 | 84 | AAGAAGGAAGGAGGGAAAGCA | Targets hypothetical miRNA-156 | Hermansky-Pudlak syndrome-6 (HPS6) |
| 342946 | 87 | TAGGAGAGAGAAAAAGACTGA | Targets miR-14 | Hypothetical protein FLJ22595 |

These oligomeric compounds targeting the miRNAs homologous to these promoter/enhancer regions were tested for their effects on promoter activity and gene expression.

According to methods described above, A549, HeLa, T-24 and HEK 293 cells were treated with the following oligomeric compounds targeting miRNAs: ISIS Number 328105; ISIS Number 328120 targets hypothetical miRNA-156; ISIS Number 328124; and ISIS Number 341808. The oligomeric compounds ISIS Numbers 328105, 328120, 328124 and 341808 are composed of 2'-methoxyethoxy (2'-MOE) nucleotides throughout and the internucleoside (backbone) linkages are phosphorothioate (P=S) throughout. All cytidine residues are 5-methylcytidines. Additionally, two oligomeric compounds targeting the pri-miRNA precursor of the mature hypothetical miRNA-088 microRNA, were tested: ISIS Number 338728 (GCTTTTAGAACCACTGC-CTC; herein incorporated as SEQ ID NO: 88) is a uniform 2'-MOE oligomeric compound, and ISIS Number 328646 (GCTTTTAGAACCACTGCCTC; herein incorporated as SEQ ID NO: 88) is a chimeric oligonucleotide ("gapmer"), 20 nucleotides in length, composed of a central "gap" region consisting of ten 2'-deoxynucleotides, which is flanked on both sides (5' and 3' directions) by five-nucleotide "wings," composed of 2'-methoxyethoxy (2'-MOE) nucleotides (a "5-10-5 2'-MOE gapmer"). The internucleoside (backbone) linkages are phosphorothioate (P=S) throughout the oligonucleotide. All cytidine residues are 5-methylcytidines. Also used in these studies was ISIS 341859 (CCTGGGGAGGGGACCATCAG; herein incorporated as SEQ ID NO: 89), a 5-10-52'-MOE gapmer oligomeric compound targeting miR-185.

Using the transfection methods described herein, these compounds were transfected at a concentration of 200 nM into A549 and HeLa cells, and after a 48 hour treatment with these oligomeric compounds, total DNA and RNA were harvested according to methods described above. Primer/probe sets for real-time RT-PCR were designed to detect the mRNA transcripts of the DiGeorge syndrome critical region gene 8 (DGCR8) and from the gene encoding hypothetical protein DKFZp761P1121 (Chromosome 16 open reading frame 7 (C16orf7). For RT-PCR of the DGCR8 mRNA, the sequence of the forward primer was ACAGCG-GTTTCTCTGGATGT (herein incorporated as SEQ ID NO: 90), the sequence of the reverse primer was CAGAACGCTGGACTCTTGCT (herein incorporated as SEQ ID NO: 91), and the sequence of the probe was GCGATGGAAATGTGTTCCTGCC (herein incorporated as SEQ ID NO: 92). For RT-PCR of the C16orf7 mRNA, the sequence of the forward primer was GGAGC-CATGGGATCTACTGA (herein incorporated as SEQ ID NO: 93), the sequence of the reverse primer was CTGAT-TCAGCCCCATTCTGT (herein incorporated as SEQ ID NO: 94), and the sequence of the probe was CCACTGTG-GTGTGCTCTCCAGC (herein incorporated as SEQ ID NO: 95). Real-time RT-PCR analysis was performed using these primer/probe sets specific for detection of the DGCR8 and C16orf7 mRNAs. It was predicted that oligomeric compounds targeting and inhibiting the function of the microRNAs homologous to the promoters/enhancers would alter the methylation state of the promoter/enhancer and thereby affect the expression of the mRNA message controlled by the corresponding promoter/enhancer.

Expression levels observed for each target were normalized to levels of expression of the c-raf mRNA, as described above. Inhibition of expression of the DGCR8 or C16orf7 mRNAs by the uniform 2'-MOE oligomeric compounds is expressed as a percentage of mRNA levels in untreated control cells (UTC): Results of these experiments are described in Tables 10 and 11 below.

TABLE 10

Effects of uniform 2'-MOE oligomeric compounds on DGCR8 mRNA expression

| ISIS Number | SEQ ID NO | Expression of DGCR8 mRNA (% UTC) A549 cells | Expression of DGCR8 mRNA (% UTC) HeLa cells |
|---|---|---|---|
| UTC | | 100 | 100 |
| 328105 | 81 | 371 | 271 |
| 328120 | 84 | 98 | 122 |
| 328124 | 85 | 79 | 114 |
| 338728 | 88 | 177 | 158 |
| 341808 | 82 | 99 | 102 |

TABLE 11

Effects of uniform 2'-MOE oligomeric compounds on C16orf7 mRNA expression

| ISIS Number | SEQ ID NO | Expression of C16orf7 mRNA (% UTC) A549 cells | Expression of C16orf7 mRNA (% UTC) HeLa cells |
|---|---|---|---|
| UTC | | 100 | 100 |
| 328105 | 81 | 94 | 91 |
| 328120 | 84 | 85 | 138 |
| 328124 | 85 | 120 | 117 |
| 338728 | 88 | 136 | 131 |
| 341808 | 82 | 94 | 103 |

From these data, it was observed that, in both A549 and HeLa cells, treatment with either of the oligomeric compounds ISIS Number 328105, targeting the mature hypothetical miRNA-088 or ISIS Number 338728, targeting the hypothetical miRNA-088 pre-miRNA precursor molecule, resulted in an increase in expression of the DGCR8 gene.

Additionally, using the transfection methods described herein, the uniform 2'-MOE oligomeric compounds and gapmer oligomeric compounds described above were transfected at a concentration of 200 nM into A549, T-24 and HEK 293 cells, and after a 48 hour treatment with these oligomeric compounds, total DNA and RNA were harvested according to methods described above. Real-time RT-PCR analysis was performed using the same primer/probe set specific for detection of the DGCR8 mRNA, and expression levels observed for the DGCR8 target were again normalized to levels of expression of the c-raf mRNA. Inhibition of expression of the DGCR8 mRNA by these oligomeric compounds is expressed as a percentage of mRNA levels in untreated control cells (UTC). Results of these experiments are described in Table 12 below.

TABLE 12

Effects of oligomeric compounds on DGCR8 mRNA expression

| ISIS Number | SEQ ID NO | (% UTC) A549 cells | (% UTC) T-24 cells | (% UTC) HEK 293 cells |
|---|---|---|---|---|
| UTC | | 100 | 100 | 100 |
| 328105 | 81 | 182 | 447 | 222 |
| 328646 | 88 | 95 | 223 | 118 |
| 338728 | 88 | 200 | 225 | 220 |
| 341808 | 82 | 133 | 93 | 116 |
| 341859 | 89 | 75 | 102 | 133 |

From these data, it was observed that, in A549, T-24 and HEK 293 cells, treatment with either of the uniform 2'-MOE oligomeric compounds, ISIS Number 328105, targeting the mature hypothetical miRNA-088 or ISIS Number 338728, targeting the hypothetical miRNA-088 pre-miRNA precursor molecule, resulted in an increase in expression of the DGCR8 gene. Furthermore, treatment of T-24 cells with the gapmer oligomeric compound, ISIS 328646, targeting the pri-miRNA precursor of the mature hypothetical miRNA-088 microRNA was also found to result in increased DGCR8 gene expression. Overall, the results from treatment of cells with oligomeric compounds of the present invention targeting hypothetical miRNA-088, which is homologous to the DGCR8 promoter/enhancer region, indicate that transcription of the DGCR8 mRNA is inhibited, supporting to the hypothesis that the hypothetical miRNA-088 small non-coding RNA plays a regulatory role at the homologous site in the DGCR8 promoter/enhancer. Taken with the results demonstrating that this promoter/enhancer region was methylated, it is believed that hypothetical miRNA-088 normally directs or is responsive to the methylation of the DGCR8 promoter/enhancer resulting in downregulation of expression of the DGCR8 mRNA, and that the oligomeric compound targeting the miRNA inhibits this methylation signal, leading to hypomethylation of the promoter/enhancer and, consequently, DGCR8 gene expression is no longer downregulated. The hypothetical miRNA-088 may itself guide methyltransferases to the DGCR8 promoter to direct methylation of the promoter, or, alternatively, the hypothetical miRNA-088 may bind to the methylated DNA site and recruit the binding of other factors which repress transcription from the DGCR8 promoter. In either case, an oligomeric compound targeting the hypothetical miRNA-088 appears to reverse the repression of DGCR8 gene expression.

Example 9

Microarray Expression Analyses

MicroRNAs (miRNAs) are reported to be involved in development and cell differentiation, yet, to date, little is known about the timing or patterns of their expression or the targets of their activity. A high-density oligonucleotide microarray was developed to examine the expression of miRNAs in multiple tissues from various organisms, including human, mouse and rat, as well as in multiple human cell lines.
miRNA Array Design:
In some embodiments, 5'-Amino-modified C6 oligonucleotides corresponding to human and/or mouse mature sense miRNA sequences were designed to hybridize to biotin end-labeled antisense miRNA targets. 5' amine modified C6 oligonucleotides were resuspended in 1× Micro Spotting Plus buffer (ArrayIt, Sunnyvale, Calif.) at a concentration of 20 µM, and each oligonucleotide probe was printed 4 times on a CodeLink-activated slides (GE health/Amersham Biosciences, Piscataway, N.J.) by a Pixsys7000 pin-based dispensing system (Genomics Solutions, Irvine, Calif.) in 2×2 pin and 40×8 spot configuration of each sub-array, with a spot diameter of 120 µm The printed slides were further processed according to the manufacturer's recommendations. The array also contains several 23-bp U6 and *Drosophila* tRNA oligonucleotides as positive controls for labeling and hybridization, and 23-bp random oligonucleotides are included as negative controls.
Sample RNA Preparation for miRNA Array:
For target preparation, total RNA from HeLa or T-24 cells was obtained from Ambion (Austin, Tex.). Total RNA from A549 cells was prepared by methods described supra. For each array, 20 µg of total RNA was mixed with 20 µl of random hexmer (75 ng/µl) (Invitrogen, Carlsbad, Calif.) to a final volume of 60 µl which was incubated at 70° C. for 10 minutes and then cooled to room temperature (RT). This mixture was used to reverse transcribe the first strand cDNA products using the SuperScript™ II Reverse Transcriptase Kit (Invitrogen, Carlsbad, Calif.) according to the manufacturer's directions with the following modifications: 24 µl of 5× first-strand buffer, 12 µl of 0.1 M DTT, 6 µl of 10 mM dNTP mix, 3 µl of SuperRase and 15 µl of SuperScript II RNaseH—reverse transcriptase (200 units/µl) were added to the RNA/primer mixture, and this mixture was incubated for 10 min. at RT, then 1 hour at 37° C., and another 1 hour at 42° C. in a water bath. After incubation, 40 µl of 1 N NaOH was added into the first-strand cDNA reaction mix and further incubated at 65° C. for another 30 minutes to denature the RNA/DNA hybrids. Finally, 40 µl of 1 N HCl was added to neutralize the reaction mix. cDNA was purified using the Qiaquick Nucleotide removal Kit (QIAgen, Valencia, Calif.) according to the manufacturer's directions. The Enzo® BioArray Terminal Labeling Kit with Biotin-ddUTP (Enzo Life sciences, Farmingdale, N.Y.) was used to label the 3'-termini of the first stand cDNA. 40 µl of 5× Reaction Buffer, 20 µl of 10× $CoCl_2$, 2 µl of 100× Biotin-ddUTP and 4 µl of 50× Terminal Deoxynucleotide Transferase were added to first strand cDNA at final volume of 200 µl and incubated at 37° C. for 1 hr. The reaction was terminated by adding 4 µL of 0.5 M EDTA, and the miRNA targets were ready for hybridization with the miRNA microarrays.
Target Hybridization and Detection:
Hybridization buffer consisted of 100 mM MES, 1 M [Na+], 20 mM EDTA, 0.01% Tween 20, 0.1 mg/ml Herring Sperm DNA and 0.5 mg/ml Acetylated BSA. Target hybridization was performed at 45° C. for 16 hours, and slides were washed 4 times (6 minutes each) in buffer A (6×SSPE, 0.01% Tween 20) at RT, and then washed twice with buffer B (100 mM MES, 0.1 M [Na+], 0.01% Tween 20) for 8 minutes at 45° C. Slides were then incubated for staining with Streptavidin solution mix (100 mM MES, 1 M [Na+], 0.05% Tween 20, 2 mg/ml BSA, 10 µg/ml R-Phycoerythrin streptavidin) (Invitrogen, Carlsbad, Calif.) at RT for 10 minutes followed by four washes with buffer A (6 minutes each) at 30° C. Second staining was carried out with antibody solutions (100 mM MES, 1 M [Na+], 0.05% Tween 20, 2 mg/ml BSA, 0.1 mg/ml goat IgG, 5 µg/ml biotin anti-streptavidin) at RT for 10 minutes followed by washing twice with buffer A for 4 minutes each wash. Third staining was performed with Streptavidin solution mix at RT for 10 minutes and slides were washed 4 times (6 minutes each) with wash buffer A at 30° C. Slides were then washed once for 5 minutes at RT with 0.2×SSC and then again for 5 minutes at RT with 0.1×SSC to remove excess salt and/or particulate matter from the slides.
Statistical Analysis:
Axon B4000 scanner and the GenePix Pro 4.0 software (Axon Instruments Union City, Calif.) were used to scan images. The median intensities of each feature and of the corresponding background were measured. The median intensity of the background was subtracted from the median intensity of the feature. Outliers detected by the ESD procedure (Rosner, 2000, *Fundamentals of Biostatistics*. Duxbury, N.Y.) were also removed at this stage. Resulting signal intensity values were normalized to per-chip median values. These signal intensity values were then used to obtain geometric means and standard errors for each miRNA. Each miRNA signal was transformed to log base 2 and 1-sample t-test was conducted. If the signal was significantly (p 0.05)

high or low compared to the chip median, then a Present (P) or Absent (A) call is assigned. A Marginal (M) call is given otherwise.

Data Clustering (K-Means):

Expression profiles of miRNAs in different human organs are clustered using the K-means clustering algorithm (Jain and Dubes, 1988). In this algorithm, observations are clustered as belonging to one of k groups. Initially, group centroids are randomly assigned. Group membership is then determined by calculating the centroid of each group and assigning each observation to the group with the closest centroid. The algorithm alternates between calculating the centroids based on the current group memberships, and reassigning observations to groups based on the new centroids. The above iterations stop when a pre-determined convergence limit is met.

Sensitivity and the Specificity of the miRNA Array:

The specificity and the sensitivity of this array-based approach was demonstrated using a small array designed to detect let-7 miRNA expression. This array consists of seven different let-7 probes to each of the closely related let-7 miRNAs. This array was used to detect a spiked sample of a let-7a miRNA transcript. Compared to the let 7a sequence, let-7e and let-7c each contain one mismatch, let-T7b and let-7d each contain two mismatches, and let-7f and let-7i contain multiple mismatches. When the let-7a transcript was spiked on the array, let-7f and let-7i probes gave a minimum detection in 1 pM biotin end-labeled spike concentrations. However, let-7b and let-7d, each carrying 2 miss matches to let -7a, produce signals in 1 pM concentrations but start to disappear at 0.1 pM. let-7a is clearly visible throughout a range of spike dilutions (1 pM to 0.1 fM). Thus, the ability to detect and distinguish miRNAs with perfect matches from those with single and multiple mismatches, even at low target concentrations, was demonstrated.

Validation of miRNA Array Data with Northern Blots:

To initially validate this method, the results obtained from the miRNA oligonucleotide array were compared to published expression levels of miRNAs from various tissues as determined by Northern blot analyses and quantification of signal using ImageQuant software and a calculated ratio of signal intensity:background (Sempere et al., Genome Biol., 2004, 5, R13). For the microarray results, if the ratio was >2.0, Present A) call was assigned. Absent (A) call was assigned if the ration was <1.1, and the Marginal (M) call was assigned if the ratio was between 2.0 and 1.1, inclusive. The sensitivity and the specificity of the Northern blot and miRNA array experimental results was calculated for P and A calls. Sensitivity is defined as the probability that the miRNA array yields a positive result, given positive data on the Northern blot. Specificity is defined as the probability that the miRNA array yields a negative result, given negative data on the Northern blot.

When the miRNA oligonucleotide array data from human heart and skeletal muscle tissues, was compared with the Northern blot data from the same tissues (Sempere et al., Genome Biol., 2004, 5, R13), and Fisher's exact test was applied to determine if there were nonrandom associations between categorical variables from the miRNA array and the Northern blot data (e.g. A, M, or P calls) the association between miRNA array and Northern blot data was found to be extremely significant (p<0.0001). In human heart, of 25 miRNAs assigned P by Northern blot analysis, 21 were also assigned P by miRNA array analysis, and of 47 miRNAs assigned A by Northern blot analysis, 33 were also assigned A by miRNA array analysis, indicating 84% sensitivity and 75% specificity. Similar analysis on human skeletal muscle expression levels resulted in 89% sensitivity and 83% specificity. Thus, a high concordance was found between miRNA array and Northern blot data.

Using this method of miRNA oligonucleotide array analysis, the expression of four miRNAs (hypothetical miRNA-088, hypothetical miRNA-156, hypothetical miRNA-168, and miR-185) found to be identical to sites in the DGCR8, ZNF358, SLC12A7, and C16orf7 gene promoters, respectively, was compared in A549, HeLa, and T-24 cell lines. The results are described in Table 13 below. In the column labeled "mean expression" is the value representing an average of normalized spot intensities where the mean=1 for the median intensity on the array.

TABLE 13

Array Comparison of miRNA expression in human cell lines

| | mean expression | | |
|---|---|---|---|
| miRNA | A549 cells | HeLa cells | T-24 cells |
| hypothetical miRNA-088 | 2.48 | 1.94 | 1.20 |
| hypothetical miRNA-156 | 0.35 | 3.17 | 2.41 |
| hypothetical miRNA-168 | 0.38 | 1.49 | 0.73 |
| miR-185 | 0.25 | 0.49 | 0.43 |

It was observed that hypothetical miRNA-088 appears to be expressed in A549 and HeLa cells; hypothetical miRNA-156 appears to be expressed in HeLa and T-24 cells; and hypothetical miRNA-168 appears to be expressed in HeLa cells.

Example 10

Oligomeric Compounds Designed to the Promoter/Enhancer of the DiGeorge Genetic Locus As described above, oligomeric compounds targeting or mimicking small non-coding RNAs can be used to treat cells and assess their effects on promoter/enhancer methylation status and upon expression of the gene controlled by the promoter/enhancer bearing the site homologous to a small non-coding RNA. A change in the methylation state upon treatment of cells with these oligomeric compounds targeting or mimicking a small non-coding RNA may be correlated with a change in expression of the gene. For example, as described herein, treatment of cells with an oligomeric compound targeting hypothetical miRNA-088 was observed to result in increased expression of the DGCR8 mRNA, and methylation-specific PCR using bisulfite-treated genomic DNA from cells treated with these oligomeric compounds may be performed to examine whether the methylation status of the DGCR8 promoter/enhancer region is also altered. Additional oligomeric compounds have been designed to assess their effects on the methylation status or transcriptional activities of these promoters. Uniform 2'-methoxyethoxy (2'-MOE) phosphorothioate oligomeric compounds were designed to target the miRNAs homologous to the promoter/enhancer sites, and are described in Table 14. The internucleoside (backbone) linkages are phosphorothioate (P=S) throughout. All cytidine residues are 5-methylcytidines.

TABLE 14

Uniform 2'-MOE oligomeric compounds targeting the miRNAs cognate to promoters/enhancers

| ISIS # | sequence | target | SEQ ID NO: |
|---|---|---|---|
| 371969 | CAATGCACTCAGCTTAAGTG | DiGeorge syndrome critical region gene 8 (DGCR8) | 96 |
| 371970 | GTCAAGCTGGCCACATTGCT | DiGeorge syndrome critical region gene 8 (DGCR8) | 97 |
| 371971 | GAAATCACAATGCACTCAGC | DiGeorge syndrome critical region gene 8 (DGCR8) | 98 |
| 371972 | CTGGCCACATTGCTCTTTTC | DiGeorge syndrome critical region gene 8 (DGCR8) | 99 |

Example 11

Regulation of E-Cadherin Gene Expression by Small Non-Coding RNA-Induced DNA-and/or Histone-Methylation In plants, dsRNAs targeted to CpG islands within a promoter have been demonstrated to induce RNA-directed DNA methylation. Until recently, it was unclear whether gene silencing mediated by DNA methylation could be induced by dsRNAs in mammalian cell. Several reports relating to studies of promoter methylation and RNA-induced transcriptional gene silencing have recently been published (Morris, et al., Science, 2004, 305, 1289-92; Kawasaki, et al., Nature, 2004, 431, 211-7; Kawasaki, et al., Nature, 2004, 431, 878) each of which is incorporated by reference in its entirety.

To determine whether oligomeric compounds of the present invention can affect DNA- and/or histone-methylation and transcriptional gene silencing in mammalian cells, oligomeric compounds can be used to target or mimic small non-coding RNAs bearing homology to regions within the promoter, enhancer, or other regulatory regions of a human gene known or believed to be regulated by DNA- and/or histone methylation. Because the E-cadherin tumor suppressor gene has been shown to be silenced by aberrant methylation of the promoter in several lines of tumor cells (Herman et al., Proc. Natl. Acad. Sci., 1996, 93, 9821-6; Graff, et al., J. Biol. Chem., 1997, 272, 22322-9; Corn, et al., Clin. Cancer Res., 2000, 6, 4243-8), this gene can serve as a model for studies of the effects of oligomeric compounds on the methylation status and transcriptional activity of the E-cadherin gene promoter.

In some embodiments, oligomeric compounds mimicking small non-coding RNAs can be targeted to CpG islands in the E-cadherin gene promoter region (approximately 1-kb upstream from the start site) (GenBank Accession L34545; herein incorporated as SEQ ID NO: 100). It is believed that these oligomeric compounds will be observed to induce DNA methylation and histone H3 Lys9 methylation. It is also expected that, as a consequence of this increased methylation, expression of the E-cadherin gene will be transcriptionally silenced. To further analyze the dependence of the oligomeric compound-mediated gene silencing on DNA methylation, additional oligomeric compounds targeting either or both of the DNMT1 or DNMT3B DNA methyltransferases may be used to disrupt DNA methylation of the E-cadherin promoter and reverse the methylation and transcriptional silencing induced by the oligomeric compounds mimicking small non-coding RNAs.

In some embodiments, oligomeric compounds targeting and inhibiting small non-coding RNAs bearing homology to regions within the promoter, enhancer, or other regulatory regions of the E-cadherin gene. As described above, upon treatment of cells with oligomeric compounds targeting hypothetical miRNA-088, a reduction in DNA methylation and an increase in DGCR8 gene expression was observed; thus, it is believed that oligomeric compounds targeting and inhibiting small non-coding RNAs homologous to regulatory regions of the E-cadherin gene will be observed to reduce DNA methylation. Similarly, these oligomeric compounds may result in a decrease in histone H3 Lys9 methylation within these regulatory regions. It is also expected that, as a consequence of the decrease in methylation upon treatment with oligomeric compounds targeting and inhibiting small non-coding RNAs homologous to regulatory regions of the E-cadherin gene, enhanced expression of the E-cadherin gene will be observed. Because the E-cadherin gene is a tumor suppressor gene, compounds able to increase its expression hold promise in the treatment of human cancers.

To assess whether oligomeric compounds of the present invention influence the methylation state of histones in the E-cadherin promoter, a chromatin immunoprecipitation assay (described in detail below) can also be performed.

As described above, in some embodiments, various oligomeric compounds can be synthesized, incorporating various chemically modified sugars and/or internucleoside linkages. For example, internucleoside linkages can be phosphodiester or phosphorothioate, and an oligomeric compound can be uniformly modified, where the chemical modification occurs at each nucleoside or internucleoside linkage, or can be a chimeric oligomeric compound containing two or more chemically distinct regions. For example, each nucleoside of the oligomeric compound could have a modified sugar selected from one of 4'-S, 2'-MOE, 2'-F, 2'-O-Methyl, LNA or ENA™ or could have uniformly modified internucleoside linkages such as uniform phosphorothioate internucleoside linkages. The nucleosides and or the internucleoside linkages may also have an alternating motif. The alternating motif can be the result of different sugar modifications that alternate (for example, 2'-ribose alternating with a 2'-modification other than ribose such as MOE, 2'-F or 2'-O-Methyl, or alternating fully modified sugars such as 2'-O-Methyl alternating with 2'-F), or can be the result of alternating internucleoside linkages (for example alternating phosphodiester and phosphorothioate internucleoside linkages). In some embodiments, oligomeric compounds can have an alternating pattern of 2'-F/2'-OMe sugar modification, while the internucleoside linkages are phosphorothioate throughout. In some embodiments, oligomeric compounds may include unmodified or natural nucleobases, such as adenine (A) and cytosine (C), or may include modified nucleobases, such as 5-methylcytosine (5-me-C), 5-hydroxymethyl cytosine, 3-methyladenine (3MeA), or 7-methylguanine (7MeG).

Thus, it is believed that oligomeric compounds mimicking or targeting small non-coding RNAs homologous to genomic regulatory regions of the E-cadherin gene will induce transcriptional gene silencing by means of DNAmethyltransferase-dependent methylation of DNA in human cells, and represent candidate pharmaceutical agents for the treatment of cancer.

Example 12

Chromatin Immunoprecipitation

Chromatin immunoprecipitation (ChIP) and acetylation assays are examples of methods known in the art for determining the presence of modifications on histones. Furthermore, methylated histones can be detected in Western Blot analyses using specific antibodies recognizing H3 K9 residues, and these antibodies can be used in CHIP assays for the assessment of whether histones in specific genomic DNA regions are methylated.

Furthermore, methods coupling chromatin immunoprecipitation to CpG island microarray analysis are also known in the art; a human CpG microarray was probed with immunoprecipitated chromatin using an antibody to a known transcription factor (Weinmann, et al., 2002, Genes Devel, 16:235-44).

Example 13

Diseases Associated with Small Non-Coding RNA Loci

Using the public databases Online Mendelian Inheritance in Man (OMIM) (accessible through the Internet at, for example, ftp.ncbi.nih.gov/repository/OMIM/) and LocusLink (accessible at, for example, ftp.ncbi.nlm.nih.gov/refseq/LocusLink/), a bioinformatic analysis was performed which allowed the prediction of small non-coding RNAs associated with several human diseases. First, small non-coding RNAs encoded within genes having LocusLink identification numbers were identified, and these were compared to tables (for example, "mim2loc," which connects LocusLink identification numbers with OMIM identification numbers, as well as "genemap", "genemap.key", "mim_title", and "morbidmap" tables) for the construction of a new database called "db1.mdb" linking small non-coding RNAs to LocusLink and OMIM identification numbers and linking these to human diseases.

It was observed that, beginning with 95 small non-coding RNA foldback precursors, a subset of 49 had OMIM identification numbers, 48 of which were linked to OMIM names. Six of these small non-coding RNAs were associated with specific diseased patients (some in each category were duplicates). Thus, the majority of small non-coding RNAs with OMIM identification numbers are not directly linked to observed diseases, but are likely to be important in pathways (such as cholesterol homeostasis) associated with diseases. Tables 15 and 16 summarize information retrieved from these studies.

TABLE 15

Small non-coding RNA genes associated with specific diseases

| OMIM ID: | Small non-coding RNA Name | Disease association |
|---|---|---|
| 120150 | collagen, type I, alpha 1/hypothetical miRNA-144 | Osteogenesis imperfecta, type I, 166200 |
| 114131 | calcitonin receptor containing hypothetical miRNA 30 | Osteoporosis, postmenopausal susceptibility, 166710 |
| 605317 | forkhead box P2/ hypothetical miRNA 169 | Speech-language disorder-1, 602081 |
| 600700 | LIM domain-containing preferred translocation partner in lipoma containing miR-28 | Lipoma; Leukemia, myeloid |
| 160710 | myosin, heavy polypeptide 6, cardiac muscle, alpha (cardiomyopathy, hypertrophic 1) containing miR__208 | Cardiomyopathy, familial hypertrophic, 192600 |
| 606157 | hypothetical protein FLJ11729 containing mir-103-2 | Neurodegeneration, pantothenate kinase-associated, 234200 |

This Table shows small non-coding RNAs associated with an OMIM record that was also associated with diseased patients.

The following table, Table 16, describes diseases or disease-related phenotypes found to be associated with genetic loci associated with a small non-coding RNA.

TABLE 16

Small non-coding RNAs associated with disease phenotypes

| OMIM ID: | Small non-coding RNA Name | Disease association |
|---|---|---|
| 114131 | calcitonin receptor containing hypothetical miRNA-30 | Osteoporosis, postmenopausal, susceptibility, 166710 |
| 120150 | collagen, type I, alpha 1/hypothetical miRNA-144 | Osteogenesis imperfecta, type I, 166200 |
| 138247 | glutamate receptor, ionotropic, AMPA 2/ hypothetical miRNA-171 | cerebellar long-term depression |

TABLE 16-continued

Small non-coding RNAs associated with disease phenotypes

| OMIM ID: | Small non-coding RNA Name | Disease association |
|---|---|---|
| 160710 | myosin, heavy polypeptide 6, cardiac muscle, alpha (cardiomyopathy, hypertrophic 1) containing miR-208 | Cardiomyopathy, familial hypertrophic, 192600 |
| 184756 | sterol regulatory element-binding protein-1/mir-33b | Emery-Dreifuss muscular dystrophy, 310300; dilated cardiomyopathy (CMD1A), 115200; familial partial lipodystrophy (FPLD), 151660 |
| 300093 | gamma-aminobutyric acid (GABA) A receptor, epsilon | early-onset parkinsonism, or Waisman syndrome, 311510; and MRX3 X-linked mental retardation, 309541 |
| 305660 | gamma-aminobutyric acid (GABA) A receptor, alpha 3 containing miR-105 (Mourelatos) and miR-105-2 | manic depressive illness, colorblindness, and G6PD |
| 305915 | glutamate receptor, ionotrophic, AMPA 3/hypothetical miRNA-033 | complex bipolar disorder; drug addiction |
| 600150 | potassium large conductance calcium-activated channel, subfamily M, alpha member 1 containing hypothetical miRNA-172 | cardiovascular disease |
| 600395 | glypican 1 containing miR-149 | angiogenesis |
| 600481 | Sterol regulatory element binding transcription factor 2 containing mir-33a | LDL and cholesterol homeostasis |
| 600592 | Minichromosome maintenance deficient (*S. cerevisiae*) 7 containing miR-93 (Mourelatos) and miR-25 and miR-94 | increased chromosomal loss, DNA replication and recombination |
| 600700 | LIM domain-containing preferred translocation partner in lipoma containing miR-28 | Lipoma; Leukemia, myeloid |
| 600758 | Focal adhesion kinase, p125/mir-151 | oncogenesis |
| 601009 | tight junction protein 1 (zona occludens 1)/hypothetical miRNA-183 | peptic ulcer disease and gastric carcinoma |
| 601029 | mesoderm specific transcript (mouse) homolog containing mir-240* (Kosik) | intrauterine and postnatal growth retardation |
| 601698 | protein tyrosine phosphatase, receptor type, N polypeptide 2 containing mir-153-2 | insulin-dependent diabetes mellitus (IDDM) |
| 601773 | protein tyrosine phosphatase, receptor type, N containing mir-153-1 | insulin-dependent diabetes mellitus (IDDM), 222100 |
| 603576 | melastatin 1 containing mir-211 | metastatic human melanoma |
| 603634 | ribosomal protein L5/hypothetical miRNA 168-2 | colorectal cancers |
| 603745 | slit (*Drosophila*) homolog 3 containing mir-218-2 | congenital diaphragmatic hernia |
| 603746 | slit (*Drosophila*) homolog 2 containing mir-218-1 | retinal ganglion cell axon guidance |
| 603803 | dachshund (*Drosophila*) homolog containing hypothetical miRNA-083 | cell proliferation during mammalian retinogenesis and pituitary development |
| 605317 | forkhead box P2/hypothetical miRNA 169 | autism & speech-language disorder-1, 602081 |
| 605547 | follistatin-like 1 containing mir-198 | systemic rheumatic diseases |
| 605575 | SMC4 (structural maintenance of chromosomes 4, yeast)-like 1 containing mir-16-3 and mir-15b | cell proliferation |
| 605766 | deleted in lymphocytic leukemia, 2 containing mir-16-1 and mir-15a-1 | B-cell chronic lymphocytic leukemia |
| 606157 | hypothetical protein FLJ11729 containing mir-103-2 | Neurodegeneration, pantothenate kinase-associated, 234200 (3); |
| 606160 | pantothenate kinase containing mir-107 | pantothenate kinase-associated neurodegeneration |
| 606161 | hypothetical protein FLJ12899 containing mir-103-1 | pantothenate kinase-associated neurodegeneration |

From these data, it was observed that several small non-coding RNAs are predicted to be associated with human disease states.

Example 14

Small Non-Coding RNAs within Introns or Exons

By mapping the coding sequences of small non-coding RNAs onto genomic contigs (which sequence information is available from public databases, such as GenBank and Locus Link), and identifying loci at which other reported gene coding sequences also co-map, it was observed that small noncoding RNAs can be encoded within the exons or introns of other genes. The oligomeric compounds of the present invention can be designed to target introns and exons of these genes. For example, the oligomeric compounds of the present invention can be designed to target introns or exons of the genes listed in Table 17; examples of such compounds are shown in Table 18. Alternatively, these oligomeric compounds can be designed to mimic the small non-coding RNAs encoded within the exons or introns of these genes listed in Table 17; compounds that mimic the small non-coding RNAs are designed, for example, to have identity with the small non-coding RNA.

TABLE 17

Small non-coding RNAs found within introns or exons of other genes

| Name of genetic locus including small RNA | Sequence of gene locus | SEQ ID NO: |
| --- | --- | --- |
| collagen, type I, alpha 1/hypothetical miRNA-144 | AGCAGACGGGAGTTTCTCCTCGGGGTCGGAGCAGG AGGCACGCGGAGTGTGAGGCCACGCATGAGCGGA CGCTAACCCCCTCCCCAGCCACAAAGAGTCTACAT GTCTAGGGTCTAGACATGTTCAGCTTTGTGGACCTC CGGCTCCTGCTCCTCTTAGCGGCCACCGCCCTCCTG ACGCACGGCCAAGAGGAAGGCCAAGTCGAGGGCC AAGACGAAGACATCCCACCAATCACCTGCGTACAG AACGGCCTCA | 101 |
| Ubiquitin protein ligase WWP2 containing mir-140 | GAATTCGCGGCCGCGTCGACCGCTTCTGTGGCCAC GGCAGATGAAACAGAAAGGCTAAAGAGGGCTGGA GTCAGGGGACTTCTCTTCCACCAGCTTCACGGTGAT GATATGGCATCTGCCAGCTCTAGCCGGGCAGGAGT GGCCCTGCCTTTTGAGAAGTCTCAGCTCACTTTGAA AGTGGTGTCCGCAAAGCCCAAGGTGCATAATCGTC AACCTCGAATTAACTCCTACGTGGAGGTGGCGGTG GATGGACTC | 102 |
| protein tyrosine phosphatase, receptor type, N polypeptide 2 containing mir-153-2 | CAGGCGGCGGGGATGGGGCCGCCGCTCCCGCTGCT GCTGCTGCTACTGCTGCTGCTGCCGCCACGCGTCCT GCCTGCCGCCCCTTCGTCCGTCCCCCGCGGCCGGCA GCTCCCGGGGCGTCTGGGCTGCCTGCTCGAGGAGG GCCTCTGCGGAGCGTCCGAGGCCTGTGTGAACGAT GGAGTGTTTGGAAGGTGCCAGAAGGTTCCGGCAAT GGACTTTTACCGCTACGAGGTGTCGCCCGTGGCCCT GCAGCGC | 103 |
| protein tyrosine phosphatase, receptor type, N containing mir-153-1 | CAGCCCCTCTGGCAGGCTCCCGCCAGCGTCGCTGC GGCTCCGGCCCGGGAGCGAGCGCCCGGAGCTCGGA AAGATGCGGCGCCCGCGGCGGCCTGGGGGTCTCGG GGGATCCGGGGGTCTCCGGCTGCTCCTCTGCCTCCT GCTGCTGAGCAGCCGCCCGGGGGGCTGCAGCGCCG TTAGTGCCCACGGCTGTCTATTTGACCGCAGGCTCT GCTCTCACCTGGAAGTCTGTATTCAGGATGGCTTGT TTGGGCA | 104 |
| Apoptosis-associated tyrosine kinase containing mir-244* (Kosik) | CTCCAGACCTACCCAGAAAGATGCCCGGATGGATC CTGCAGCTCCGTGGTTTTCTGGGAAGCAGCGGCC CCTGCTCTCAAGAGACCCTGGCTCCTGATGGTGGC CCCAAGGTTGCCAGCTGGTGCTAGGGACTCAGGAC AGTTTCCCAGAAAAGGCCAAGCGGGCAGCCCCTCC AGGGGCCGGGTGAGGAAGCTGGGGGGTGCGGAGG CCACACTGGGTCCCTGAACCCCCTGCTTGGTTACAG TGCAGCTCCT | 105 |
| sterol regulatory element-binding protein-1/mir-33b | TAACGAGGAACTTTTCGCCGGCGCCGGGCCGCCTC TGAGGCCAGGGCAGGACACGAACGCGCGGAGCGG CGGCGGCGACTGAGAGCCGGGGCCGCGGCGGCGC TCCCTAGGAAGGGCCGTACGAGGCGGCGGGCCCGG CGGGCCTCCCGGAGGAGGCGGCTGCGCCATGGACG AGCCACCCTTCAGCGAGGCGGCTTTGGAGCAGGCG CTGGGCGAGCCGTGCGATCTGGACGCGGCGCTGCT GACCGACATCGA | 106 |
| Transcriptional activator of the c-fos promoter containing mir-131-1/miR-9 | CTCCTCACAGAAGCCTGGAGCTGGGCATCCAAGAA GAAGCAGCCTCATTTGTTTTCTGGTGTCATCGTAGG TGGCCACCTATGGCTTTTGGGAATGTAAAAAGGGC AGCTCTCTGGCATGTTCCTGACTGAGGATCTCATAA CATTTAACTTGAGGAACTTCCTCCTTTTCCAGCTTT GGGAGTCAAGCTTCTCACCTGGGGCGGGTGGGTTC TGCACCACCCTCCCACCCTCCTTCCTCCGTGTGGAC GATAGA | 107 |
| Nuclear transcription factor Y, gamma containing miR-30c_2 and miR-30e | ACGCGTCCGGGGAAACGGTGCAAACGGCGTGGCC GCCATCTTGCTTGTGCCCCCGCTTCGCGCGCGCTCC GTGACGCACACTTCCCCCCTCCCCTCCGCCGCGCCT GGGCCTCTGCATTGCCCGACTCCGTAGGAGCGCGG GGGCGGCTCCTGCTCTTCCTGGACTCCTGAGCAGA |  108 |

TABLE 17-continued

Small non-coding RNAs found within introns or exons of other genes

| Name of genetic locus including small RNA | Sequence of gene locus | SEQ ID NO: |
|---|---|---|
| | GTTGTCGAGATGTCCACAGAAGGAGGATTTGGTGG TACTAGCAGCAGTGATGCCCAGCAAAGTCTACAGT CGTTCTGGC | |
| Sterol regulatory element binding transcription factor 2 containing mir-33a | CCGTCGGTGAGGCGGTGCCGGGCGGGGGTTGTCGG GTGTCATGGGCGGTGGCGACGGCACCGCCCCGCG TCTCCCTGAGCGGGACGGCAGGGGGGGCTTCTGCG CTGAGCCGGGCGATGGACGACAGCGGGGAGCTGG GTGGTCTGGAGACCATGGAGACCCTCACGGAGCTG GGCGACGAGCTGACCCTGGGAGACATCGACGAGAT GCTGCAATTTGTCAGTAATCAAGTGGGAGAGTTCC CTGACTTGTTT | 109 |
| Notch 4 like containing mir-123/mir-126 | CCGCCTGGAGGCACAGGCCATGAGGGGCTCTCAGG AGGTGCTGCTGATGTGGCTTCTGGTGTTGGCAGTG GGCGGCACAGAGCACGCCTACCGGCCCGGCCGTAG GGTGTGTGCTGTCCGGGCTCACGGGGATCCTGTCTC CGAGTCGTTCGTGCAGCGTGTGTACCAGCCCTTCCT CACCACCTGCGACGGGCACCGGGCCTGCAGCACCT ACCGAACCATCTATAGGACCGCCTACCGCCGCAGC CCTGGGCT | 110 |
| Minichromosome maintenance deficient (S. cerevisiae) 7 containing miR-93 (Mourelatos) and miR-25 and miR_94 | GACGTTTCGCGCCAATTTCGGTTGGCCGGCCACAG TCCACCGCGCGGAGATTCTCAGCTTCCCCAGGAGC AAGACCTCTGAGCCCGCCAAGCGCGGCCGCACGGC CCTCGGCAGCGATGGCACTGAAGGACTACGCGCTA GAGAAGGAAAAGGTTAAGAAGTTCTTACAAGAGTT CTACCAGGATGATGAACTGGGGAAGAAGCAGTTCA AGTATGGGAACCAGTTGGTTCGGCTGGCTCATCGG GAACAGGTGG | 111 |
| phosphodiesterase 2A, cGMP-stimulated containing miR_139 | CAGCAGAGCTGGATTGGGGTGTTGAGTCCAGGCTG AGTAGGGGGCAGCCCACTGCTCTTGGTCCCTGTGC CTGCTGGGGGTGCCCTGCCCTGAACTCCAGGCAGC GGGGACAGGGCGAGGTGCCACCTTAGTCTGGCTGG GGAGGCGGACGATGAGGAGTGATGGGGCAGGCAT GCGGCCACTCCATCCTCTGCAGGAGCCAGCAGTAC CCGGCAGCGCGACCGGCTGAGCCGCGGGGCCAGC AGGTCTTCCTCA | 112 |
| slit (Drosophila) homolog 3 containing mir-218-2 | CAACAGCATCAGCATGCTGACCAATTACACCTTCA GTAACATGTCTCACCTCTCCACTCTGATCCTGAGCT ACAACCGGCTGAGGTGCATCCCCGTCCACGCCTTC AACGGGCTGCGGTCCCTGCGAGTGCTAACCCTCCA TGGCAATGACATTTCCAGCGTTCCTGAAGGCTCCTT CAACGACCTCACATCTCTTTCCCATCTGGCGCTGGG AACCAACCCACTCCACTGTGACTGCAGTCTTCGGT GGCTGTC | 113 |
| glypican 1 containing miR-149 | GGCTGCCCGAGCGAGCGTTCGGACCTCGCACCCCG CGCGCCCCGCGCCGCCGCCGCCGCCGGCTTTTGTTG TCTCCGCCTCCTCGGCCGCCGCCGCCTCTGGACCGC GAGCCGCGCGCGCCGGGACCTTGGCTCTGCCCTTC GCGGGCGGGAACTGCGCAGGACCCGGCCAGGATC CGAGAGAGGCGCGGGCGGGTGGCCGGGGCGCCG CCGGCCCCGCCATGGAGCTCCGGGCCCGAGGCTGG TGGCTGCTAT | 114 |
| COPZ2 for nonclathrin coat protein zeta-COP containing mir-152 | GGCGGCGAGCGGAATGCAGCGGCCCGAGGCCTGG CCACGTCCGCACCCGGGGAGGGGCCGCGGCGG CCCAGGCCGGGGCCCGGCGCCGCCTGCTCGAGCC GGGGAGCCCTCGGGGCTGCGGTTGCAGGAACCTTC CCTCTACACCATCAAGGCTGTTTTCATCCTAGATAA TGACGGGCGCCGGCTGCTGGCCAAGTATTATGATG ACACATTCCCCTCCATGAAGGAGCAGATGGTTTTC GAGAAAAATGT | 115 |

TABLE 17-continued

Small non-coding RNAs found within introns or exons of other genes

| Name of genetic locus including small RNA | Sequence of gene locus | SEQ ID NO: |
|---|---|---|
| CGI-120 protein containing mir-148b | TTTTGCGGCTCCACGTCGGCACCAGCTGCGGGGCA AGATGGAGGCGCTGATTTTGGAACCTTCCCTGTAT ACTGTCAAAGCCATCCTGATTCTGGACAATGATGG AGATCGACTTTTTGCCAAGTACTATGACGACACCT ACCCCAGTGTCAAGGAGCAAAAGGCCTTTGAGAAG AACATTTTCAACAAGACCCATCGGACTGACAGTGA AATTGCCCTCTTGGAAGGCCTGACAGTGGTATACA AAAGCAGTAT | 116 |
| upstream regulatory element binding protein 1 containing mir-98 and let-7f-2 | ATGTTTAACCCTATGTATGCCTTGTTCCGTACCTCA CCTGGTGATCGAGTCACCTACACCATCAATCCATCT TCCCACTGCAACCCCAACCACCTCAGCTACTTCAA GTTTGTCGGACGCATTGTGGCCAAAGCTGTATATG ACAACCGTGTCTGGAGTGCTACTTTACTCGATCCT TTTACAAACACATCTTGGGCAAGTCAGTCAGATAT ACAGATATGGAGAGTGAAGATTACCACTTCTACCA AGGTCTG | 117 |
| zinc finger protein 265 containing miR_186 | ATGTCGACCAAGAATTTCCGAGTCAGTGACGGGGA CTGGATTTGCCCTGACAAAAAATGTGGAAATGTAA ACTTTGCTAGAAGAACCAGCTGTAATCGATGTGGT CGGGAGAAAACAACTGAGGCCAAGATGATGAAAG CTGGGGGCACTGAAATAGGAAAGACACTTGCAGA AAAGAGCCGAGGCCTATTTAGTGCTAATGACTGGC AATGTAAAACTTGCAGCAATGTGAATTGGGCCAGA AGATCAGAGTGT | 118 |
| calcitonin receptor containing hypothetical miRNA 30 | CAGAATTCCAGGACAAAGAGATCTTCAAAAATCAA AAATGAGGTTCACATTTACAAGCCGGTGCTTGGCA CTGTTTCTTCTTCTAAATCACCCAACCCCAATTCTT CCTGCCTTTTCAAATCAAACCTATCCAACAATAGA GCCCAAGCCATTTCTTTACGTCGTAGGACGAAAGA AGATGATGGATGCACAGTACAAATGCTATGACCGA ATGCAGCAGTTACCCGCATACCAAGGAGAAGGTCC ATATTGCAA | 119 |
| tight junction protein 1 (zona occludens 1)/ hypothetical miRNA-183 | TCCGGGTATGGATGTCAATCTTTTGTCTACAATGTG AATACATTTATCCTTCGGGGACCATCAAGACTTTCA GGAAAGGCCCCGCCTGTCTCTGCGCGGCCACTTTG CTGGGACAAAGGTCAACTGAAGAAGTGGGCAGGC CCGAGGCAGGAGAGATGCTGAGGAGTCCATGTGCA GGGGAGGGAAAGGGAGAGGCAGTCAGGGAGAGGA GGAGGAGGTACCGCCAGAAGGGGATCCTCCCGCTC CGAAAACCAG | 120 |
| melastatin 1 containing mir-211 | GGCTGAAAGAGCCTGAGCTGTGCCTCTCCATTCCA CTGGTGTGGCAGGGTCAGAAATCTTGGATAGAGAA AACCTTTTGCAAACGGGAATGTATCTTTGTAATTCC TAGCACGAAAGACTCTAACAGGTGTTGCTGTGGCC AGTTCACCAACCAGCATATCCCCCCTCTGCCAAGT GCAACACCCAGCAAAAATGAAGAGGAAAGCAAAC AGGTGGAGACTCAGCCTGAGAAATGGTCTGTTGCC AAGCACACCC | 121 |
| myosin, heavy polypeptide 6, cardiac muscle, alpha (cardiomyopathy, hypertrophic 1) containing miR_208 | GAGGCTGTTAATGCCAAATGCTCCTCACTGGAGAA GACCAAGCACCGCTACAGAATGAGATAGAGGAC TTGATGGTGGACGTAGAGCGCTCCAATGCTGCTGC TGCTGCTCTGGACAAGAAGCAGAGGAACTTTGACA AGATCCTGGCCGAGTGGAAGCAGAAGTATGAGGA GTCGCAGTCTGAGCTGGAGTCCTCACAGAAGGAGG CTCGCTCCCTCAGCACAGAGCTCTTCAAGCTCAAG AACGCCTACGAG | 122 |
| chloride channel 5 (nephrolithiasis 2, X-linked, Dent disease) containing miR_188 | TGATGTGATATGGCTGCAAGTGCCTTTGACCCTTTT GTGTCCCTTCCATAAACTGAAATACCTAAGCTGCTC CAACCTCCTTTTTGTCTTTTGTTTCATAAATCCTTTC CCATTGCACATCAACTCCTGTCTCTCTTTGTACTGT CACTCTCATCTGTTGCTTTCCATTCACACTGCCTTTA GCCACTCATCATTTTGTGCCTACACCACAGAAACCT CTGAATGTAATGGATGTTCCTACCAGAGGACAAGT CG | 123 |

TABLE 17-continued

Small non-coding RNAs found within introns or exons of other genes

| Name of genetic locus including small RNA | Sequence of gene locus | SEQ ID NO: |
|---|---|---|
| potassium large conductance calcium-activated channel, subfamily M, alpha member 1 containing hypothetical miRNA 172 | GGCGGCGGAGGCAGCAGTCTTAGAATGAGTAGCA ATATCCACGCGAACCATCTCAGCCTAGACGCGTCC TCCTCCTCCTCCTCCTCCTCTTCCTCTTCTTCTTCTTC CTCCTCCTCTTCCTCCTCGTCCTCGGTCCACGAGCC CAAGATGGATGCGCTCATCATCCCGGTGACCATGG AGGTGCCGTGCGACAGCCGGGGGCAACGCATGTGG TGGGCTTTCCTGGCCTCCTCCATGGTGACTTTCTTC GGGGGC | 124 |
| LIM domain-containing preferred translocation partner in lipoma containing miR-28 | GTCACTTTTATTTGGGGGTGTGGACAGCTGCTTTCC CAGGGGAGTACTTCTTACAGTGGGATTTCAAGACA AGATCGGCCTGAAGAAAAATTATATTTGTATATTTT TTAAAAAGTGGGAACTTTGAGGCTCAGAGACAGAG CAGAAGACAGAACCTGGTCTTCTGATTCCCTGTGTT CTGCTTTTTTCATTGTTCCACTGGACGCTCATCAGA GGGAAGATCTTTTTCCTCAATTGATTCCAACAATGT CTCAC | 125 |
| gamma-aminobutyric acid (GABA) A receptor, alpha 3 containing miR-105 (Mourelatos) and miR-105-2 | GAATTCCTTGTTTCAGTTCATTCATCCTTCTCTCCTT TCCGCTCAGACTGTAGAGCTCGGTCTCTCCAAGTTT GTGCCTAAGAAGATGATAATCACACAAACAAGTCA CTGTTACATGACCAGCCTTGGGATTCTTTTCCTGAT TAATATTCTCCCTGGAAGCACTGGTCAAGGGGAAT CAAGACGACAAGAACCCGGGGACTTTGTGAAGCA GGACATTGGCGGGCTGTCTCCTAAGCATGCCCCAG ATATTCC | 126 |
| gamma-aminobutyric acid (GABA) A receptor, epsilon, containing miR-224 (Sanger) | GCCAGAGCGTGAGCCGCGACCTCCGCGCAGGTGGT CGCGCCGGTCTCCGCGGAAATGTTGTCCAAAGTTC TTCCAGTCCTCCTAGGCATCTTATTGATCCTCCAGT CGAGGGTCGAGGGACCTCAGAGTGAATCAAAGAAT GAAGCCTCTTCCCGTGATGTTGTCTATGGCCCCCAG CCCCAGCCTCTGGAAAATCAGCTCCTCTCTGAGGA AACAAAGTCAACTGAGACTGAGACTGGGAGCAGA GTTGGCAAA | 127 |
| glutamate receptor, ionotropic, AMPA 2/ hypothetical miRNA 171 | AGGGATTCTTCTGCCTCCACTTCAGGTTTTAGCAGC TTGGTGCTAAATTGCTGTCTCAAAATGCAGAGGAT CTAATTTGCAGAGGAAAACAGCCAAAGAAGGAAG AGGAGGAAAAGGAAAAAAAAAGGGGTATATTGTG GATGCTCTACTTTTCTTGGAAATGCAAAAGATTATG CATATTTCTGTCCTCCTTTCTCCTGTTTTATGGGGAC TGATTTTTGGTGTCTCTTCTAACAGCATACAGATAG GGGGGCT | 128 |
| glutamate receptor, ionotrophic, AMPA 3/ hypothetical miRNA-033 | TGACGACTCCTGAGTTGCGCCCATGCTCTTGTCAGC TTCGTTTTAGGCGTAGCATGCCAGGCAGAAGAAA ATGGGGCAAAGCGTGCTCCGGGCGGTCTTCTTTTTA GTCCTGGGGCTTTTGGGTCATTCTCACGGAGGATTC CCCAACACCATCAGCATAGGTGGACTTTTCATGAG AAACACAGTGCAGGAGCACAGCGCTTTCCGCTTTG CCGTGCAGTTATACAACACCAACCAGAACACCACC GAGAAGC | 129 |
| deleted in lymphocytic leukemia, 2 containing mir-16-1 and mir-15a-1 | GATGCCTGATCTCATCAATCTAGCGGGAGAGACAG GATAACCTGTCCGAGAGTATAGCGCCACTTATGAC TCCGCCGGAAAAATTACTTTAAAAATCGCCAAAAA TTACTTGGAGCAAAGGGCAGTCCGGCGGCGTTCGC CAAGGTGGCGCAGTCGGTTTTGACCTGTAGCAGAG AACCAATTCTGGAGAACAGCCTCACTTCTTTGATTG AATACTTACATAATGCATTGGAACATGACATGAGA TTAAGGTTT | 130 |
| slit (Drosophila) homolog 2 containing mir-218-1 | CAGAGCAGGGTGGAGAGGGCGGTGGGAGGCGTGT GCCTGAGTGGGCTCTACTGCCTTGTTCCATATTATT TTGTGCACATTTTCCCTGGCACTCTGGGTTGCTAGC CCCGCCGGGCACTGGGCCTCAGACACTGCGCGGTT CCCTCGGAGCAGCAAGCTAAAGAAAGCCCCCAGTG CCGGCGAGGAAGGAGGCGGCGGGGAAAGATGCGC GGCGTTGGCTGGCAGATGCTGTCCCTGTCGCTGGG GTTAGTGCTG | 131 |

TABLE 17-continued

Small non-coding RNAs found within introns or exons of other genes

| Name of genetic locus including small RNA | Sequence of gene locus | SEQ ID NO: |
|---|---|---|
| conserved gene amplified in osteosarcoma containing miR-26a_2 | GTATGATGGCCAGCCACCGCTGAGAGCACGAAGCT GCTGCTGGCTGGCATTTTTCTCTAGCGTTGTGGTGC CACCTNCCCTTATNACCTTGGGACAAGAAGGGAAG GTGGCCATTGTCTTTCTCTTTGGAATCATAAAGTGG AACAGAGTCCCCAGAACTCATGTGGCCATTTCCGC CAGCATCACTCCCCGGTGCCTATGGGGTCCCGGTG TACCTAAAGGGAGAAGGACCCCATGTGCTAGCCAG AAATATAC | 132 |
| forkhead box P2/hypothetical miRNA 169 | ATGATGCAGGAATCTGCGACAGAGACAATAAGCA ACAGTTCAATGAATCAAAATGGAATGAGCACTCTA AGCAGCCAATTAGATGCTGGCAGCAGAGATGGAA GATCAAGTGGTGACACCAGCTCTGAAGTAAGCACA GTAGAACTGCTGCATCTGCAACAACAGCAGGCTCT CCAGGCAGCAAGACAACTTCTTTTACAGCAGCAAA CAAGTGGATTGAAATCTCCTAAGAGCAGTGATAAA CAGAGAGCACTG | 133 |
| nuclear LIM interactor-interacting factor containing mir-26b | CGCCTAGCCGCGCCGGTCCCAGAAGTGGCGAAAGC CGCAGCCGAGTCCAGGTCACGCCGAAGCCGTTGCC CTTTTAAGGGGGAGCCTTGAAACGGCGCCTGGGTT CCATGTTTGCATCCGCCTCGCGGGAAGGAAACTCC ATGTTGTAACAAAGTTTCCTCCGCGCCCCCTCCCTC CCCCTCCCCCCTAGAACCTGGCTCCCCTCCCCTCCG GAGCTCGCGGGGATCCCTCCCTCCCACCCCTCCCCT CCCCCCC | 134 |
| SMC4 (structural maintenance of chromosomes 4, yeast)-like 1 containing mir-16-3 and mir-15b | TTTTTATTTTTTCGAGTGAAGGACCCGGAGCCGAA ACACCGGTAGAGCGGGGAGGTGGGTACTACACAA CCGTCTGCAGCCTTGGTCTGAGTGGACTGTCCTGCA GCGACCATGCCCCGTAAAGGCACCCAGCCCTCCAC TGCCCGGCGCAGAGAGGAAGGGCCGCCGCCGCCGT CCCCTGACGGCGCCAGCAGCGACGCGGAGCCTGAG CCGCCGTCCGGCGGCACGGAGAGCCCAGCCACCGC CGCAGAGAC | 135 |
| sprouty (Drosophila) homolog 4 containing hypothetical miRNA 156 | GCGAGCTGAGCTGACAGCGCGGAGCTGGCGCTGTG GAGCGCAGGGAGCCTTGCCGGTTCCTCCGACCGGC GTCTGCGAGTACAGCGGCGGCTAACCTGCCCCGGC TTCAGGATTTACAGAGACGTGGGGCGATGCTTGTG ACCCTGCAGCTCCTCAAACCAGCCTGTATTGAGCG GTTTGCAGCCTGATGGTCAGCCCCCTCCCCACAGG GCCCCTAGAAGCCTGTTTCTGCGTACAGTCCAGGA CCTCCAGCCC | 136 |
| ribosomal protein L5/hypothetical miRNA 168_2 | GAGCAGCGGACGCCGGTCTCTGTTCCGCAGATGGG GTTTGTTAAAGTTGTTAAGAATAAGGCCTACTTTAA GAGATACCAAGTGAAATTTAGAAGACGACGAGAG GGTAAAACTGATTATTATGCTCGGAAACGCTTGGT GATACAAGATAAAAATAAATACAACACACCCAAAT ACAGGATGATAGTTCGTGTGACAAACAGAGATATC ATTTGTCAGATTGCTTATGCCCGTATAGAGGGGGA TATGATAGTC | 137 |
| heterogeneous nuclear ribonucleoprotein K containing mir-7-1 | AGGGCGCTCCAGGCGACACGATTGCAGACGCCATT ATCCTCTGTTTCTCTGCACCGACCTCGACGTCT TGCCTGTGTCCCACTTGTTCGCGGCCTATAGGCTAC TGCAGCACTGGGGTGTCAGTTGTTGGTCCGACCCA GAACGCTTCAGTTGTGCTCTGCAAGGATATATAAT AACTGATTGGTGTGCCCGTTTAATAAAAGAATATG GAAAGTGAACAGCCAGAAGAAACCTTCCCTAACAC TGAAACCA | 138 |
| follistatin-like 1 containing miR_198 | GGAGCTCCAACCTGCGCTTAGAGCTCGCTGCGGCC GTCCTGCCCCGTGCCCTCGGAGACCTGGACCGTAC CACGATGTGGAAACGCTGGCTCGCGCTCGCGCTAG CGCTGGTGGCGGTCGCCTGGGTCCGCGCCGAGGAA GAGCTAAGGAGCAAATCCAAGATCTGTGCCAATGT GTTTTGTGGAGCTGGCCGGGAATGTGCAGTCACAG AGAAAGGGGAACCCACCTGTCTCTGCATTGAGCAA TGCAAACCTC | 139 |

TABLE 17-continued

Small non-coding RNAs found within introns or exons of other genes

| Name of genetic locus including small RNA | Sequence of gene locus | SEQ ID NO: |
|---|---|---|
| chromosome 9 ORF3 containing mir-23b, mir-24-2 and mir-27b | CTCCAGGCACACGCAGCACACACAGCACATGCACC ACACGTAGCACACACACTGCATGCAGCACACACAC ACCAGAGGACGCACCCACACAGAGCACGCACAGCA CACACCACACAGCGCACGCACCCACACAGAGCACAC GCGGCACACACAGCACACACAGCGCACGCACCAC GCAGAGCACACACGGCACATGCAGCATACACACCA AACAGCGCATGCACCACACAGAGCACACGCGGCA CACGCAGCACACA | 140 |
| dachshund (Drosophila) homolog containing hypothetical miRNA 083 | GCGGCCGCGAGCAACGGCAGCGGCGGCGGCGGCG GCGGCATCAGCGGTGGCGGCGGCGTCGCTTCCAGC ACCCCCATCAACGCCAGCACCGGCAGCAGCAGCAG CAGCAGTAGCAGCAGCAGCAGCAGCAGCAGTAGT AGCAGCAGCAGCAGTAGCAGCAGCAGCTGCGGCC CCCTCCCCGGGAAACCCGTGTACTCAAGCGCGTCC CCAGTGGAAAACACCCCTCAGAATAATGAGTGCAA AATGGTGGATCTG | 141 |
| mesoderm specific transcript (mouse) homolog containing mir-240* (Kosik) | CGGCCAGCACACCCCGGCACCTCCTCTGCGGCAGC TGCGCCTCGCAAGCGCAGTGCCGCAGCGCACGCCG GAGTGGCTGTAGCTGCCTCGGCGCGGCTGCCGCCC TGCGCGGGCTGTGGGCTGCGGGCTGCGCCCCCGCT GCTGGCCAGCTCTGCACGGCTGCGGGGTCTGCGGC GCCCGGTGCTCTGCAACGCTGCGGCGGGCGGCATG GGATAACGCGGCCATGGTGCGCCGAGATCGCCTCC GCAGGATGAG | 142 |
| RNB6 containing mir-248* (Kosik) | GGCACGAGTGGGAGTACAGGACTCGCCTCCTCAGG GTTCCCTGTGCTGCCACTTTTCAGCCATGGCCACAA GTGAACAGAGTATCTGCCAAGCCCGGGCTTCCGTG ATGGTGTACGATGACACCAGTAAGAAATGGGTACC AATCAAACCTGGCCAGCAGGGATTCAGCCGGATCA ACATCTACCACAACACTGCCAGCAACACCTTCAGA GTCGTTGGAGTCAAGTTGCAGGATCAGCAGGTTGT GATCAATTA | 143 |
| chromosome 9 open reading frame 5 containing miR-32 | CGCCCCTCGGGGGCGGCTGTGGCGGAGGAACGATG GCCGACGGCGGCGGCCCTAAGGAGGCGCCAAGCCT GCGGAGCTCTCCCGGGCCGGCGCCGCGGGTCCCGC GCGCGGTCGGGCCGAGTGGCGGTGGCGGGGAGAC CCCGCGGACCGCGGCGCTGGCGCTGCGCTTCGACA AGCCCATTAAGCAGGCCTTCTACAACACCGGGGCC GTGCTGTTCGTGTGCCTGTGCTGCGGCGCCGCGGTG CTGGTCTACT | 144 |
| hypothetical protein FLJ21016, containing hypothetical miRNA 111 | CTACGTGCAAAAGCAGAATGGGAAGGCTAAGGGA CAGCTTCCCGATCTAAACTATTGGATAAACTTCAG ACCTATTTACCACCATCAGTGATGCTTCCCCCACGG CGTTTACAGACTCTCCTGCGGCAGGCGGTGGAACT ACAAAGGGATCGGTGCCTATATCACAATACCAAAC TTGATAATAATCTAGATTCTGTGTCTGTGCTTATAG ACCATGTTTGTAGTAGGAGGCAGTTCCCATGTTATA CGCAGCAG | 145 |
| R3H domain (binds single-stranded nucleic acids) containing containing mir-128a | TGCCGCTGGAGCCGGTGTCCGGGCTGGTGATGGGG TTAATTCCCTTTCGTAAGACTCTTACTTGCACCCAC CCAGCCCCGCCGTCGCCCCGCCGCGCCGCGCTCCA ACCGCCTCCTCCTCCTCAGTAACGCGGGCCACGGA AAGGTATGATATATTTGATCCAAGACAGTCCATTC CAGTCCGGGAATCTACAGTGGTGACAAGGACATGG GACTCCTCCTGCCAGATTACAGATGGTTCACTACA GTTGACATC | 146 |
| RNA cyclase homolog containing mir-101-3 | CTCAGCTACGCAGGTGCAACTTCTTGCGCCAACGT CTGGTCCTGTCTACCCTGAGCGGGCGCCCCGTCAA AATCCGAAAGATTCGGGCCAGAGACGACAACCCG GGCCTCCGAGATTTTGAAGCCAGCTTCATAAGGCT ATTGGACAAATAACGAATGGTTCTCGAATTGAAAT AAACCAAACAGGAACAACCTTATATTATCAGCCTG GCCTCCTGTATGGTGGATCTGTGGAACATGACTGT AGCGTCCTTCG | 147 |

TABLE 17-continued

Small non-coding RNAs found within introns or exons of other genes

| Name of genetic locus including small RNA | Sequence of gene locus | SEQ ID NO: |
|---|---|---|
| cyclic AMP-regulated phosphoprotein, 21 kD containing mir-128b | GTGATTTGCTGGAATTGTCATTAGTGTTGACGATGT GTCACACTGTGTAAGGGAATCGCATGGAGATGGGC ATTCCGAACTGTTAATGGGACATGGGACTCCAGT TGTCTCTGATCACTTGTGTGGATTTTCCTGGCGTAG AACGACAGAAGCCGCTAGTAAGTCGCCAAGACCTA CAGCAGGAATTCTGCACCAAAGGGCATAAAATCTT GTTATTTTAATTTGCATCTGGGAGAATGTCTGAGCA AGGAGAC | 148 |
| HYA22 protein containing miR-26a_1 | CCCCTCACCCCACTCAACTGCCCCGGGCCCCCGCG CGCGCGGCCGCCCCTCCACTCACCCTGTGTCGGCCC CGCTCCCCTCTCCCCCACCAGGCGAGCAGGCGAGC GGGCAGAGCCCGCGGCGGAGGTCGGCGCGGCTCC GGGGTTCATGGTGACGAGGCGGCGGCCGCTCGAGC CCAGCGGCGGCGGGCGGCGGGAGCTGGGGCGCGG GCCCGGGCCGCCTCTCCCAGAGCGCGGGGCCGGGC GGCGGGCGCGC | 149 |
| transient receptor potential cation channel, subfamily M, member 3 containing mir-204 | TAAATGAAAGCAACAGGAGCTGCTCCGGGGACTGC TTTTGCCAGCACCCAGAATCAGTGCTCAGGCTCAG AAATCCTGGATAGAAAGAGCATTTTATAAAAGAGA ATGTGTCCACATCATACCCAGCACCAAAGACCCCC ATAGGTGTTGCTGTGGGCGTCTGATAGGCCAGCAT GCTGGCCTCACCCCAGTATCTCCGTGCTTCAGAAT GAGAAAAATGAAAGTCGCCTCTCCCGAAATGACAT CCAGTCTGA | 150 |
| hypothetical protein FLJ11729 containing mir-103-2 | ATGCTGGGGAGGGCTGGCGGCCTCGACGGCAGC TGCGGAACTAGGCCGAGGGACAAAGGCTAAGTTTT TCCATGGTTTGGACTGGATATCGGTGGAAGTCTGGT CAAGCTGGTATATTTTGAACCCAAAGACATCACTG CTGAAGAAGAAGAGGAAGAAGTGGAAAGTCTTAA AAGCATTCGGAAGTACCTGACCTCCAATGTGGCTT ATGGGTCTACAGGCATTCGGGACGTGCACCTCGAG CTGAAGGACC | 151 |
| hypothetical protein FLJ12899 containing mir-103-1 | AGTGCGGCGGCGCCGCCTCTGCTCTCAGTGCCCCG GATCGGAGGCCGTCCATCGCCCCTCGGGCCGACGC CATGAAGATCAAAGATGCCAAGAAACCCTCTTTCC CATGGTTTGGCATGGACATTGGGGGAACTCTAGTA AAGCTCTCGTAGTTTGAACCTATTGATATCACAGCA GAGGAAGAGCAAGAAGAAGTTGAGAGTTTAAAAA GTATTCGGAAATATTTGACTTCTAACGTGGCATATG GATCCACCG | 152 |
| hypothetical protein FLJ13189 | ATGCGAGGCTGGGGCCGGTTGCCTACCGGCCGCTT CTCGCCGAGGCAGTCCAGACTTTTCCCCCGGCGGT GCCCGCTCCAAGACAGCATCTGTCAACGCTCCTCTT CTCCCCTCCTCCTCCTGCCGGGCCGGGCTCCGCCGG CTGCGGCCGAGAGGACGCGGGACCCGGCGCGGTG AGCCCATCAGCTGTCAGGCGAGCGGCGGCGAAGCGGCT GGAGGGCGGCGAGAGACACACAAAGAACGCGGTG GGCGGCGGCG | 153 |
| hypothetical protein FLJ20307 | ATGTATTGAAAGGGTATGTATAGGTGCAAATGATA AAAAAGAAGAGTTTGATGTTTCCGGAAATGGAAGG ATTGAAGGCCATATAGGTGTGCAATTACAAGAGCA TTCCTATCTTGAGAAGGGCATGCTGGCGTCTGAGG AACTGTCACAGTCTGGTGGTAGCACCAAAGATGAT GAATTAGCTTCAACCACTACTCCAAAGAGAGGGAG ACCTAAAGGTAACATCTCACGGACGTGTTCACACT GTGGCCTTTT | 154 |
| hypothetical protein HH114 containing hypothetical miRNA 154 | GGCACGAGGCTGGTCCCTGGCCCAACATGATACTG ACCAAAGCTCAGTACGACGAGATAGCCCAGTGCCT AGTGTCTGTGCCGCCTACCAGGCAGAGCCTGAGGA AGCTGAAGCAGAGGTTTCCCAGTCAATCGCAGGCC ACTCTGCTGAGCATCTTCTCCCAGGAGTACCAGAA ACACATTAAAAGAACACATGCCAAACATCATACTT CGGAAGCAATTGAAAGTTATTACCAGAGGTACCTG AATGGAGTGG | 155 |

TABLE 17-continued

Small non-coding RNAs found within introns or exons of other genes

| Name of genetic locus including small RNA | Sequence of gene locus | SEQ ID NO: |
|---|---|---|
| hypothetical protein MGC14376 containing mir-22 | GGCACGAGGTAGAGAAGCAGGGGATAGACTCATA GGCTGCAACAAAGGTGACTCTGTCCCTGGACACTG CCTCCGTACTTTCTCCTTGCTTCACTGGCCACAGCA TCTCCCTCCAGCCCTCGCTATGTGCCTCTGCCATCT TCACCCATCATGGAGCAGAGGTGAGGAGAGGCAG CCTGGGAATATGGAGACCAGTGAAGGACCAGGCCT GGAGAGCACAGGGTCCTACCTGGGCATCCAGCAGA GGAGCCCCTA | 156 |
| hypothetical protein PRO2730 containing let-7g | GGCTGGAAGGTTTAGCAGCAGCCTGGTGCAGTGCC CTGTCATCAAGACAAACCCACGGTCCTCCTGGGTG CCTACCAAGCTTGGTTTGTACAAAAGCAAGGTGGG AGTCTATTTTTGTACATGAGATACATCACACTTACC TGTGGGCCAGTATTGTGAAGTGAGTCTGAGTTGTTT ACACTGATGCCTTCCCTGCCCACCACAAATGTGTA CATAGTCTTCAGATGATACCACCCCTTTCCCCAGCT CCCAAC | 157 |
| talin 2 containing hypothetical miR-13/miR-190 | GGTTCCCAGGCACAGGAACCAATCCTGGTCTCAGC CAAGACCATGCTGGAGAGTTCATCGTACCTCATTC GCACTGCACGCTCTCTGGCCATCAACCCCAAAGAC CCACCCACCTGGTCTGTACTGGCTGGACATTCCCAT ACAGTGTCCGACTCCATCAAGAGTCTCATCACTTCT ATCAGGGACAAGGCCCCTGGACAGAGGGAGTGTG ATTACTCCATCGATGGCATCAACCGGTGCATCCGG GACATCGAG | 158 |
| myosin, heavy polypeptide 7B, cardiac muscle, beta containing hypothetical miRNA 039 | AGTTCATCCGCATTCACTTTGGTCCGTCTGGGAAGC TGGCATCCGCGGATATTGACAGCTATCTCCTGGAG AAGTCGCGGGTGATCTTCCAGTTGCCTGGTGAGCG CAGCTACCATGTCTACTACCAGATCCTCTCAGGGA GGAAGCCAGAGCTGCAGGACATGCTGCTTCTGTCT ATGAACCCCTATGACTACCACTTGTGCAGCCAGGG CGTCATCACCGTGGACAACATGAATGATGGGGAGG AGCTCATCG | 159 |
| KIAA1808 protein containing miR-95 (Mourelatos) | CGAGGTGCTGCGGGTGCAGGACAAGTACTTCCACA TCAAGTGCTTCGTCTGTAAAGCATGTGGCTGCGAC CTGGCCGAGGGCGGCTTCTTCGTGCGGCAGGGCGA GTACATCTGCACGCTGGACTACCAGAGGCTCTACG GCACCCGCTGCTTCAGCTGCGACCAGTTCATTGAG GGTGAGGTGGTGTCGGCGCTGGGCAAGACCTACCA CCCCGACTGCTTCGTGTGTGCCGTCTGCCGGCTGCC CTTCCCCCC | 160 |
| DiGeorge syndrome critical region gene 8/ hypothetical miRNA-088 | TCTCAGCGGACTTGTGCATGTTAGCTGTGTAGATTT ATGTGAGGGCTTGTAAAACTCTGGTCTTGTAAACT AGTCTTAAGCGCTTTTAATATGGAGACAGATGAGA GCCCCTCTCCGCTCCCGTGTGGGCCCGCAGGAGAA GCGGTGATGGAGAGCCGAGCTCGCCCCTTCCAAGC GCTGCCCCGTGAGCAGTCTCCACCACCTCCCCTGCA AACGTCCAGTGGTGCAGAGGTAATGGACGTTGGCT CTGGTGGT | 161 |
| hypothetical protein FLJ10496 containing miR_191 | CCTTCCGGTCACCATGGCGACCAGGCGCCTTGGGG TCGGGGAGACGCTGGGGGCCCTCAACGCGGCCCTG GGGCCAGGCGGTCCGGTGTGGACCAAGGAGACGC GCACCCGCCACCTGCGTTCCCGAGACTTTGTGGCAC CGCACCGCGCGCTGCAGGCGCGCTTCGATGACGGC CAGGTTCCGGAGCATTTGCTCCATGCCCTCGCCTGC CTGCAGGGCCCCGGTGTGGCCCCGGTGCTGGGCTG CGCGCCGAC | 162 |
| pantothenate kinase containing mir-107 | GCACAATCTAAAGCTTGTATATATAATGGTAGTTTG TAAAGTGTACCTTCCCCACAGGACGCTGTGGGATG TAAATTTGTAGGTCGAGTTTACAGCTGGTTTTTCTT GACTGAAGCTCATTCAACTGGTTACTTCTTTGTGGG TGTCTTTAATGAAGCTTATAAATGGCAAAAGCAA ACATTCCCATGGTTTGGCATGGACATCGGTGGAAC GCTGGTTAAATTGGTGTATTTCGAGCCGAAGGATA TTACAGC | 163 |

TABLE 17-continued

Small non-coding RNAs found within introns or exons of other genes

| Name of genetic locus including small RNA | Sequence of gene locus | SEQ ID NO: |
|---|---|---|
| LOC 114614/ hypothetical miRNA-071 | AGCGGAGCCCCGAGCCGCCCGCAGAGCAAGCGCG GGGAACCAAGGAGACGCTCCTGGCACTGCAGATAA CTTGTCTGCATTTCAAGAACAACCTACCAGAGACC TTACCTGTCACCTTGGCTCTCCCACCCAATGGAGAT GGCTCTAATGGTGGCACAAACCAGGAAGGGGAAA TCTGTGGTTTAAATTCTTTATGCCTCATCCTCTGAG TGCTGAAGGCTTGCTGTAGGCTGTATGCTGTTAATG CTAATCGTG | 164 |
| cezanne 2/hypothetical miRNA-180 | GTTCTCTCGCTCAGGTCTGTGCATGTAGTTGTCACT TGCAGCTCCATTTCCATCACGTGGTAAAATGCCCTT TCTCTTCTTTCCTGCAGATGGATGGTTTCTAGTGTG CTTCCAAACCCCACCTCGGCTGAGTGTTGGGCAGC ACTTCTACATGATCCTATGACTCTTGATATGGACGC AGTCCTGTCAGACTTTGTTCGGTCCACGGGGCAG AACCTGGTCTGGCCAGAGACCTGCTGGAGGCAAA AACTGG | 165 |
| hypothetical protein DKFZp761P1121, containing miR_185 | TCGGCGGCGGTGGCGGAGGCGACCTCGCGACCTGT GTCAGCAGAGCCGCCCTGCACCACCATGTGCATCA TCTTCTTTAAGTTTGATCCTCGCCCTGTTTCCAAAA ACGCGTACAGGCTCATCTTGGCAGCCAACAGGGAT GAATTCTACAGCCGACCCTCCAAGTTAGCTGACTTC TGGGGGAACAACAACGAGATCCTCAGTGGGCTGGA CATGGAGGAAGGCAAGGAAGGAGGCACATGGCTG GGCATCAGC | 166 |
| pituitary gland specific factor 1a containing mir-7-3 | ACCTGCATCTGCCAAGAAGACTGGAAGCAGGTGAG GCACAGAGAGGGGGAGGCCCGCAGCTGCGTGGGA GGAGGGGTGGTCTGAGGGACGTGGGATGCCGGGA ATGAGGCTGGTTTGCAGGTTGGCGCATGGACATTT TCCCAGAAAGGGACAGAGACGGCGAAGTTTGACG GTCTGGAAAGCAGAGACCAGCAGGGCTGACTGCTT GGGAGCACCAAATATCCGGACAGCGCCTCTCGGGA GGTCCGAGAAGAG | 167 |

TABLE 18

Uniform 2'-MOE oligomeric compounds targeting small non-coding RNAs found within introns or exons of other genes

| ISIS # | Sequence | Name of genetic locus including small RNA | SEQ ID NO. |
|---|---|---|---|
| 328117 | TCCACAAAGCTGAACATGTCT | collagen, type I, alpha 1/ hypothetical miRNA-144 | 168 |
| 327873 | CTACCATAGGGTAAAACCACT | Ubiquitin protein ligase WWP2 containing mir-140 | 169 |
| 327882 | TCACTTTTGTGACTATGCAA | protein tyrosine phosphatase, receptor type, N polypeptide 2 containing mir-153-2 | 170 |
| 327882 | TCACTTTTGTGACTATGCAA | protein tyrosine phosphatase, receptor type, N containing mir-153-1 | 170 |
| 344615 | CAATGCAACAGCAATGCAC | Apoptosis-associated tyrosine kinase containing mir-244* (Kosik) | 171 |
| 327968 | TCAACAAAATCACTGATGCTGGA | sterol regulatory element-binding protein-1/mir-33b | 172 |
| 327892 | ACTTTCGGTTATCTAGCTTTA | Transcriptional activator of the c-fos promoter containing mir-131-1/miR-9 | 173 |

TABLE 18-continued

Uniform 2'-MOE oligomeric compounds targeting small non-coding RNAs found within introns or exons of other genes

| ISIS # | Sequence | Name of genetic locus including small RNA | SEQ ID NO. |
|---|---|---|---|
| 348128 | CTTCCAGTCAAGGATGTTTACA | Nuclear transcription factor Y, gamma containing miR-30c_2 and miR-30e | 174 |
| 327908 | CAATGCAACTACAATGCAC | Sterol regulatory element binding transcription factor 2 containing mir-33a | 175 |
| 341798 | GCATTATTACTCACGGTACGA | Notch 4 like containing mir-123/mir-126 | 176 |
| 340348 | CTACCTGCACGAACAGCACTTT | Minichromosome maintenance deficient (*S. cerevisiae*) 7 containing miR-93 (Mourelatos) and miR-25 and miR_94 | 177 |
| 341813 | AGACACGTGCACTGTAGA | phosphodiesterase 2A, cGMP-stimulated containing miR_139 | 178 |
| 327915 | ACATGGTTAGATCAAGCACAA | slit (*Drosophila*) homolog 3 containing mir-218-2 | 179 |
| 341785 | GGAGTGAAGACACGGAGCCAGA | glypican 1 containing miR-149 | 180 |
| 327964 | CCAAGTTCTGTCATGCACTGA | COPZ2 for nonclathrin coat protein zeta-COP containing mir-152 | 181 |
| 327954 | ACAAAGTTCTGTGATGCACTGA | CGI-120 protein containing mir-148b | 182 |
| 327912 | AACTATACAATCTACTACCTCA | upstream regulatory element binding protein 1 containing mir-98 and let-7f-2 | 183 |
| 341800 | AAGCCCAAAAGGAGAATTCTTTG | zinc finger protein 265 containing miR_186 | 184 |
| 328091 | GCTGCCGTATATGTGATGTCA | calcitonin receptor containing hypothetical miRNA 30 | 185 |
| 328137 | GTAAGCGCAGCTCCACAGGCT | tight junction protein 1 (zona occludens 1)/hypothetical miRNA-183 | 186 |
| 327946 | AGGCGAAGGATGACAAAGGGAA | melastatin 1 containing mir-211 | 187 |
| 341812 | ACAAGCTTTTTGCTCGTCTTAT | myosin, heavy polypeptide 6, cardiac muscle, alpha (cardiomyopathy, hypertropbic 1) containing miR_208 | 188 |
| 341809 | ACCCTCCACCATGCAAGGGATG | chloride channel 5 (nephrolithiasis 2, X-linked, Dent disease) containing miR_188 | 189 |
| 328128 | AGTAACTTCTTGCAGTTGGA | potassium large conductance calcium-activated channel, subfamily M, alpha member 1 containing hypothetical miRNA 172 | 190 |
| 340356 | CTCAATAGACTGTGAGCTCCTT | LIM domain-containing preferred translocation partner in lipoma containing miR-28 | 83 |

TABLE 18-continued

Uniform 2'-MOE oligomeric compounds targeting small
non-coding RNAs found within introns or exons of other genes

| ISIS # Sequence | Name of genetic locus including small RNA | SEQ ID NO. |
|---|---|---|
| 340343 ACAGGAGTCTGAGCATTTGA | gamma-aminobutyric acid (GABA) A receptor, alpha 3 containing miR-105 (Mourelatos) and miR-105-2 | 191 |
| 346692 TAAACGGAACCACTAGTGACTTG | gamma-aminobutyric acid (GABA) A receptor, epsilon, containing miR-224 (Sanger) | 192 |
| 328127 AACGATAAAACATACTTGTCA | glutamate receptor, ionotropic, AMPA 2/hypothetical miRNA 171 | 193 |
| 328092 GGTAGGTGGAATACTATAACA | glutamate receptor, ionotrophic, AMPA 3/ hypothetical miRNA-033 | 194 |
| 327877 CGCCAATATTTACGTGCTGCTA | deleted in lymphocytic leukemia, 2 containing mir-16-1 and mir-15a-1 | 195 |
| 327915 ACATGGTTAGATCAAGCACAA | slit (Drosophila) homolog 2 containing mir-218-1 | 179 |
| 327907 AGCCTATCCTGGATTACTTGAA | conserved gene amplified in osteosarcoma containing miR-26a_2 | 196 |
| 328125 TATGAAATGCCAGAGCTGCCA | forkhead box P2/hypothetical miRNA 169 | 197 |
| 327963 AACCTATCCTGAATTACTTGAA | nuclear LIM interactor-interacting factor containing mir-26b | 198 |
| 327877 CGCCAATATTTACGTGCTGCTA | SMC4 (structural maintenance of chromosomes 4, yeast)-like 1 containing mir-16-3 and mir-15b | 195 |
| 328120 AAGAAGGAAGGAGGGAAAGCA | sprouty (Drosophila) homolog 4 containing hypothetical miRNA 156 | 84 |
| 328124 AGCAGGTGAAGGCACCTGGCT | ribosomal protein L5/ hypothetical miRNA 168_2 | 85 |
| 327879 AACAAAATCACTAGTCTTCCA | heterogeneous nuclear ribonucleoprotein K containing mir-7-1 | 196 |
| 341801 CCTATCTCCCCTCTGGACC | follistatin-like 1 containing miR_198 | 197 |
| 327883 CAGAACTTAGCCACTGTGAA | chromosome 9 ORF3 containing mir-23b, mir-24-2 and mir-27b | 198 |
| 328104 TATGATAGCTTCCCCATGTAA | dachshund (Drosophila) homolog containing hypothetical miRNA 083 | 199 |
| 344611 ACATTTTTCGTTATTGCTCTTGA | mesoderm specific transcript (mouse) homolog containing mir-240* (Kosik) | 200 |
| 344617 GACGGGTGCGATTTCTGTGTGAGA | RNB6 containing mir-248* (Kosik) | 201 |
| 340360 GCAACTTAGTAATGTGCAATA | chromosome 9 open reading frame 5 containing miR-32 | 202 |

TABLE 18-continued

Uniform 2'-MOE oligomeric compounds targeting small
non-coding RNAs found within introns or exons of other genes

| ISIS # Sequence | Name of genetic locus including small RNA | SEQ ID NO. |
|---|---|---|
| 328111 TCCGAGTCGGAGGAGGAGGAA | hypothetical protein FLJ21016, containing hypothetical miRNA 111 | 203 |
| 327881 AAAAGAGACCGGTTCACTGTGA | R3H domain (binds single-stranded nucleic acids) containing containing mir-128a | 204 |
| 327947 TCAGTTATCACAGTACTGTA | RNA cyclase homolog containing mir-101-3 | 205 |
| 327923 GAAAGAGACCGGTTCACTGTGA | cyclic AMP-regulated phosphoprotein, 21 kD containing mir-128b | 206 |
| 327907 AGCCTATCCTGGATTACTTGAA | HYA22 protein containing miR-26a_1 | 196 |
| 327932 AGGCATAGGATGACAAAGGGAA | transient receptor potential cation channel, subfamily M, member 3 containing mir-204 | 207 |
| 327906 TCATAGCCCTGTACAATGCTGCT | hypothetical protein FLJ11729 containing mir-103-2 | 208 |
| 327906 TCATAGCCCTGTACAATGCTGCT | hypothetical protein FLJ12899 containing mir-103-1 | 208 |
| 327874 GCTGCAAACATCCGACTGAAAG | hypothetical protein FLJ13189 | 209 |
| 328131 ATATGTCATATCAAACTCCTA | hypothetical protein FLJ20307 | 210 |
| 328119 AATAACACACATCCACTTTAA | hypothetical protein HH114 containing hypothetical miRNA 154 | 86 |
| 327896 ACAGTTCTTCAACTGGCAGCTT | hypothetical protein MGC14376 containing mir-22 | 211 |
| 327967 ACTGTACAAACTACTACCTCA | hypothetical protein PRO2730 containing let-7g | 212 |
| 328089 AGTGTAGGAATATGTTTGATA | talin 2 containing hypothetical miR-13/miR-190 | 213 |
| 328093 TAAACATCACTGCAAGTCTTA | myosin, heavy polypeptide 7B, cardiac muscle, beta containing hypothetical miRNA 039 | 214 |
| 340350 TGCTCAATAAATACCCGTTGAA | KIAA1808 protein containing miR-95 (Mourelatos) | 215 |
| 328105 CCTCAATTATTGGAAATCACA | DiGeorge syndrome critical region gene 8/hypothetical miRNA-088 | 81 |
| 341802 AGCTGCTTTTGGGATTCCGTTG | hypothetical protein FLJ10496 containing miR_191 | 216 |
| 327910 TGATAGCCCTGTACAATGCTGCT | pantothenate kinase containing mir-107 | 217 |
| 328101 AAACCCCTATCACGATTAGCA | LOC 114614/hypothetical miRNA-071 | 218 |
| 328135 ACCGAACAAAGTCTGACAGGA | cezanne 2/hypothetical miRNA-180 | 219 |

TABLE 18-continued

Uniform 2'-MOE oligomeric compounds targeting small
non-coding RNAs found within introns or exons of other genes

| ISIS # | Sequence | Name of genetic locus including small RNA | SEQ ID NO. |
|---|---|---|---|
| 341808 | GAACTGCCTTTCTCTCCA | hypothetical protein DKFZp761P1121, containing miR_185 | 82 |
| 327879 | AACAAAATCACTAGTCTTCCA | pituitary gland specific factor 1a containing mir-7-3 | 196 |

It was noted that the hypothetical protein FLJ21016, containing hypothetical miRNA 111, is also known as WD repeat domain 26, which is a WD40 repeat containing protein; the WD40 domain is found in a number of eukaryotic proteins with a wide variety of functions including adaptor/regulatory modules in signal transduction, pre-mRNA processing and cytoskeleton assembly. It was also observed that several of these genes containing miRNAs within their intron or exons are known to be involved in heterochromatin formation or function. For example, the Minichromosome maintenance deficient (S. cerevisiae) 7 (MCM7) gene, containing the miR-93 (Mourelatos), miR-25 and miR-94s, is a human homolog of a gene known to be involved in DNA replication at origins in the budding yeast. The SMC4 (structural maintenance of chromosomes 4, yeast)-like 1 (SMC4L1) gene, containing mir-16-3 and mir-15b, is a member of the SMC family of genes involved in mitotic chromosome condensation in frogs and DNA repair in mammals.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

Example 15

Evaluating Oligomeric Compounds for Effects on the Epigenetic Control of Gene Expression Oligomeric compounds which modulate the degradation or translational suppression of a target nucleic acid, such as siRNAs, are attractive as therapeutic agents for the treatment or amelioration of a wide variety of diseases, including cardiovascular diseases, metabolic diseases, and cancer. There are concerns in the field of siRNA therapeutics that these agents may induce specific or non-specific alterations in epigenetic control of gene expression. Thus, there is a need to ensure that any agents working through an RNA interference pathway that are developed for therapeutic applications do not cause undesired side effects through RNA associated silencing.

In one embodiment, the present invention provides methods of screening oligomeric compounds to ensure that candidate compounds for therapeutic applications do not cause undesired changes in epigenetic control of gene expression. Non-limiting examples of these oligomeric compounds can be antisense nucleic acids, oligomeric compounds which are cognate to or mimic MicroRNA, or siRNA. One example involves the use of siRNAs that target a nucleic acid molecule whose modulation would provide a therapeutic benefit, such siRNA are designed by methods well known in the art and selected for analysis to determine if such siRNA causes undesired changes in epigenetic control of gene expression. Heterochromatic regions that are subject to epigenetic regulation of gene expression and that are not subject to regulation by the target nucleic acid of interest are identified for analysis. Heterochromatic regions subject to epigenetic regulation of gene expression are well known in the art, examples of which are provided herein. Following the treatment of cultured cells or animals with the selected siRNAs, assays are performed to evaluate modifications to the identified heterochromatic regions. Such assays include methylation-specific PCR, to identify changes in methylation (methylation or demethylation) status at a genomic locus. Examples of heterochromatic regions that are subject to regulation by methylation are provided herein. Changes in acetylation status (acetylation or deacetylation) of heterochromatic regions can also be monitored, for example, through the use of acetylation assays known in the art; examples of heterochromatic regions that are subject to regulation by acetylation are provided herein. Other assays include chromatin immunoprecipitation experiments, to identify changes in the binding of a protein, protein complex or ribonucleoprotein complex (excess or insufficient binding) to a heterochromatic region. Examples of proteins, protein complexes and ribonucleoprotein complexes that bind to heterochromatic regions are provided herein. Additionally, modifications such as phosphorylation, dephosphorylation, ubiquitination, sumoylation or pseudouridylation can be evaluated.

Example 16

Evaluating the Effects of Oligomeric Compounds that Target or Mimic Small Non-Coding RNAs Provided herein are non-limiting examples of oligomeric compounds that are designed to target small non-coding RNAs which participate in the epigenetic control of gene expression. To evaluate the activity of such oligomeric compounds, screening assays are performed to measure changes in DNA methylation, histone modifications, and/or RNA-associated silencing. An initial step is the identification of a genomic locus cognate to a small non-coding RNA, and the design of an oligomeric compound that is cognate to, or that mimics, the small non-coding RNA. Methods of designing oligomeric compounds that target or mimic the small non-coding RNAs are well known in the art, examples of which are provided herein. Cultured cells are contacted with oligomeric compounds that target or mimic the small non-coding RNAS; methods of treating cells with oligomeric compounds are provided herein. Following the treatment of cultured cells with the selected oligomeric compounds, assays are performed to evaluate modifications to the identified heterochromatic regions. Such assays include methylation-specific PCR, to identify changes in methylation (methylation or demethylation) status at a genomic locus. Examples of heterochromatic regions that are subject to regulation by methylation are provided herein. Changes in acetylation status (acetylation or deacetylation) of heterochromatic regions can also be monitored, for example, through the use of acetylation assays known in the art; examples of heterochromatic regions that are subject to regulation by acetylation are provided herein. Other assays include chromatin immunoprecipitation experiments, to identify changes in the binding of a protein, protein complex or ribonucleoprotein complex (excess or insufficient binding) to a heterochromatic region. Examples of proteins, protein complexes and ribonucleoprotein complexes that bind to heterochromatic regions are provided herein. Additionally, modifications such as phosphorylation, dephosphorylation, ubiquitination, sumoylation and/or pseudouridylation can be evaluated. Changes in the epigenetic control of gene expression in the treated cells as compared to cells not contacted with the oligomeric compounds indicate that the oligomeric compound influences the epigenetic control of gene expression.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is specifically incorporated herein by reference in its entirety.

What is claimed is:

1. A method comprising:
    identifying an oligomeric compound which modulates degradation or translational suppression of a target nucleic acid molecule;
    identifying at least one heterochromatic region subject to epigenetic control of gene expression, wherein said heterochromatic region does not modulate expression of said target nucleic acid molecule; and
    assaying for a modification to said heterochromatic region after treatment with said oligomeric compound.

2. The method of claim 1, wherein said modification to said heterochromatic region is selected from the group consisting of acetylation, deacetylation, phosphorylation, dephosphorylation, methylation, demethylation, ubiquitination, sumoylation, pseudouridylation of said heterochromatic region and any combination thereof.

3. The method of claim 1, wherein said modification to said heterochromatic region is a change in binding of at least one protein to said heterochromatic region.

4. The method of claim 1, wherein the oligomeric compound is an siRNA.

* * * * *